US012773357B2

(12) United States Patent
Willhaus et al.

(10) Patent No.: US 12,773,357 B2
(45) Date of Patent: Oct. 27, 2026

(54) ABSORBENT ARTICLES WITH ABSORBENT CHASSIS AND BELT ELASTIC ARRANGEMENTS AND FRANGIBLE PATHWAYS

(71) Applicant: The Procter & Gamble Company, Cincinnati, OH (US)

(72) Inventors: Keith Richard Willhaus, Cincinnati, OH (US); Jeromy Thomas Raycheck, South Lebanon, OH (US); Jeffry Rosiak, Loveland, OH (US); Jason Edward Naylor, Loveland, OH (US); John Andrew Strasemeier, Aurora, IN (US); Michael Devin Long, Harrison Township, OH (US); Nicholas Alexander Taylor, Woodlawn, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 395 days.

(21) Appl. No.: 18/214,586

(22) Filed: Jun. 27, 2023

(65) Prior Publication Data

US 2024/0000625 A1 Jan. 4, 2024

Related U.S. Application Data

(60) Provisional application No. 63/432,402, filed on Dec. 14, 2022, provisional application No. 63/357,043,
(Continued)

(51) Int. Cl.
*A61F 13/49* (2006.01)
*A61F 13/15* (2006.01)
(Continued)

(52) U.S. Cl.
CPC .. *A61F 13/49011* (2013.01); *A61F 13/15585* (2013.01); *A61F 13/15699* (2013.01);
(Continued)

(58) Field of Classification Search
CPC .......... A61F 13/15585; A61F 13/15699; A61F 13/15723; A61F 13/49011; A61F 13/4902;
(Continued)

(56) References Cited

U.S. PATENT DOCUMENTS

| | | | |
|---|---|---|---|
| 4,610,680 | A | 9/1986 | Lafleur |
| 4,872,871 | A | 10/1989 | Proxmire et al. |

(Continued)

FOREIGN PATENT DOCUMENTS

| | | | |
|---|---|---|---|
| DE | 19813334 | A1 | 9/1999 |
| DE | 20220237 | U1 | 3/2003 |

(Continued)

OTHER PUBLICATIONS

All Office Actions; U.S. Appl. No. 18/214,548, filed Jun. 27, 2023.
(Continued)

*Primary Examiner* — Michele Kidwell
(74) *Attorney, Agent, or Firm* — Charles R. Matson

(57) ABSTRACT

The present disclosure relates to absorbent articles comprising a first belt and a second belt, which may include a frangible pathway comprising lines of weakness. The belts may also comprise elastic strands positioned between and connected with a first substrate and a second substrate. The elastic strands may be severed at the lines of weakness, and the cut elastic strands may be continuously bonded between the first substrate and the second substrate. The arrangements of the frangible pathways relative to belt elastic positions herein may be configured to help ensure the belts
(Continued)

may be relatively easily torn along the frangible pathways without the need to also tear uncut elastic strands.

16 Claims, 30 Drawing Sheets

Related U.S. Application Data filed on Jun. 30, 2022, provisional application No. 63/432,400, filed on Dec. 14, 2022, provisional application No. 63/432,401, filed on Dec. 14, 2022, provisional application No. 63/432,403, filed on Dec. 14, 2022, provisional application No. 63/432,404, filed on Dec. 14, 2022, provisional application No. 63/432,406, filed on Dec. 14, 2022, provisional application No. 63/432,410, filed on Dec. 14, 2022, provisional application No. 63/432,413, filed on Dec. 14, 2022.

(51) Int. Cl.

| | |
|---|---|
| ***A61F 13/493*** | (2006.01) |
| ***A61F 13/496*** | (2006.01) |
| ***A61F 13/512*** | (2006.01) |
| ***A61F 13/514*** | (2006.01) |
| ***A61F 13/551*** | (2006.01) |
| ***A61F 13/56*** | (2006.01) |
| ***A61F 13/62*** | (2006.01) |
| ***A61F 13/64*** | (2006.01) |
| ***A61F 13/68*** | (2006.01) |
| ***A61F 13/84*** | (2006.01) |

(52) U.S. Cl.

CPC .. *A61F 13/15723* (2013.01); *A61F 13/15739* (2013.01); *A61F 13/15747* (2013.01); *A61F 13/15756* (2013.01); *A61F 13/4902* (2013.01); *A61F 13/493* (2013.01); *A61F 13/496* (2013.01); *A61F 13/5126* (2013.01); *A61F 13/51478* (2013.01); *A61F 13/5622* (2013.01); *A61F 13/5644* (2013.01); *A61F 13/565* (2013.01); *A61F 13/5655* (2013.01); *A61F 13/62* (2013.01); *A61F 13/622* (2013.01); *A61F 13/625* (2013.01); *A61F 13/64* (2013.01); *A61F 13/68* (2013.01); *A61F 13/84* (2013.01); *A61F 2013/15292* (2013.01); *A61F 2013/15406* (2013.01); *A61F 2013/15934* (2013.01); *A61F 2013/49025* (2013.01); *A61F 2013/49087* (2013.01); *A61F 13/5512* (2013.01); *A61F 2013/8497* (2013.01)

(58) Field of Classification Search

CPC .............. A61F 13/49061; A61F 13/493; A61F 13/496; A61F 13/5126; A61F 13/51478; A61F 13/5512; A61F 13/5622; A61F 13/5644; A61F 13/565; A61F 13/5655; A61F 13/62; A61F 13/622; A61F 13/625; A61F 13/64; A61F 13/68; A61F 13/84; A61F 2013/15406; A61F 2013/15934; A61F 2013/49025; A61F 2013/49087; A61F 2013/8497; A61F 2013/55125; A61F 13/56; A61F 13/49007; A61F 2013/49063; A61F 2013/8402; A61F 13/49001

See application file for complete search history.

(56) References Cited

U.S. PATENT DOCUMENTS

| | | | |
|---|---|---|---|
| 5,074,854 | A | 12/1991 | Davis |
| H1420 | H | 2/1995 | Richardson |
| 5,575,784 | A | 11/1996 | Ames-ooten et al. |
| 5,624,420 | A | 4/1997 | Bridges et al. |
| 5,766,389 | A | 6/1998 | Brandon et al. |
| 5,897,546 | A | 4/1999 | Kido et al. |
| 6,027,484 | A | 2/2000 | Romare |
| 6,113,717 | A | 9/2000 | Vogt et al. |
| 6,287,287 | B1 | 9/2001 | Elsberg |
| 6,497,695 | B1 | 12/2002 | Bruemmer-prestley et al. |
| 6,508,797 | B1 | 1/2003 | Pozniak et al. |
| 6,508,799 | B1 | 1/2003 | Freiburger et al. |
| 6,524,294 | B1 | 2/2003 | Hilston et al. |
| 6,575,949 | B1 | 6/2003 | Waksmundzki et al. |
| 6,579,275 | B1 | 6/2003 | Pozniak et al. |
| 6,585,855 | B2 | 7/2003 | Drew et al. |
| 6,712,922 | B2 | 3/2004 | Sorenson et al. |
| 6,743,321 | B2 | 6/2004 | Guralski |
| 6,752,796 | B2 | 6/2004 | Karami |
| 6,783,487 | B2 | 8/2004 | Duhm et al. |
| 6,838,040 | B2 | 1/2005 | Mlinar et al. |
| 6,976,978 | B2 | 12/2005 | Ruman et al. |
| 6,991,696 | B2 | 1/2006 | Wagner et al. |
| 7,077,834 | B2 | 7/2006 | Bishop et al. |
| 7,150,730 | B2 | 12/2006 | Hasler et al. |
| 7,156,833 | B2 | 1/2007 | Couture-dorschner |
| 7,250,549 | B2 | 7/2007 | Richlen et al. |
| 7,297,139 | B2 | 11/2007 | Price et al. |
| 7,393,429 | B2 | 7/2008 | Tachibana |
| 7,473,818 | B2 | 1/2009 | Datta et al. |
| 7,497,852 | B2 | 3/2009 | Kawakami |
| 7,527,617 | B2 | 5/2009 | Shimada et al. |
| 7,608,068 | B2 | 10/2009 | Fujioka |
| 7,621,901 | B2 | 11/2009 | Karami |
| 7,637,898 | B2 | 12/2009 | Kuen et al. |
| 7,641,641 | B2 | 1/2010 | Ramshak |
| 7,686,795 | B2 | 3/2010 | Ichikawa et al. |
| 7,708,857 | B2 | 5/2010 | Ukegawa |
| 7,789,868 | B2 | 9/2010 | Tachibana |
| 8,002,761 | B2 | 8/2011 | Utsunomiya et al. |
| 8,007,622 | B2 | 8/2011 | Heller |
| 8,034,039 | B2 | 10/2011 | Nakaoka et al. |
| 8,043,274 | B2 | 10/2011 | Mlinar et al. |
| 8,066,684 | B2 | 11/2011 | Fujioka |
| 8,066,687 | B2 | 11/2011 | Ashton et al. |
| 8,118,799 | B2 | 2/2012 | Datta et al. |
| 8,162,912 | B2 | 4/2012 | Schlinz et al. |
| 8,192,417 | B2 | 6/2012 | Kusumi et al. |
| 8,216,200 | B2 | 7/2012 | Meetz et al. |
| 8,277,430 | B2 | 10/2012 | Tabor et al. |
| 8,361,048 | B2 | 1/2013 | Kuen |
| 8,388,595 | B2 | 3/2013 | Van Gompel et al. |
| 8,557,068 | B2 | 10/2013 | Ito et al. |
| 8,569,571 | B2 | 10/2013 | Kline et al. |
| 8,657,802 | B2 | 2/2014 | Roe et al. |
| 8,663,184 | B2 | 3/2014 | Liu et al. |
| 8,753,466 | B2 | 6/2014 | Thorson |
| 8,771,449 | B2 | 7/2014 | Takino et al. |
| 8,945,324 | B2 | 2/2015 | Hahn et al. |
| 9,011,406 | B2 | 4/2015 | Torigoshi et al. |
| 9,028,462 | B2 | 5/2015 | Poole et al. |
| 9,050,217 | B2 | 6/2015 | Gassner et al. |
| 9,060,905 | B2 | 6/2015 | Wang et al. |
| 9,066,832 | B2 | 6/2015 | Gassner et al. |
| 9,066,833 | B2 | 6/2015 | Gassner |
| 9,072,632 | B2 | 7/2015 | Lavon |
| 9,089,458 | B2 | 7/2015 | Faulks et al. |
| 9,138,361 | B2 | 9/2015 | Faulks et al. |
| 9,173,781 | B2 | 11/2015 | Otsubo et al. |
| 9,226,861 | B2 | 1/2016 | Lavon |
| 9,561,138 | B2 | 2/2017 | Mukai et al. |
| 9,668,925 | B2 | 6/2017 | Mukai et al. |
| 9,750,647 | B2 | 9/2017 | Umebayashi |
| 9,789,010 | B2 | 10/2017 | Long et al. |
| 9,820,536 | B2 | 11/2017 | Sakaguchi et al. |

(56) References Cited

U.S. PATENT DOCUMENTS

| | | | | |
|---|---|---|---|---|
| 10,034,801 | B2 | 7/2018 | Seitz et al. | |
| 10,123,914 | B2 | 11/2018 | Kobayashi et al. | |
| 10,188,560 | B2 | 1/2019 | Mueller et al. | |
| 10,292,874 | B2 | 5/2019 | Wade et al. | |
| 10,687,988 | B2 | 6/2020 | Morimoto et al. | |
| 10,736,795 | B2 | 8/2020 | Bianchi et al. | |
| 10,799,398 | B2 | 10/2020 | Eimann et al. | |
| 10,905,602 | B2 | 2/2021 | Olsson | |
| 10,993,844 | B2 | 5/2021 | Olsson et al. | |
| 11,246,767 | B2 | 2/2022 | Roszkowiak et al. | |
| 11,304,859 | B2 | 4/2022 | Jeon et al. | |
| 11,426,312 | B2 | 8/2022 | Collins et al. | |
| 11,672,708 | B2 | 6/2023 | Johnson et al. | |
| 11,752,045 | B2 | 9/2023 | Johnson et al. | |
| 11,883,268 | B2 | 1/2024 | Johnson et al. | |
| 12,310,827 | B2 | 5/2025 | Johnson et al. | |
| 2002/0032427 | A1 | 3/2002 | Schmitz et al. | |
| 2002/0065503 | A1 | 5/2002 | Guidotti | |
| 2002/0112276 | A1* | 8/2002 | Ruman | A61F 13/496 2/400 |
| 2002/0148557 | A1 | 10/2002 | Heller | |
| 2003/0055389 | A1 | 3/2003 | Sanders et al. | |
| 2003/0088223 | A1 | 5/2003 | Vogt et al. | |
| 2003/0130641 | A1 | 7/2003 | Richlen et al. | |
| 2003/0220626 | A1 | 11/2003 | Karami | |
| 2004/0182502 | A1 | 9/2004 | Wagner et al. | |
| 2004/0186451 | A1 | 9/2004 | Bishop et al. | |
| 2004/0193135 | A1 | 9/2004 | Van Gompel | |
| 2005/0148974 | A1 | 7/2005 | Datta et al. | |
| 2005/0177125 | A1 | 8/2005 | Kondo | |
| 2005/0192553 | A1 | 9/2005 | Hasler et al. | |
| 2006/0052763 | A1* | 3/2006 | Tachibana | A61F 13/15699 604/395 |
| 2006/0129119 | A1 | 6/2006 | Kistler | |
| 2006/0135936 | A1 | 6/2006 | Markovich et al. | |
| 2006/0241559 | A1* | 10/2006 | Buhrow | A61F 13/493 604/385.09 |
| 2006/0293639 | A1 | 12/2006 | Van Gompel | |
| 2008/0015534 | A1 | 1/2008 | Kusumi et al. | |
| 2008/0103470 | A1 | 5/2008 | Samuelsson et al. | |
| 2008/0114322 | A1 | 5/2008 | Schmoker et al. | |
| 2008/0134487 | A1 | 6/2008 | Hartono | |
| 2008/0154223 | A1 | 6/2008 | Fujioka | |
| 2008/0234649 | A1 | 9/2008 | Hamall et al. | |
| 2008/0249493 | A1 | 10/2008 | Kobayashi et al. | |
| 2009/0149827 | A1 | 6/2009 | Mlinar et al. | |
| 2009/0254059 | A1 | 10/2009 | Nilsson et al. | |
| 2009/0312734 | A1 | 12/2009 | Lavon et al. | |
| 2011/0098668 | A1 | 4/2011 | Thorson | |
| 2011/0155304 | A1 | 6/2011 | Sakaguchi | |
| 2012/0053548 | A1* | 3/2012 | Ashton | A61F 13/5655 604/385.11 |
| 2013/0012905 | A1 | 1/2013 | Katsuragawa et al. | |
| 2013/0231625 | A1 | 9/2013 | Ellefson et al. | |
| 2013/0306226 | A1 | 11/2013 | Zink | |
| 2014/0110037 | A1 | 4/2014 | Verboomen | |
| 2014/0113792 | A1 | 4/2014 | Verboomen et al. | |
| 2014/0114272 | A1 | 4/2014 | Schoon et al. | |
| 2014/0135730 | A1 | 5/2014 | Mlinar et al. | |
| 2014/0155855 | A1 | 6/2014 | Romzek et al. | |
| 2014/0187405 | A1 | 7/2014 | Volp et al. | |
| 2017/0105883 | A1 | 4/2017 | Nishikawa et al. | |
| 2017/0266941 | A1 | 9/2017 | Eimann | |
| 2019/0099304 | A1 | 4/2019 | Berry | |
| 2019/0209392 | A1 | 7/2019 | Johnson et al. | |
| 2020/0155373 | A1* | 5/2020 | Tallman | A61F 13/49007 |
| 2020/0163810 | A1 | 5/2020 | Johnson et al. | |
| 2021/0093485 | A1 | 4/2021 | Ljungberg et al. | |
| 2021/0369510 | A1 | 12/2021 | Ljungberg et al. | |
| 2023/0127980 | A1 | 4/2023 | Umebayashi | |
| 2023/0146261 | A1 | 5/2023 | Seitz et al. | |
| 2024/0173175 | A1 | 5/2024 | Johnson et al. | |

FOREIGN PATENT DOCUMENTS

| | | | |
|---|---|---|---|
| EP | 0570980 | B1 | 7/1997 |
| EP | 0705088 | B1 | 5/1999 |
| EP | 1027874 | A2 | 8/2000 |
| EP | 0955976 | B1 | 3/2002 |
| EP | 1128790 | B1 | 5/2003 |
| EP | 1779827 | A1 | 5/2007 |
| EP | 2486905 | B1 | 4/2017 |
| EP | 3053562 | B1 | 3/2022 |
| JP | H0432718 | U | 3/1992 |
| JP | 3209377 | B2 | 9/2001 |
| JP | 2001258938 | A | 9/2001 |
| JP | 2002017778 | A | 1/2002 |
| JP | 3429383 | B2 | 7/2003 |
| JP | 2003290286 | A | 10/2003 |
| JP | 3578802 | B2 | 7/2004 |
| JP | 2004329590 | A | 11/2004 |
| JP | 2005287982 | A | 10/2005 |
| JP | 3737709 | B2 | 11/2005 |
| JP | 2006034402 | A | 2/2006 |
| JP | 2006055343 | A | 3/2006 |
| JP | 2006068211 | A | 3/2006 |
| JP | 2006204385 | A | 8/2006 |
| JP | 4037216 | B2 | 11/2007 |
| JP | 4090913 | B2 | 3/2008 |
| JP | 4131683 | B2 | 6/2008 |
| JP | 2008142345 | A | 6/2008 |
| JP | 4163144 | B2 | 8/2008 |
| JP | 2008302138 | A | 12/2008 |
| JP | 4240464 | B2 | 1/2009 |
| JP | 4260711 | B2 | 2/2009 |
| JP | 4276556 | B2 | 3/2009 |
| JP | 4280187 | B2 | 3/2009 |
| JP | 4312084 | B2 | 5/2009 |
| JP | 4444078 | B2 | 1/2010 |
| JP | 4444079 | B2 | 1/2010 |
| JP | 4502882 | B2 | 4/2010 |
| JP | 4508892 | B2 | 5/2010 |
| JP | 4511284 | B2 | 5/2010 |
| JP | 2010136787 | A | 6/2010 |
| JP | 2010246901 | A | 11/2010 |
| JP | 4672651 | B2 | 1/2011 |
| JP | 4682085 | B2 | 2/2011 |
| JP | 4745119 | B2 | 5/2011 |
| JP | 4758821 | B2 | 6/2011 |
| JP | 4801498 | B2 | 8/2011 |
| JP | 4908255 | B2 | 1/2012 |
| JP | 4926742 | B2 | 2/2012 |
| JP | 5009040 | B2 | 6/2012 |
| JP | 5014452 | B2 | 8/2012 |
| JP | 5106253 | B2 | 10/2012 |
| JP | 5107447 | B2 | 10/2012 |
| JP | 5241457 | B2 | 4/2013 |
| JP | 5244226 | B2 | 4/2013 |
| JP | 5352408 | B2 | 8/2013 |
| JP | 5438952 | B2 | 12/2013 |
| JP | 5568369 | B2 | 6/2014 |
| JP | 5572822 | B2 | 7/2014 |
| JP | 5632346 | B2 | 10/2014 |
| JP | 5632521 | B2 | 10/2014 |
| JP | 5638305 | B2 | 10/2014 |
| JP | 5728907 | B2 | 4/2015 |
| JP | 5868105 | B2 | 1/2016 |
| JP | 6024486 | B2 | 11/2016 |
| JP | 6159109 | B2 | 6/2017 |
| JP | 6176958 | B2 | 7/2017 |
| JP | 6180025 | B2 | 7/2017 |
| JP | 6298274 | B2 | 3/2018 |
| JP | 2018139718 | A | 9/2018 |
| JP | 6429710 | B2 | 11/2018 |
| JP | 2018187217 | A | 11/2018 |
| JP | 6913131 | B2 | 7/2021 |
| JP | 6941026 | B2 | 9/2021 |
| JP | 2023042747 | A | 3/2023 |
| JP | 7315360 | B2 | 7/2023 |
| WO | 2009084643 | A1 | 7/2009 |
| WO | 2014080795 | A1 | 5/2014 |
| WO | 2014196215 | A1 | 12/2014 |

(56) References Cited

FOREIGN PATENT DOCUMENTS

| | | | |
|---|---|---|---|
| WO | 2015046632 | A1 | 4/2015 |
| WO | 2016013662 | A1 | 1/2016 |
| WO | 2016104753 | A1 | 6/2016 |
| WO | 2016121236 | A1 | 8/2016 |
| WO | 2018207512 | A1 | 11/2018 |
| WO | 2020062132 | A1 | 4/2020 |
| WO | 2020195099 | A1 | 10/2020 |
| WO | 2021241553 | A1 | 12/2021 |
| WO | 2022004727 | A1 | 1/2022 |

OTHER PUBLICATIONS

All Office Actions; U.S. Appl. No. 18/214,564, filed Jun. 27, 2023.
All Office Actions; U.S. Appl. No. 18/214,569, filed Jun. 27, 2023.
All Office Actions; U.S. Appl. No. 18/214,573, filed Jun. 27, 2023.
All Office Actions; U.S. Appl. No. 18/214,603, filed Jun. 27, 2023.
All Office Actions; U.S. Appl. No. 18/214,680, filed Jun. 27, 2023.
All Office Actions; U.S. Appl. No. 18/214,691, filed Jun. 27, 2023.
All Office Actions; U.S. Appl. No. 18/214,718, filed Jun. 27, 2023.
All Office Actions; U.S. Appl. No. 18/214,750, filed Jun. 27, 2023.
All Office Actions; U.S. Appl. No. 18/342,054, filed Jun. 27, 2023.
All Office Actions; U.S. Appl. No. 18/342,058, filed Jun. 27, 2023.
All Office Actions; U.S. Appl. No. 18/214,626, filed Jun. 27, 2023.
Unpublished U.S. Appl. No. 18/214,548, filed Jun. 27, 2023, to Jeromy Thomas Raycheck et al.
Unpublished U.S. Appl. No. 18/214,564, filed Jun. 27, 2023, to Uwe Schneider et al.
Unpublished U.S. Appl. No. 18/214,569, filed Jun. 27, 2023, to Keith Richard Willhaus et al.
Unpublished U.S. Appl. No. 18/214,573, filed Jun. 27, 2023, to Jeromy Thomas Raycheck et al.
Unpublished U.S. Appl. No. 18/214,603, filed Jun. 27, 2023, to Keith Richard Willhaus et al.
Unpublished U.S. Appl. No. 18/214,626, filed Jun. 27, 2023, to Keith Richard Willhaus et al.
Unpublished U.S. Appl. No. 18/214,680, filed Jun. 27, 2023, to Jeromy Thomas Raycheck et al.
Unpublished U.S. Appl. No. 18/214,691, filed Jun. 27, 2023, to Uwe Schneider et al.
Unpublished U.S. Appl. No. 18/214,718, filed Jun. 27, 2023, to Keith Richard Willhaus et al.
Unpublished U.S. Appl. No. 18/214,750, filed Jun. 27, 2023, to Jeffry Rosiak et al.
Unpublished U.S. Appl. No. 18/342,054, filed Jun. 27, 2023, to Nicholas Alexander Taylor et al.
Unpublished U.S. Appl. No. 18/342,058, filed Jun. 27, 2023, to Han Xu et al.
PCT Search Report and Written Opinion for PCT/US2023/069115 dated Sep. 21, 2023,11 pages.
All Office Actions; U.S. Appl. No. 18/967,797, filed Dec. 4, 2024; See Patent Center.
All Office Actions; U.S. Appl. No. 18/967,768, filed Dec. 4, 2024; See Patent Center.
All Office Actions; U.S. Appl. No. 18/967,824, filed Dec. 4, 2024; See Patent Center.
All Office Actions; U.S. Appl. No. 18/968,031, filed Dec. 4, 2024; See Patent Center.
All Office Actions; U.S. Appl. No. 18/978,059, filed Dec. 12, 2024; See Patent Center.
Unpublished U.S. Appl. No. 18/967,797, filed Dec. 4, 2024, Kaitlyn Nicole Taylor et al. See Patent Center.
Unpublished U.S. Appl. No. 18/967,768, filed Dec. 4, 2024, Keith Richard Willhaus et al. See Patent Center.
Unpublished U.S. Appl. No. 18/967,824, filed on Dec. 4, 2024, Jeffry Rosiak et al. See Patent Center.
Unpublished U.S. Appl. No. 18/968,031, filed Dec. 4, 2024, Keith Richard Willhaus et al. See Patent Center.
Unpublished U.S. Appl. No. 18/978,059, filed Dec. 12, 2024, Jeromy Thomas Raycheck et al. See Patent Center.
All Office Actions; U.S. Appl. No. 19/426,251, filed Dec. 19, 2025; See Patent Center.
Unpublished U.S. Appl. No. 19/426,251, filed Dec. 19, 2025, to Keith Richard Willhaus et al.; See Patent Center.
All Office Actions; U.S. Appl. No. 19/657,148, filed on Apr. 24, 2026; See Patent Center.
U.S. Unpublished U.S. Appl. No. 19/657,148, filed on Apr. 24, 2026, to Jeromy Thomas Raycheck et al.; See Patent Center.

* cited by examiner

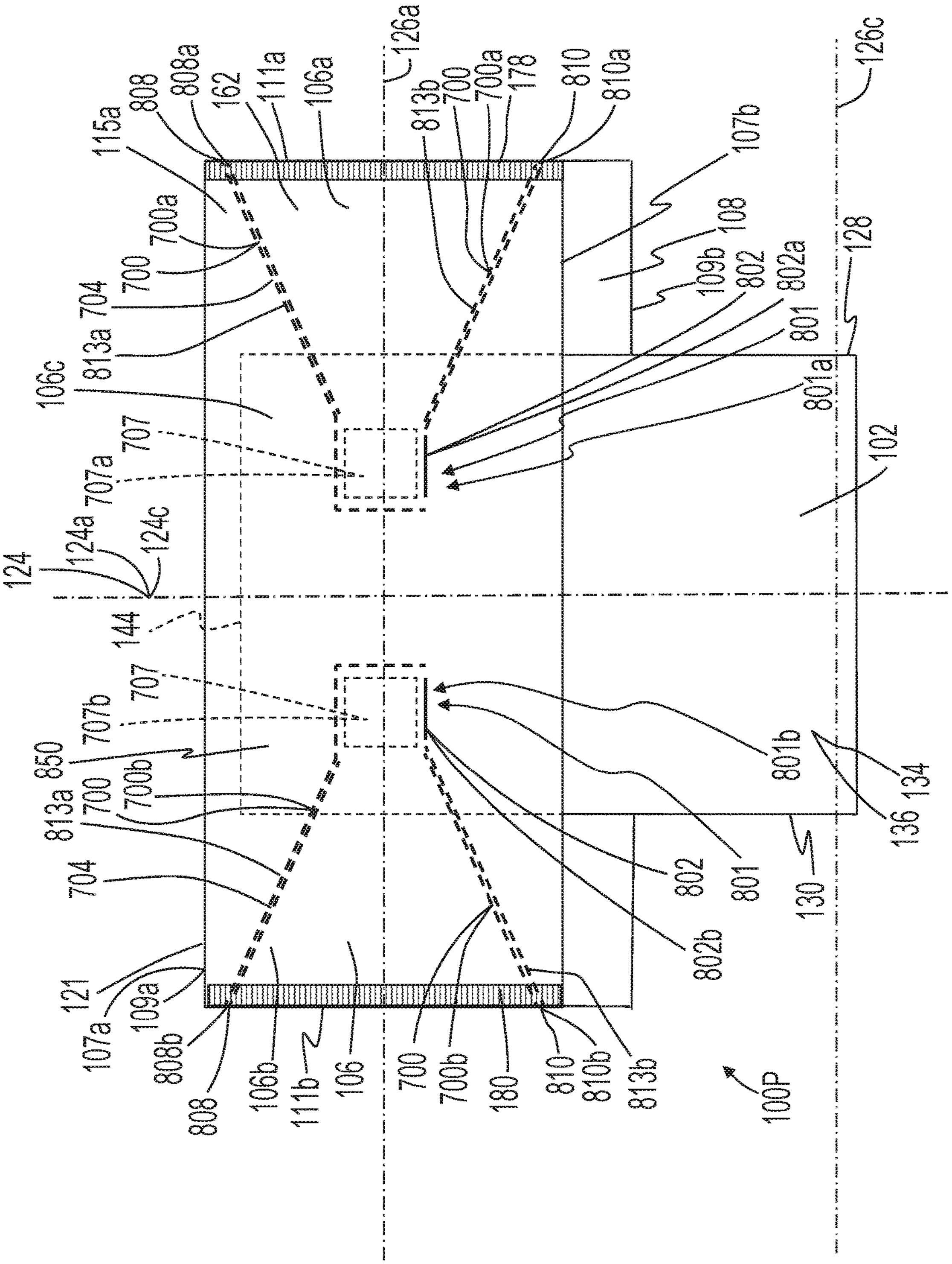
Fig. 6B1

ABSORBENT ARTICLES WITH ABSORBENT CHASSIS AND BELT ELASTIC ARRANGEMENTS AND FRANGIBLE PATHWAYS

CROSS REFERENCE TO RELATED APPLICATION

This application claims the benefit, under 35 USC 119(e), of U.S. Provisional Patent Application No. 63/432,402 filed on Dec. 14, 2022; U.S. Provisional Patent Application No. 63/357,043, filed on Jun. 30, 2022; U.S. Provisional Patent Application No. 63/432,400, filed on Dec. 14, 2022; U.S. Provisional Patent Application No. 63/432,401, filed on Dec. 14, 2022; U.S. Provisional Patent Application No. 63/432,403, filed on Dec. 14, 2022; U.S. Provisional Patent Application No. 63/432,404, filed on Dec. 14, 2022; U.S. Provisional Patent Application No. 63/432,406, filed on Dec. 14, 2022; U.S. Provisional Patent Application No. 63/432,410, filed on Dec. 14, 2022; and U.S. Provisional Patent Application No. 63/432,413, filed on Dec. 14, 2022, each of which are herein incorporated by reference in their entirety.

FIELD OF THE INVENTION

The present disclosure relates to absorbent articles, and more particularly, to absorbent articles with belt elastic configurations in front and/or back waist regions including one or more frangible pathways.

BACKGROUND OF THE INVENTION

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers, and in turn, forms corrugations and rugosities. The resulting elastomeric laminate is stretchable to the extent that the corrugations allow the elastic strands to elongate.

Absorbent articles in the form of diaper pants may also be configured with an absorbent chassis connected with front and back elastic belts, wherein opposing end regions of the front and back belts are connected with each other at side seams. In some instances, the elasticity of the front and back belts is removed in regions where the chassis connects with the belts. Thus, in some converting configurations adapted to assemble such diaper pants, stretched elastic strands are glued between two continuous nonwoven webs to form an elastic laminate. Regions of the elastic strands may then be intermittently deactivated along the length of the elastic laminate by cutting the elastic strands in areas to be connected with the chassis, sometimes referred to as tummy elastic cutting.

Some caregivers of older incontinent babies or toddlers may prefer a closed, pant-style disposable absorbent article to enable application to, and removal from, a child while the child is in a standing position. One disadvantage of this product form is that the removal and disposal of feces-containing products may be unhygienic and inconvenient. For example, pulling the product down could cause feces to smear down the legs of a user. In other examples, a caregiver may tear open the bonded sides using force. In turn, the force used can lead to a rapid release of energy from the diaper, causing the caregiver to lose control of the product and allowing feces to spill out. In contrast, removal and disposal of traditional open or taped diaper forms with fasteners may be readily accomplished while the child is laying on their back. In this case, the fasteners are opened, the diaper is removed from under the child, rolled into a roughly cylindrical shape, and then the fasteners are secured around the rolled, soiled diaper, closing the leg openings for hygienic disposal.

In order to avoid having to remove soiled diaper pants from a wearer by sliding the soiled diaper pant down the wearer's legs or tearing bonded side seams, some diaper pants may be configured with tear lines in the front belt or back belt. Such tear lines may include perforations that allow a caregiver to more easily separate the belt along the perforation lines. Once the belt is separated, the diaper pant can be more easily removed from the wearer without having to slide the diaper pant down the wearer's legs, in a similar manner as a traditional open taped diaper form. However, various challenges may be associated with diaper pants having tear lines. For example, some elastic belts may include several elastic strands, and as such, there may be challenges associated with cutting the elastic strands in the location of the perforation line. There may be challenges associated with ensuring that all elastic strands extending through the tear line are also consistently cut. When uncut elastic strands extend through a tear line in a belt of a diaper pant, such uncut elastic strands would need to be broken during removal of a diaper pant from a wearer. Such uncut elastic strands can be very difficult to break or tear and may cause the tear to propagate away from the intended pathway, causing the caregiver to have to restart the tear again at a location of tear deviation.

Consequently, it would be beneficial to create pant-style articles that provide the caregiver the ability to remove and dispose soiled products in a similar manner to traditional open diaper forms. In addition, it would be beneficial to pant diapers with frangible pathways in elastic belts that extend through consistently cut elastic strands.

SUMMARY OF THE INVENTION

In one form, an absorbent article comprises: a first belt comprising an inner wearer facing surface and an outer garment facing surface, the first belt further comprising a laterally extending inner edge and a laterally extending outer edge, the outer edge positioned longitudinally outward of the inner edge; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, the chassis comprising a longitudinally extending first side edge and a longitudinally extending second side edge laterally separated from the first side edge by a first end edge and a second end edge longitudinally separate from the first end edge, and wherein longitudinally opposing end regions of the chassis are connected with the first belt and the second belt; wherein a portion of the chassis overlaps the inner wearer facing surface of the first belt to define a chassis overlap region; a frangible pathway in the first belt extending across the overlap region between a proximal terminus on the inner edge and a distal terminus on the outer edge of the first belt, the first frangible pathway comprising a first tear zone extending from the overlap region to the distal terminus, and a second tear zone extending from the overlap region to the proximal terminus; and the distal terminus and the proximal terminus positioned laterally between the first side edge of the chassis and the first side seam.

BRIEF DESCRIPTION OF THE DRAWINGS

FIG. 3A1 is a cross-sectional detailed view of another example configuration wherein the first belt is provided with panel layers wherein one panel layer is folded over another panel layer.

FIG. 3A2 is a cross-sectional detailed view of another example configuration wherein the first belt is provided with panel layers wherein one panel layer is folded over another panel layer.

FIG. 6B1 is a front plan view of another configuration of a diaper pant with frangible pathways having a distal terminus and a proximal terminus positioned on a side seams.

FIG. 7AA1 is a cross-sectional view of the fastener component of FIG. 7A taken along line 7AA-7AA.

FIG. 7AA2 is a cross-sectional view of the fastener component of FIG. 7A taken along line 7AA-7AA, wherein the fastener component is integrally formed from belt components.

DETAILED DESCRIPTION OF THE INVENTION

Definitions

Figure 1:
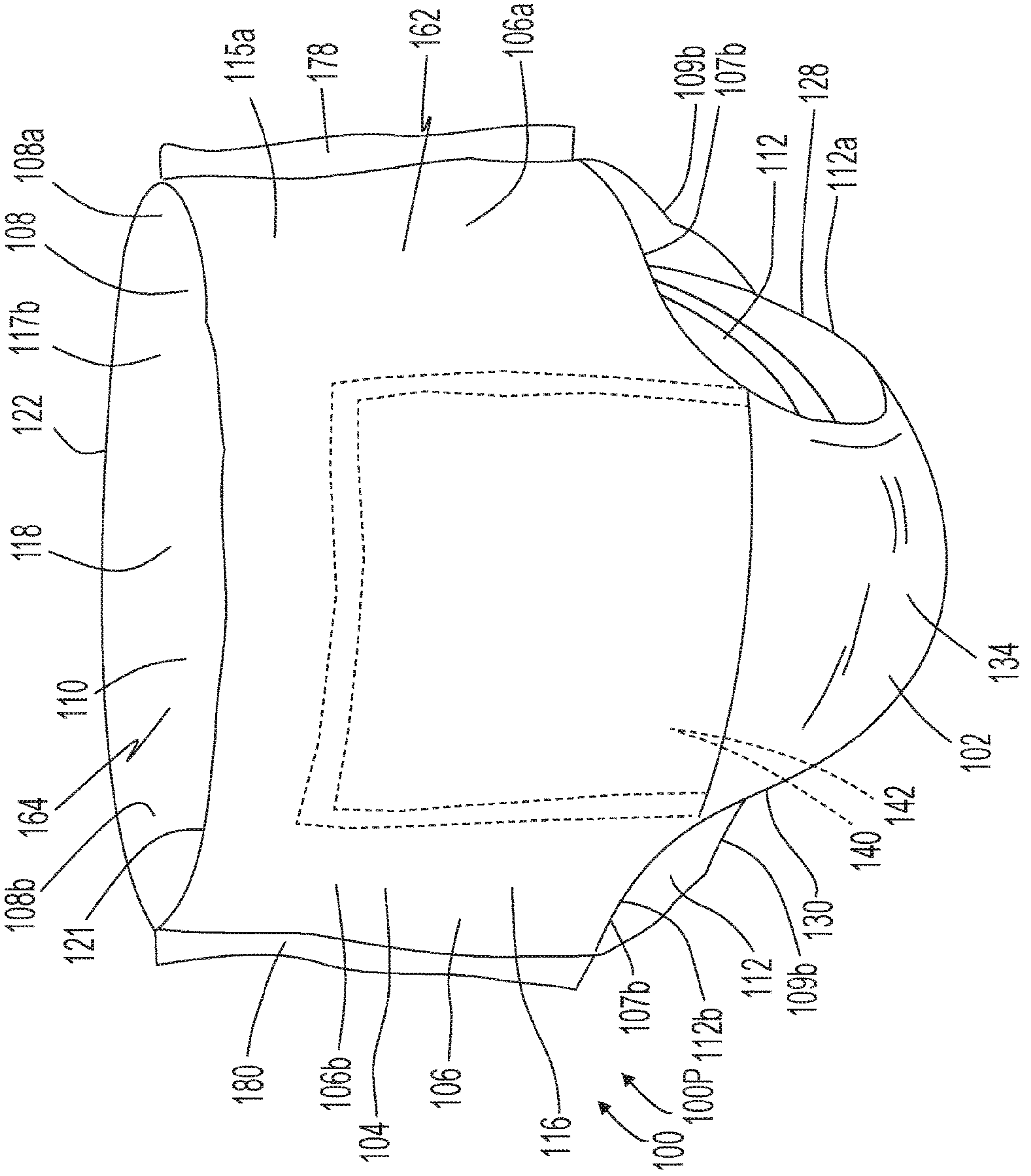
FIG. 1 shows a perspective view of a diaper pant in a pre-fastened configuration.

The following term explanations may be useful in understanding the present disclosure:

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, menstrual pads and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

The terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands, and other sheet-like structures.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "distal" is used to describe a position situated away from a center of a body or from a point of attachment, and the term "proximal" is used to describe a position situated nearer to a center of a body or a point of attachment.

The term "substrate" is used herein to describe a material which is primarily two-dimensional (i.e., in an XY plane) and whose thickness (in a Z direction) is relatively small (i.e., 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry used for measuring yarns or filaments. 1 Decitex=1 gram per 10,000 meters. In other words, if 10,000 linear meters of a yarn or filament weights 500 grams that yarn or filament would have a decitex of 500.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, back waist fastened or seamed). Example diaper pants in various configurations are disclosed in U.S. Pat. Nos. 4,940,464; 5,092,861; 5,246,433; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

The present disclosure relates to absorbent articles including elastic laminates, and more particularly, to absorbent articles having elastic laminates in front and/or back waist regions with frangible pathways. In some configurations, an absorbent article may comprise: a first belt and a second belt. The first belt may comprise an inner wearer facing surface and an outer garment facing surface, a laterally extending inner edge and a laterally extending outer edge, the outer edge positioned longitudinally outward of the inner edge. Laterally opposing end portions of the second belt may be connected with laterally opposing end portions of the first belt at a first side seam and a second side seam to form a waist opening. The absorbent article may also comprise a chassis comprising a topsheet, a backsheet, and an absorbent core positioned between the topsheet and the backsheet. The chassis may comprise a longitudinally extending first side edge and a longitudinally extending second side edge laterally separated from the first side edge by a first end edge and a second end edge longitudinally separate from the first end edge. Longitudinally opposing end regions of the chassis are connected with the first belt and the second belt, wherein a portion of the chassis overlaps the inner wearer facing surface of the first belt to define a chassis overlap region. A frangible pathway in the first belt may extend across a portion of the overlap region between a proximal terminus on the inner edge and a distal terminus on the outer edge of the first belt. The frangible pathway may comprise lines of weakness. The first frangible pathway may also comprise a first tear zone extending from the overlap region to the distal terminus, and a second tear zone extending from the overlap region to the proximal terminus. The distal terminus and the proximal terminus may be positioned laterally between the first side edge and first side seam.

As discussed in more detail below, the first belt may also comprise: elastic strands positioned between and connected with a first substrate and a second substrate. The lines weakness may cut some elastic strands, and the cut elastic strands may be continuously bonded between the first substrate and the second substrate. The lines weakness may also cut all elastic strands extending through the first tear zone between the first side edge of the chassis and the distal terminus, and the lines weakness may cut all elastic strands extending through the second tear zone between the first side edge of the chassis and the proximal terminus. The lines weakness cut at least one elastic strand extending through the first tear zone or the second tear zone in at least one location between the first side edge of the chassis and the second side edge of the chassis. The lines weakness may not cut at least one elastic strand extending between the first side edge of the chassis and the second side edge of the chassis. As discussed below, the arrangements of the frangible pathways relative to belt elastic positions herein may be configured to help ensure the belts may be relatively easily torn along the frangible pathways without the need to also tear uncut elastic strands.

Figure 2A:
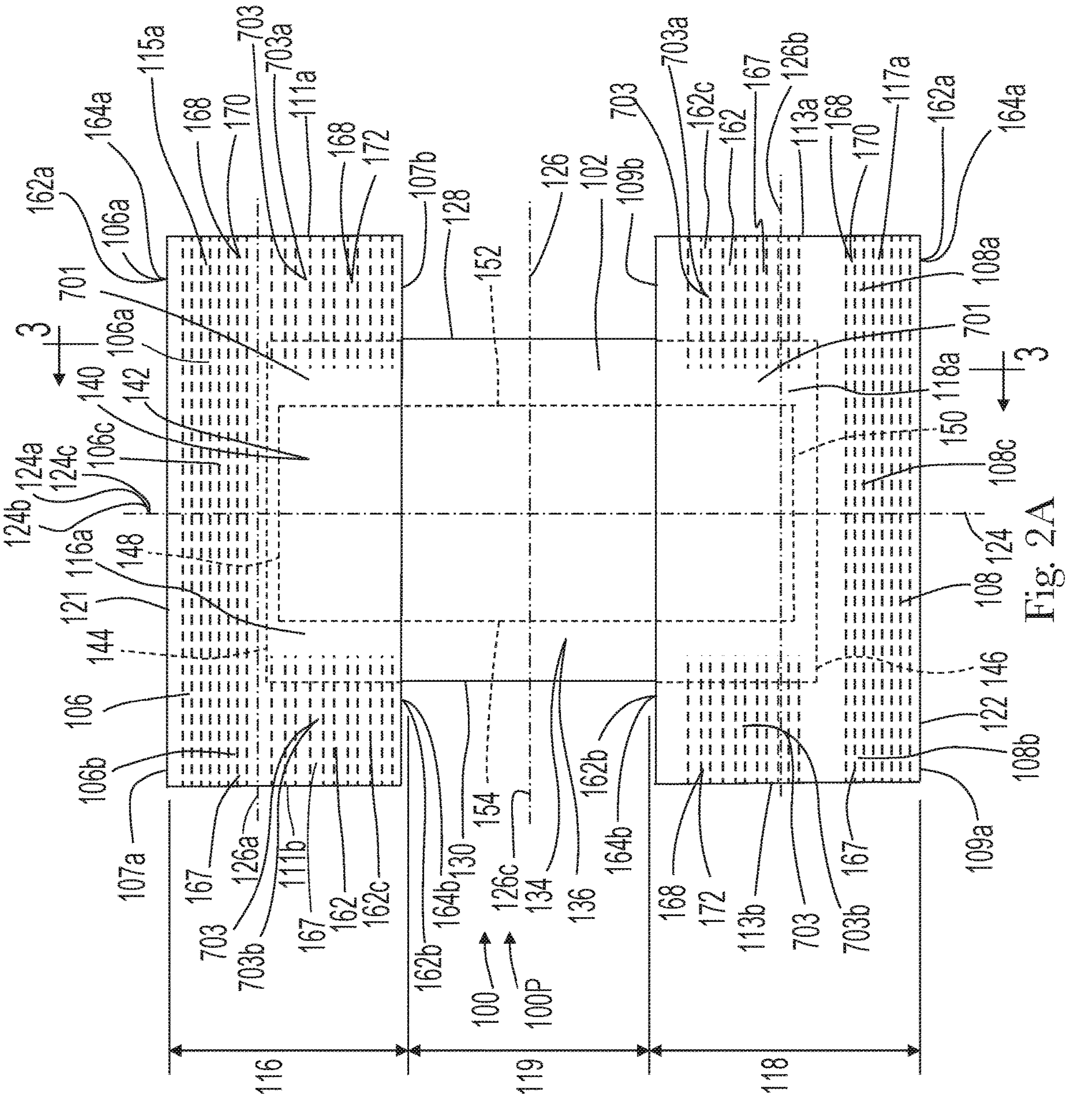
FIG. 2A shows a plan view of a diaper pant with the portion of the diaper that faces away from a wearer oriented toward the viewer.
Figure 2B:
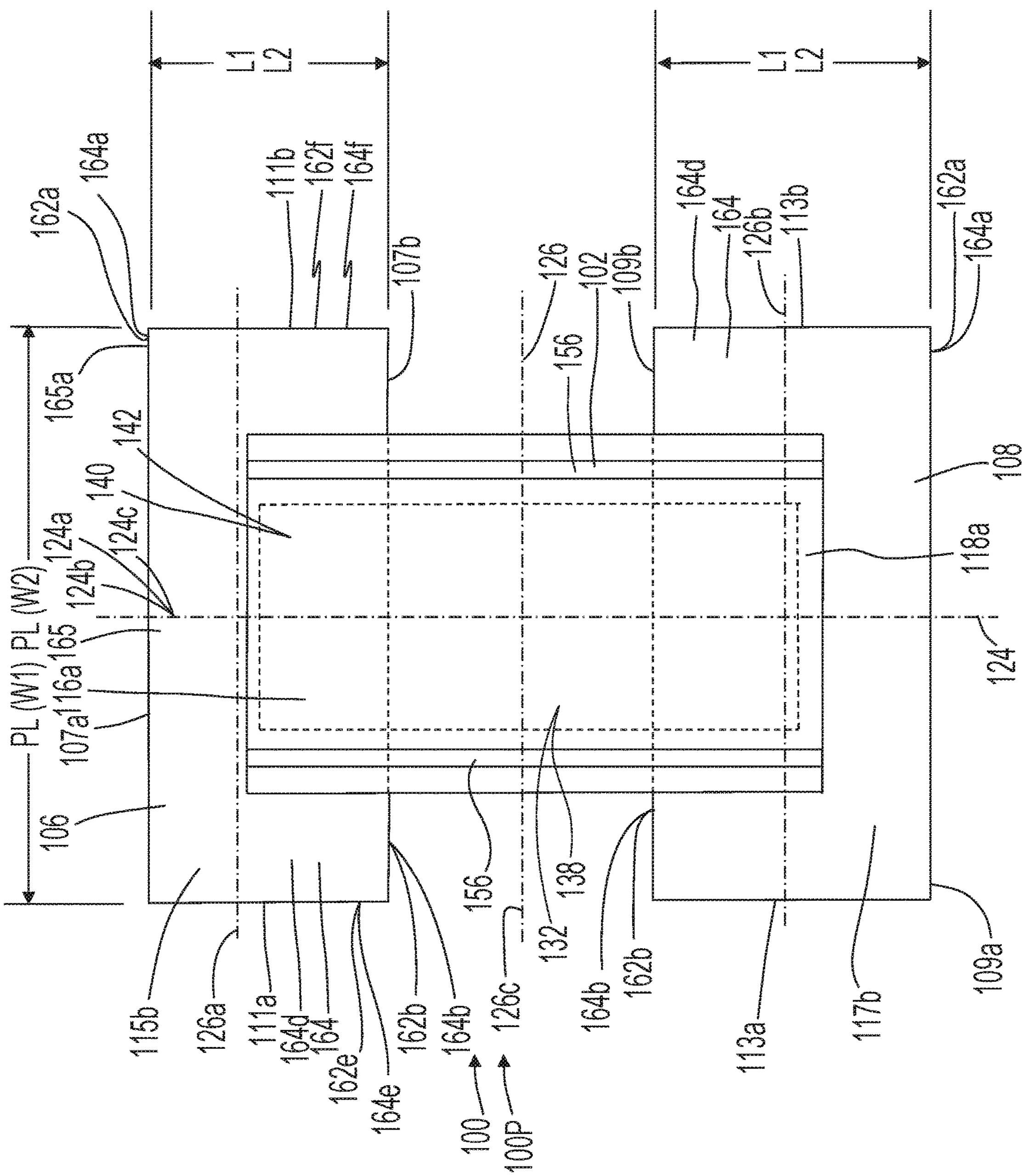
FIG. 2B shows a plan view of a diaper pant with the portion of the diaper that faces toward a wearer oriented toward the viewer.

FIGS. 1-2B show an example of an absorbent article 100 in the form of a diaper pant 100P that may include components constructed in accordance with the configurations disclosed herein. In particular, FIG. 1 shows a perspective views of a diaper pant 100P in a pre-fastened configuration. FIG. 2A shows a plan view of the diaper pant 100P with the portion of the diaper that faces away from a wearer oriented toward the viewer, and FIG. 2B shows a plan view of the diaper pant 100P with the portion of the diaper that faces toward a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIGS. 1-2B, the diaper pant 100P and the chassis 102 each include a first waist region 116, a second waist region 118, and a crotch region 119 disposed intermediate the first and second waist regions. It may also be described that the chassis 102 includes a first end region 116*a*, a second end region 118*a*, and a crotch region 119 disposed intermediate the first and second end regions 116*a*, 118*a*. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a second longitudinal or left side edge 130 of the chassis 102. As previously mentioned, the longitudinal axis 124 extends perpendicularly through the front waist edge 121 and the back waist edge 122, and the lateral axis 126 extends perpendicularly to the longitudinal axis 124. When the diaper pant 100P is worn, the longitudinal direction may extend from the wearer's front waist, through the crotch, to the wearer's back waist. To provide a further frame of reference for the present discussion, the diapers 100P of FIGS. 2A, 2B, and 18B are shown wherein: the first elastic belt 106 comprises a longitudinal centerline 124*a* and lateral centerline 126*a*; the second elastic belt 108 comprises a longitudinal centerline 124*b* and lateral centerline 126*b*; and the chassis 102 comprises a longitudinal centerline 124*c* and lateral centerline 126*c*. The longitudinal centerlines 124*a*, 124*b*, 124*c* are perpendicular to the lateral center lines 126*a*, 126*b*, 126*c*.

As shown in FIGS. 1-2B, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 may be located longitudinally inward from the laterally extending front waist edge 121 in the front waist region 116 and the laterally extending back waist edge 122 in the back waist region 118. In some configurations, the laterally extending end edges 144 and 146 may be coterminous with or located longitudinally outward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer, garment facing surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner, wearer facing surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539, all of which are incorporated by reference herein.

As mentioned above, the diaper pant 100P may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735, all of which are incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,562,646; 5,669,894; and 6,790,798 as well as U.S. Patent Publication Nos. 2004/0158212 A1 and 2004/0097895 A1, all of which are incorporated by reference herein.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1, all of which are incorporated by reference herein.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111*a* and a second longitudinal side edge 111*b* and defines first and second opposing end regions 106*a*, 106*b* and a central region 106*c*. And the second elastic 108 belt extends between a first longitudinal side edge 113*a* and a second longitudinal side edge 113*b* and defines first and second opposing end regions 108*a*, 108*b* and a central region 108*c*. As measured in an extended state, the distance between the first longitudinal side edge 111*a* and the second longitudinal side edge 111*b* defines the pitch length, PL, of the first elastic belt 106, and the distance between the first longitudinal side edge 113*a* and the second longitudinal side edge 113*b* defines the pitch length, PL, of the second elastic belt 108. The central region 106*c* of the first elastic belt is connected with the first waist region 116 or first end region 116*a* of the chassis 102, and the central region 108*c* of the second elastic belt 108 is connected with the second waist region 118 or second end region 118*a* of the chassis 102. As shown in FIG. 1, the first end region 106*a* of the first elastic belt 106 is connected with the first end region 108*a* of the second elastic belt 108 at first side seam 178, and the second end region 106*b* of the first elastic belt 106 is connected with the second end region 108*b* of the second elastic belt 108 at second side seam 180 to define the ring-like elastic belt 104 as well as the waist opening 110 and leg openings 112. It is to be appreciated that the first belt 106 and the second belt 108 may be permanently or refastenably connected with each other at the first side seam 178 and the second side seam 180. The side seams 178, 180 may comprise a permanent bond, such as a thermal, pressure, or adhesive bond, or may be a releasable bond, such as a mechanical or cohesive fastener.

As shown in FIGS. 2A and 2B, the first elastic belt 106 also defines an outer laterally extending edge 107*a* and an inner laterally extending edge 107*b*, and the second elastic belt 108 defines an outer laterally extending edge 109*a* and an inner laterally extending edge 109*b*. The outer edge 107*a* of the first belt 106 is positioned longitudinally outward of the inner edge 107*b*, and the outer edge 109*a* of the second belt 108 is positioned longitudinally outward of the inner edge 109*b*. As such, as shown in FIG. 1, a perimeter edge 112*a* of one leg opening may be defined by portions of the inner laterally extending edge 107*b* of the first elastic belt 106, the inner laterally extending edge 109*b* of the second elastic belt 108, and the first longitudinal or right side edge 128 of the chassis 102. And a perimeter edge 112*b* of the other leg opening may be defined by portions of the inner laterally extending edge 107*b*, the inner laterally extending edge 109*b*, and the second longitudinal or left side edge 130 of the chassis 102. The outer laterally extending edges 107*a*, 109*a* may also define the front waist edge 121 and the laterally extending back waist edge 122 of the diaper pant MP.

It is to be appreciated that the first elastic belt 106 and the second elastic belt 108 may define different sizes and shapes. In some configurations, the first elastic belt 106 and/or second elastic belt 108 may define curved contours. For example, the inner lateral edges 107*b*, 109*b* of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168 that extend along non-linear or curved paths that may correspond with the curved contours of the inner lateral edges 107*b*, 109*b*.

Figure 2C:
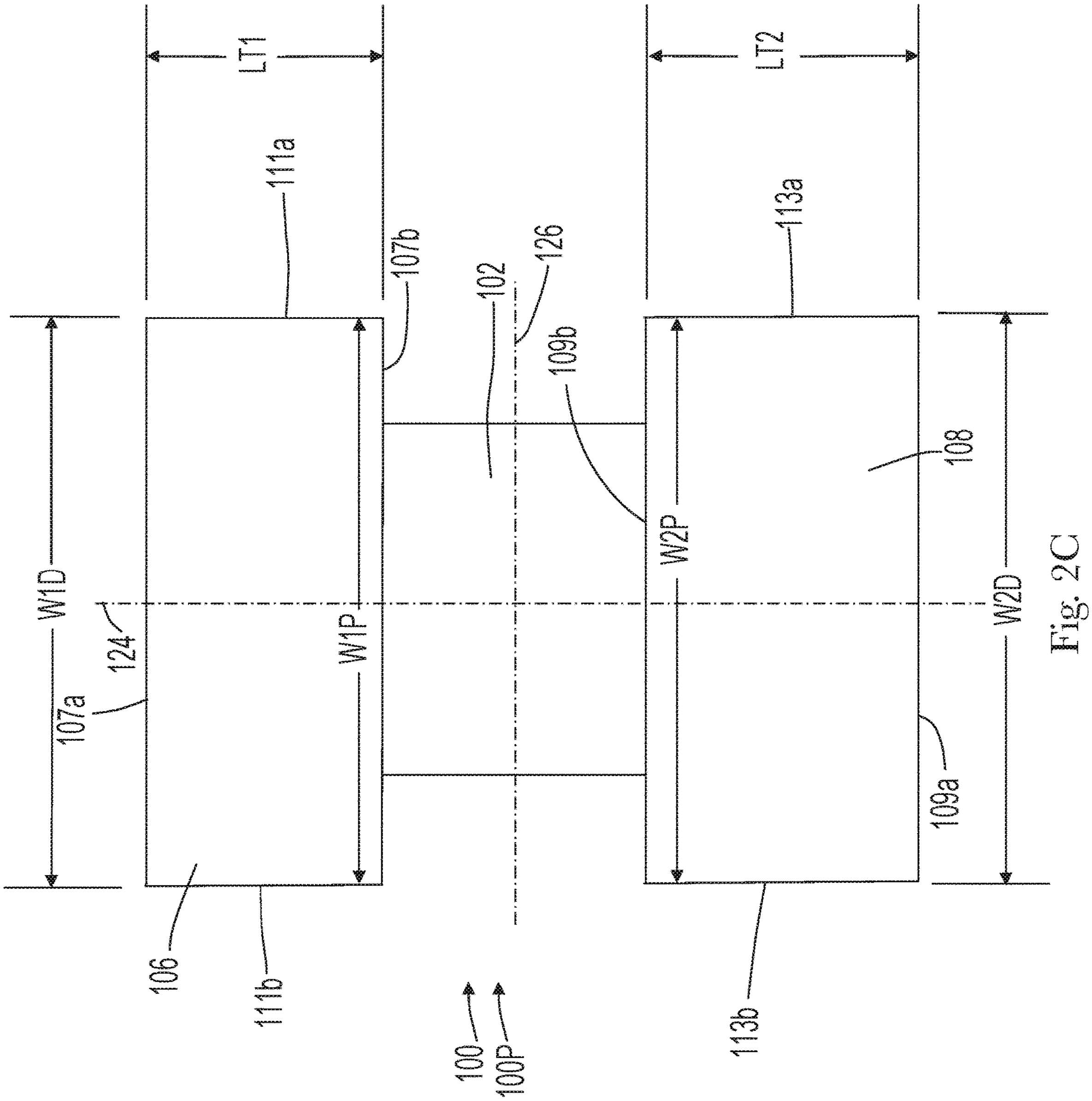
FIG. 2C shows a plan view of a diaper pant with the portion of the diaper that faces away from a wearer oriented toward the viewer, illustrating first and second belt size and shape features.

FIG. 2C shows a configuration wherein the first elastic belt 106 and the second elastic belt 108 both define generally rectangular shapes. For example, as shown in FIG. 2C, the outer laterally extending edge 107*a* of the first elastic belt 106 may comprise a lateral width of W1D and the inner laterally extending edge 107*b* may comprise a lateral width of W1P, wherein W1D and W1P are equal or substantially equal. In addition, the outer laterally extending edge 109*a* of the second elastic belt 108 may comprise a lateral width of W2D and the inner laterally extending edge 109*b* may comprise a lateral width of W2P, wherein W2D and W2P are equal or substantially equal.

Figure 2D:
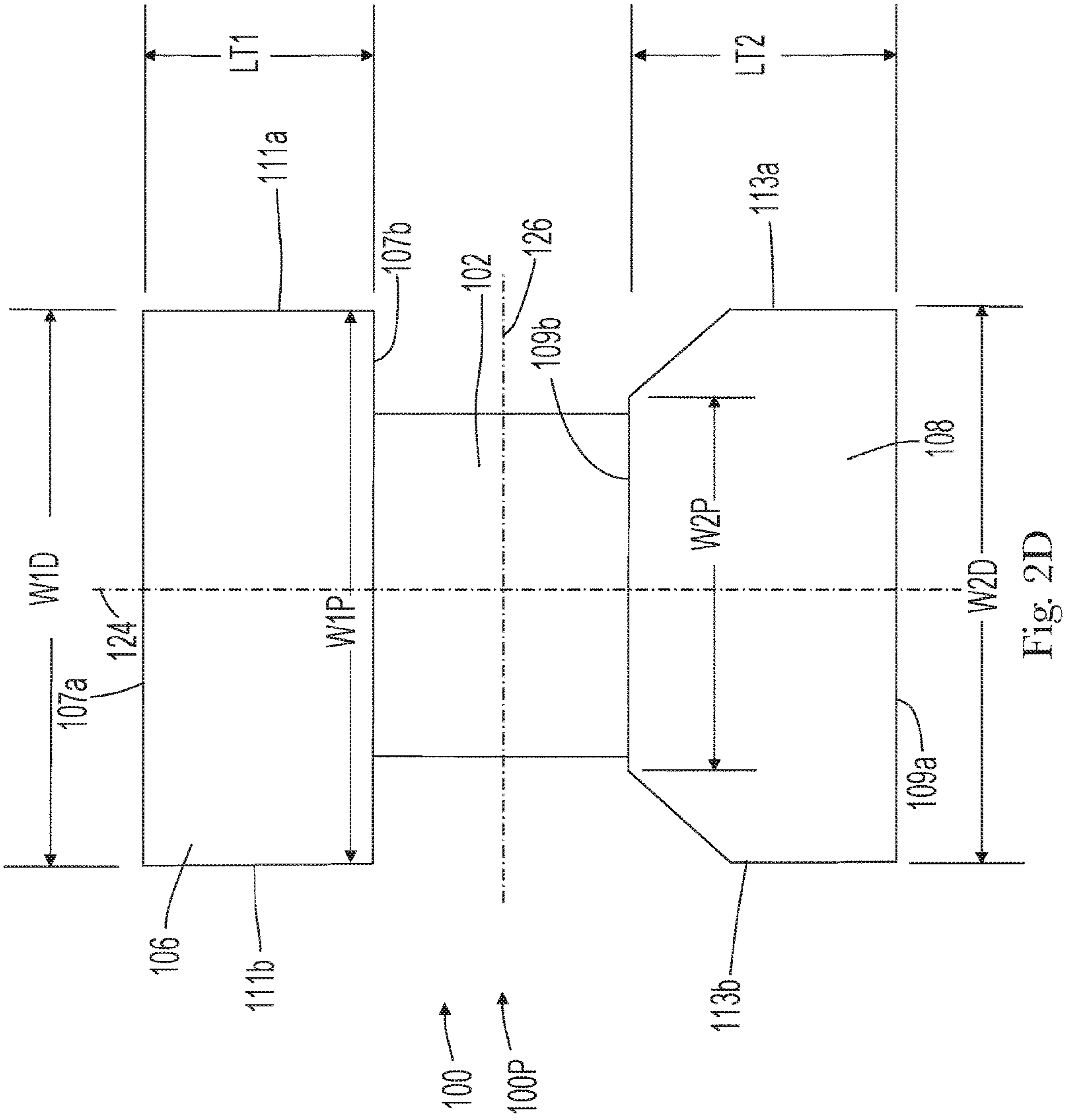
FIG. 2D shows a plan view of a diaper pant with the portion of the diaper that faces away from a wearer oriented toward the viewer, illustrating first and second belt size and shape features.

In some configurations, at least one of the first elastic belt 106 and the second elastic belt 108 may comprise lateral edges having different lengths. For example, FIG. 2D shows a configuration wherein the first elastic belt 106 defines a generally rectangular shape, such as described with reference to FIG. 2C, and wherein the outer laterally extending edge 109*a* of the second elastic belt 108 and the inner laterally extending edge 109*b* have different lengths. As shown in FIG. 2D, the outer laterally extending edge 109*a* of the second elastic belt 108 may comprise a lateral width of W2D and the inner laterally extending edge 109*b* may comprise a lateral width of W2P, wherein W2D is greater than W2P.

Figure 2E:
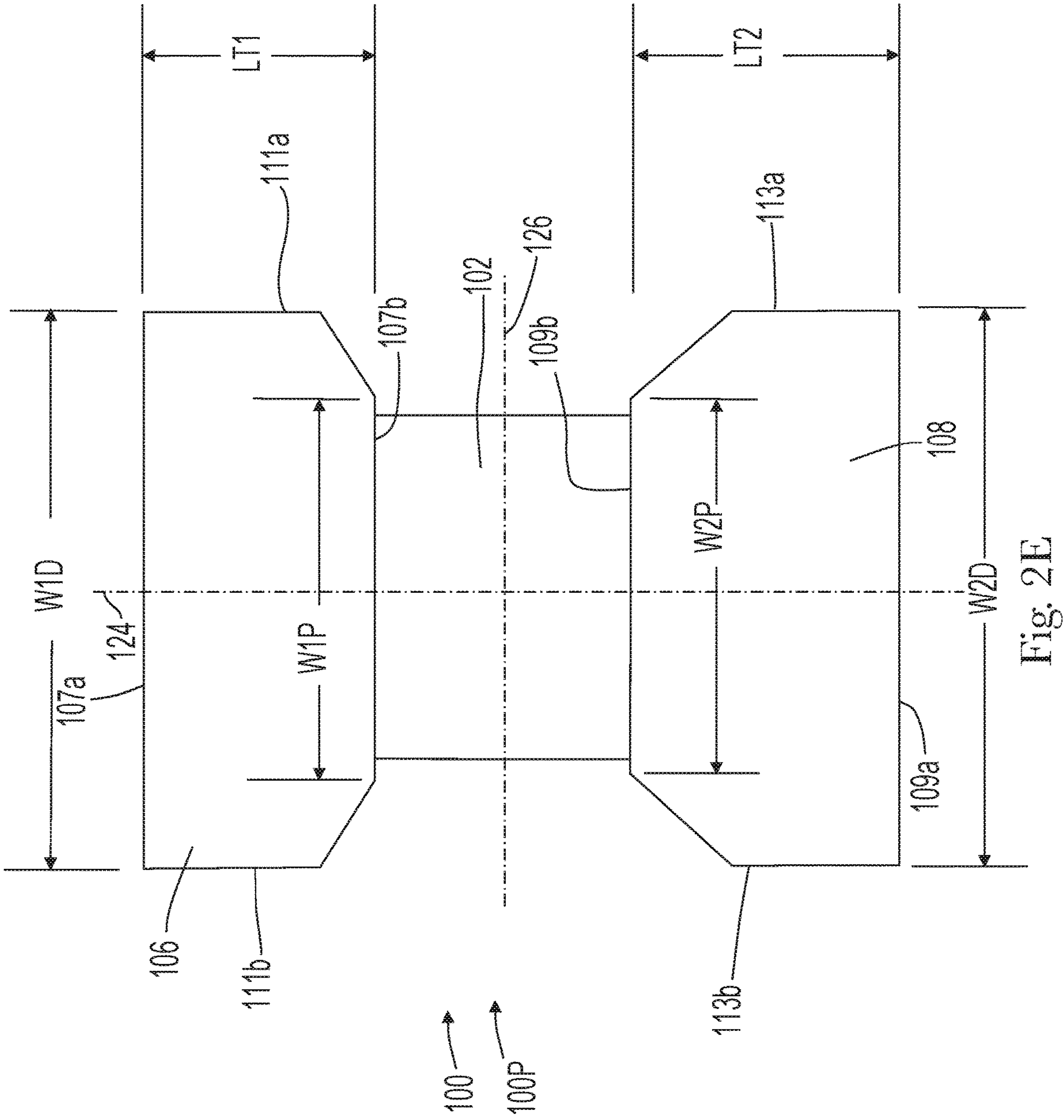
FIG. 2E shows a plan view of a diaper pant with the portion of the diaper that faces away from a wearer oriented toward the viewer, illustrating first and second belt size and shape features.

In some configurations, both the first elastic belt 106 and the second elastic belt 108 may comprise lateral edges having different lengths. For example, FIG. 2E shows a configuration wherein the outer laterally extending edge 107*a* of the first elastic belt 106 and the inner laterally extending edge 107*b* have different lengths, and wherein the outer laterally extending edge 109*a* of the second elastic belt 108 and the inner laterally extending edge 109*b* have different lengths. As shown in FIG. 2E, the outer laterally extending edge 107*a* of the first elastic belt 107 may comprise a lateral width of W1D and the inner laterally extending edge 107*b* may comprise a lateral width of W1P, wherein W1D is greater than W1P, and wherein the outer laterally extending edge 109*a* of the second elastic belt 108 may comprise a lateral width of W2D and the inner laterally extending edge 109*b* may comprise a lateral width of W2P, wherein W2D is greater than W2P.

With reference to FIGS. 2C-2E, the first elastic belt 106 may define a longitudinal length LT1 extending between outer laterally extending edge 107*a* and the inner laterally extending edge 107*b*, and the second elastic belt 108 may define a longitudinal length LT2 extending between outer laterally extending edge 109*a* and the inner laterally extending edge 109*b*. In some configurations, LT1 may be equal to LT2. In some configurations, LT1 may be less or greater than LT2. With continued reference to FIGS. 2C-2E, in some configurations, W1D may be equal to W1P, or W1D may be different than W1P. In some configurations, W2D may be equal to W2P, or W2D may be different than W2P. In some configurations, W1D and/or W1P may be equal to or different W2D and/or W2P.

Figure 3:
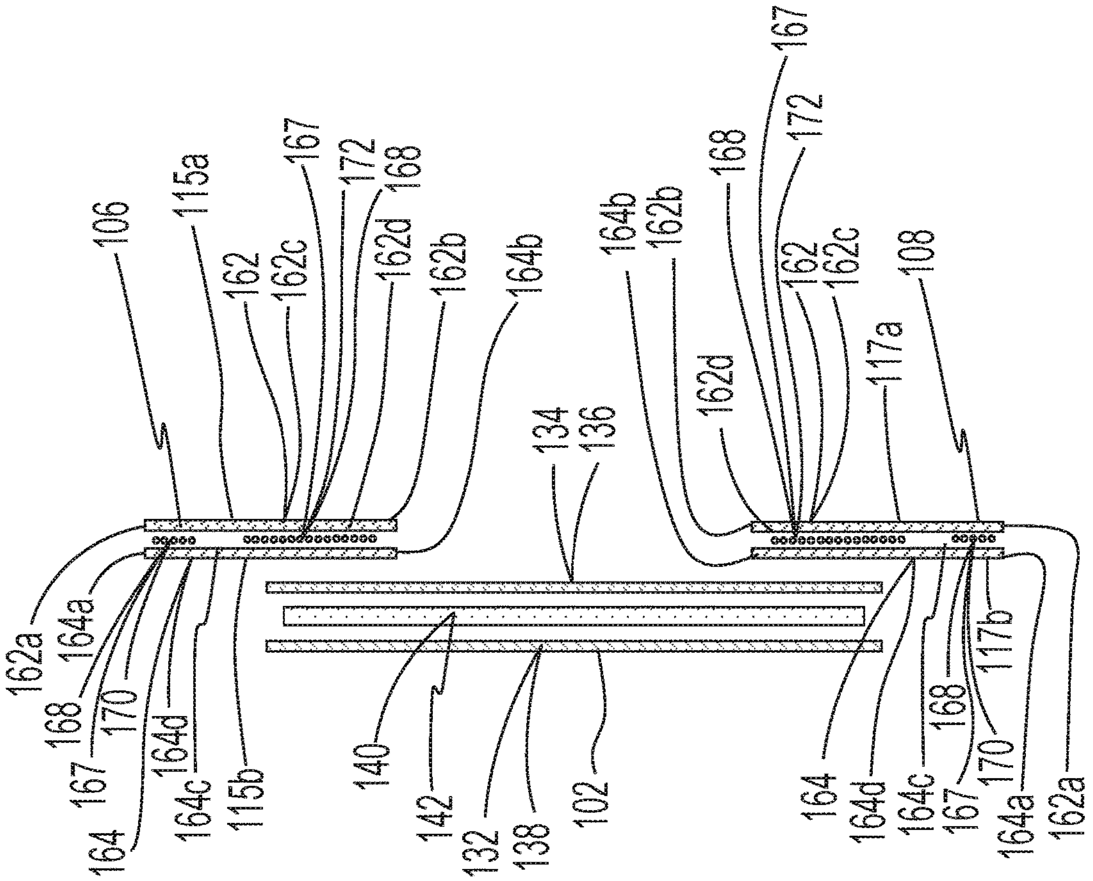
FIG. 3 is a cross-sectional view of the diaper pant of FIG. 2A taken along line 3-3 showing first and second elastic belts provided with panel layers.

With reference to FIGS. 2A, 2B, and 3, the first elastic belt 106 and the second elastic belt 108 may also each include a first substrate 162 and a second substrate 164. The first substrates 162 may be oriented to define at least a portion of a garment facing surface 115*a* of the first elastic belt 106 and a garment facing surface 117*a* the second elastic belt 108, and the second substrates 164 may be oriented to define at least a portion of a wearer facing surface 115*b* of the first elastic belt 106 and a wearer facing surface 117*b* of the second elastic belt 108. The first substrate 162 may extend from a proximal edge 162*b* to a distal edge 162*a* for a maximum length L1, and the second substrate 164 may extend from a proximal edge 164*b* to a distal edge 164*a* for a maximum length L2. It is to be appreciated that the distal edge 162*a* and/or the proximal edge 162*b* of the first substrate 162 may be straight and/or curved and/or may be parallel or unparallel to each other. It is also to be appreciated that the distal edge 164*a* and/or the proximal edge 164*b* of the second substrate 164 may be straight and/or curved and/or may be parallel or unparallel to each other. As such, the maximum length L1 refers to the longest distance extending longitudinally between the distal edge 162*a* and the proximal edge 162*b* of the first substrate 162, and the maximum length L2 refers to the longest distance extending longitudinally between the distal edge 164*a* and the proximal edge 164*b* of the second substrate 164. In some configurations, L1 may be equal to, less than, or greater than L2. In some configurations, L1 may be equal to or less than LT1, and L2 may be equal to or less than LT2. In some configurations, the distal edge 162*a* of the first substrate 162 may define at least a portion of the front waist edge 121 and/or at least a portion of back waist edge 122, and/or the distal edge 164*a* of the second substrate 164 may define at least a portion of the front waist edge 121 and/or at least a portion of back waist edge 122. As such, in some configurations, the distal edge 162*a* of the first substrate 162 and/or the distal edge 164*a* of the second substrate 164 may define at least a portion of the waist opening 110.

Figure 1A:
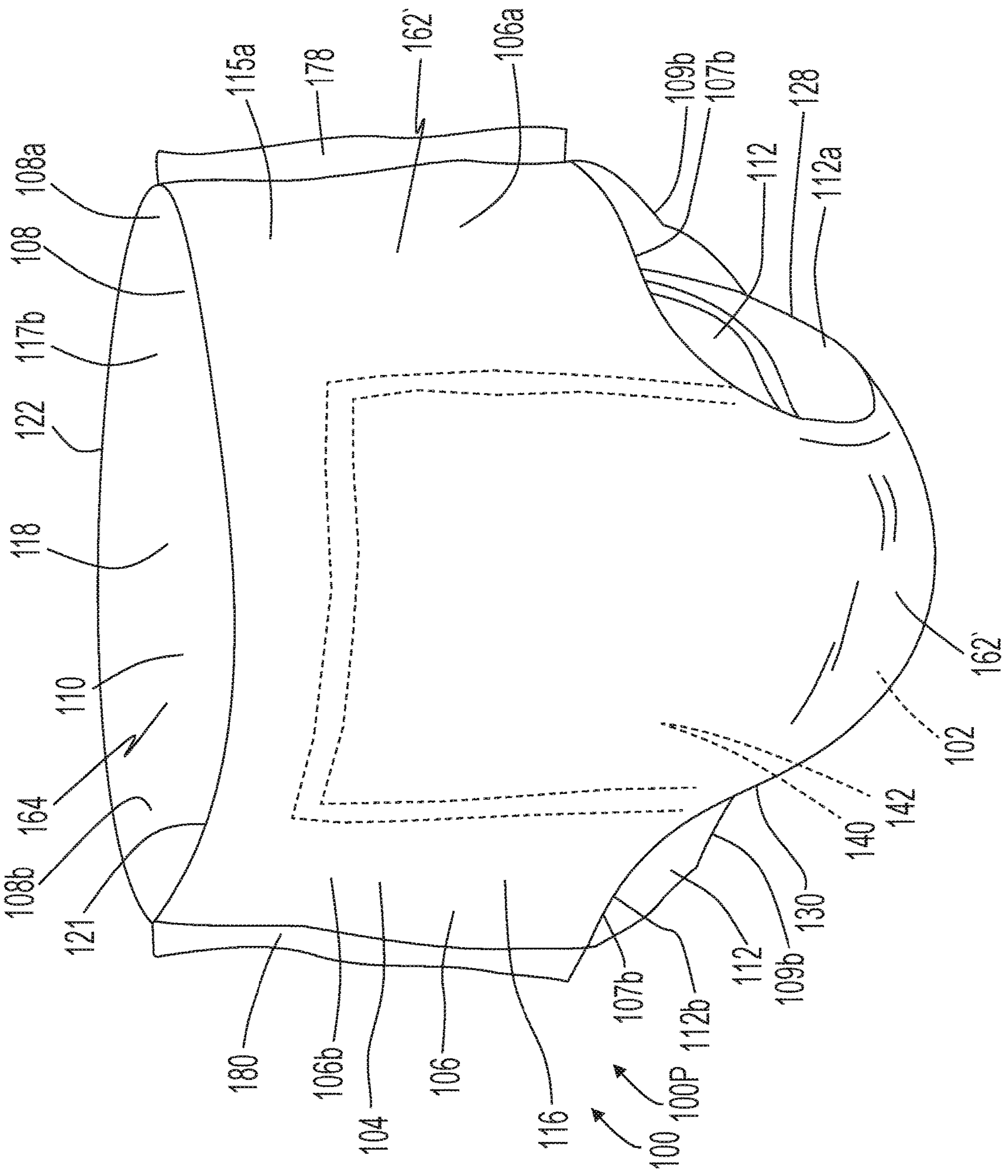
FIG. 1A shows a perspective view of a diaper pant with a continuous outer cover in a pre-fastened configuration.
Figure 2F:
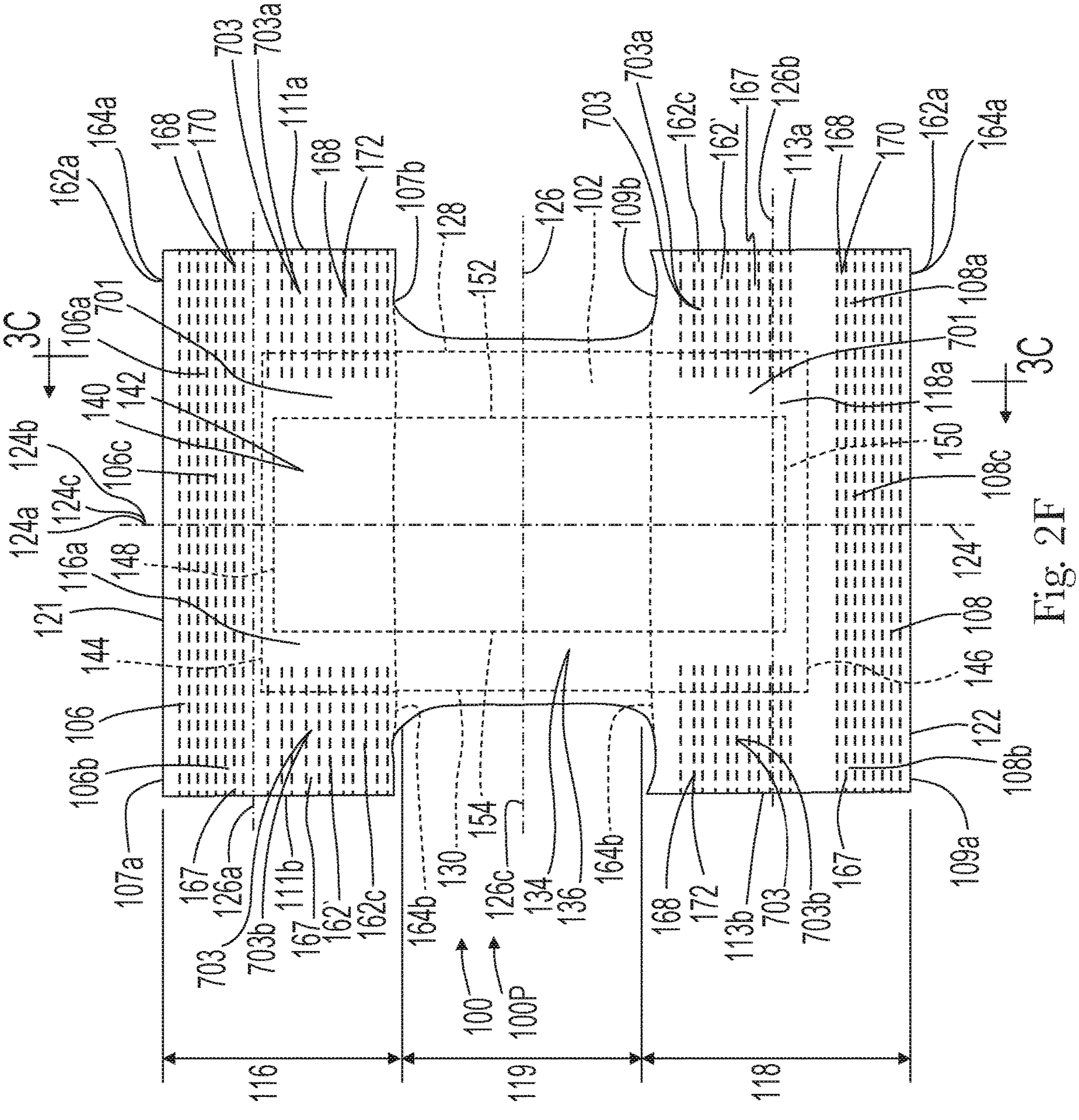
FIG. 2F shows a plan view of a diaper pant with a continuous outer cover with the portion of the diaper that faces away from a wearer oriented toward the viewer.
Figure 3A:
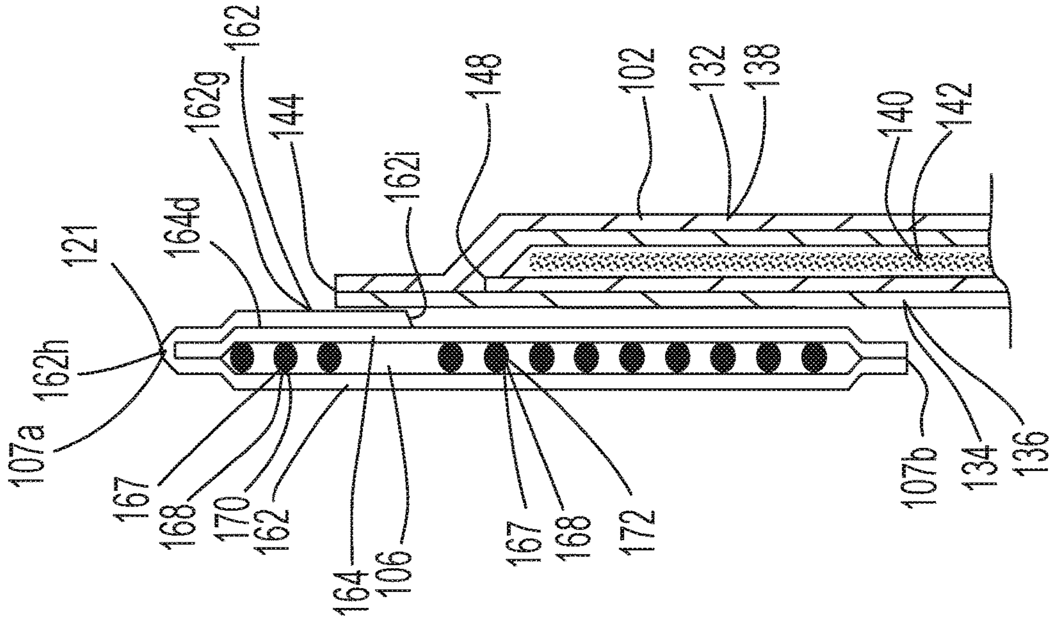
FIG. 3A is a cross-sectional detailed view of a first belt provided with panel layers wherein one panel layer is folded over another panel layer.
Figure 3A:
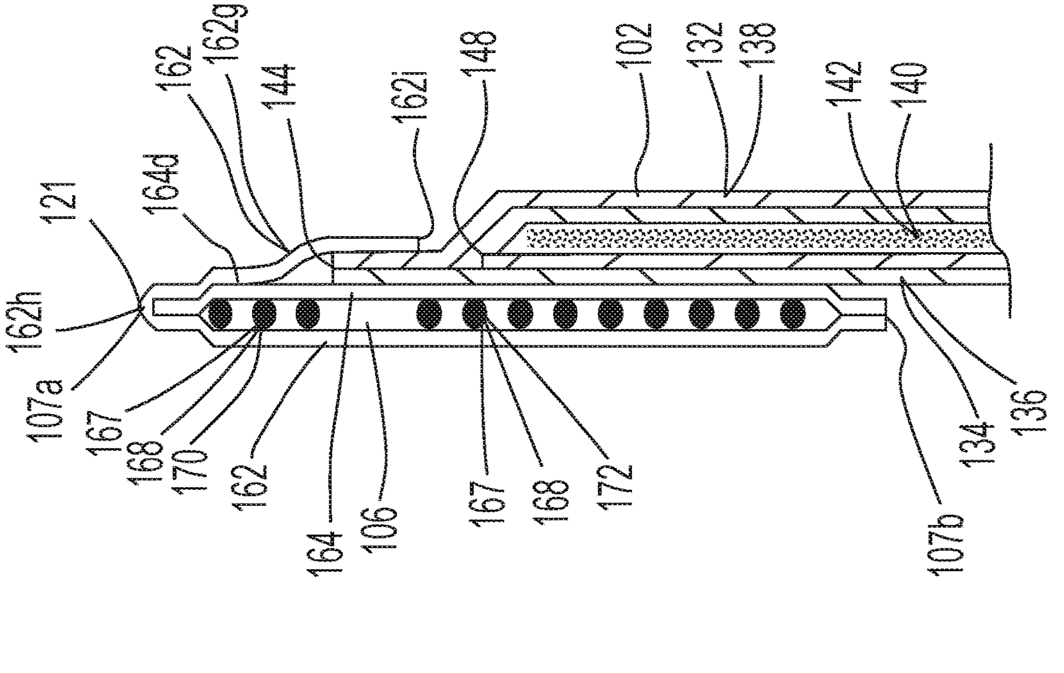
Figure 3B:
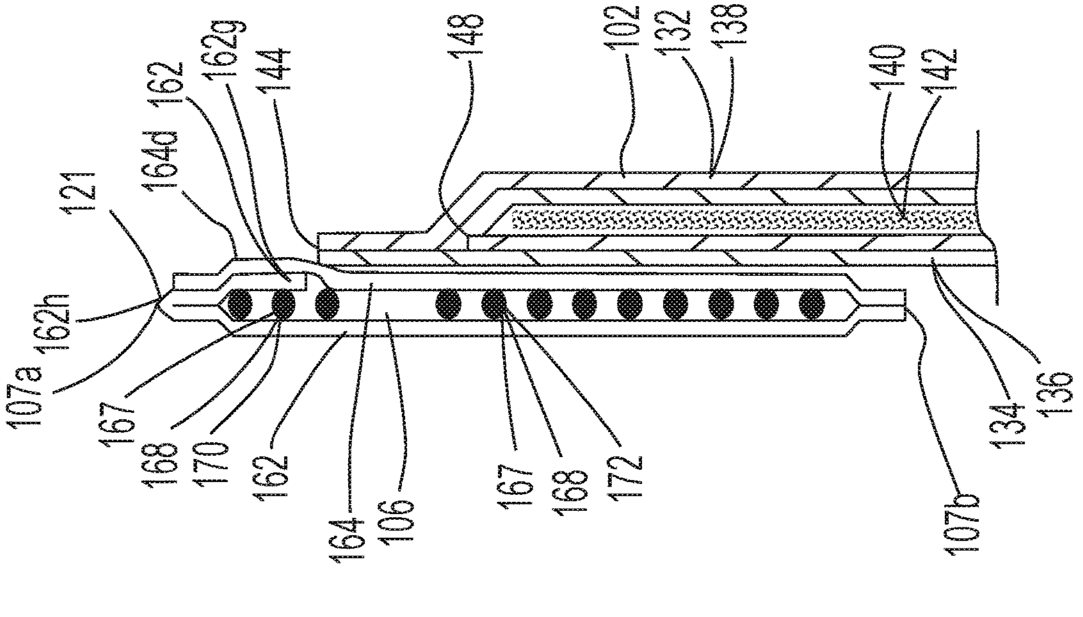
FIG. 3B is a cross-sectional detailed view of a second belt provided with panel layers wherein one panel layer is folded over another panel layer.
Figure 3B:
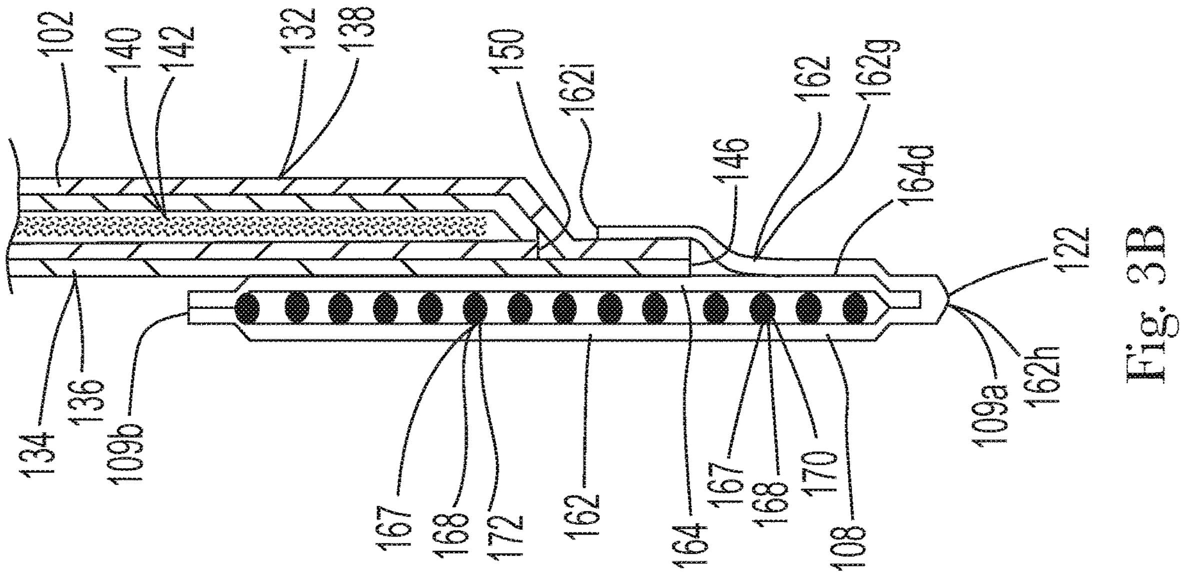
Figure 3C:
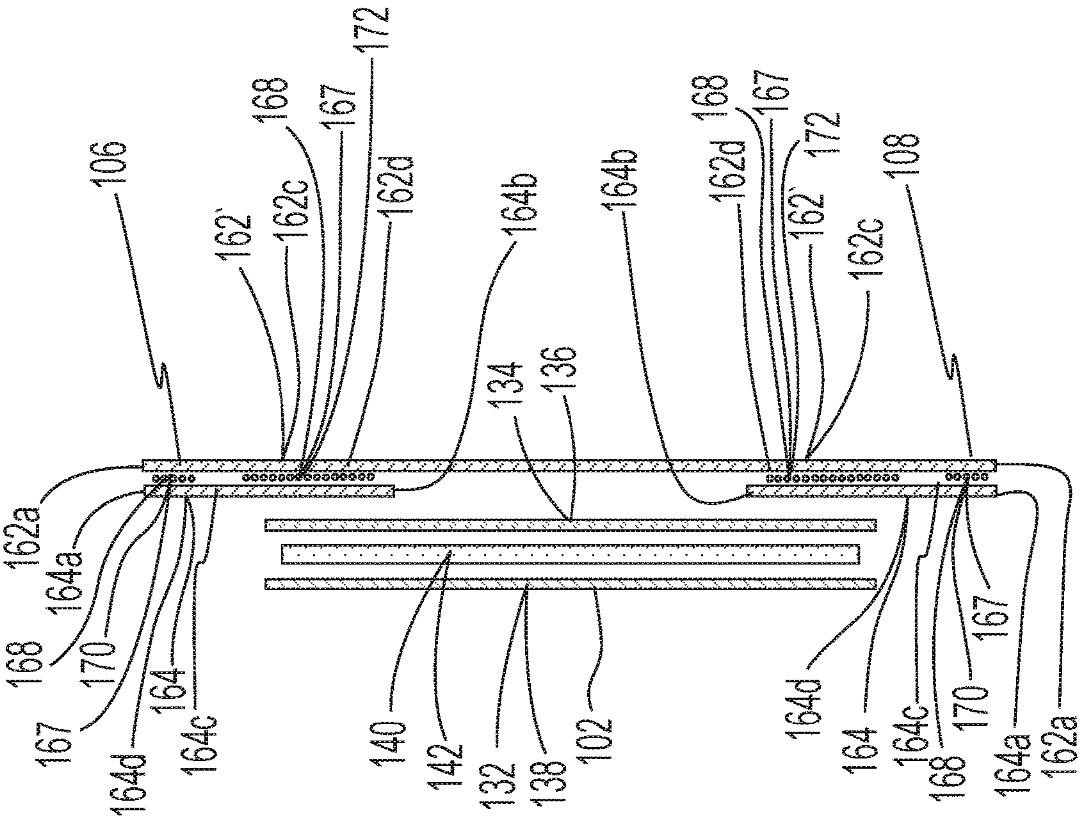
FIG. 3C is a cross-sectional view of the diaper pant of FIG. 2F taken along line 3C-3C showing first and second elastic belts provided with panel layers and a continuous outer cover.

It is also to be appreciated that the first substrate 162 and/or the second substrate 164 may extend continuously from the first belt 106 to the second belt 108. For example, the first substrate 162 may be configured to define a continuous outer cover 162' that extends contiguously from the first waist edge 121 to the second waist edge 122, such as shown in FIGS. 1A, 2F, and 3C. It is also to be appreciated that diaper pants 100P with continuous outer covers, such as shown in FIGS. 1A, 2F, and 3C may also be configured to include various aspects of the frangible pathways and fastener components discussed herein.

It is to be appreciated that the first substrate 162 and the second substrate 164 may define various lateral widths that may or may not be equal. For example, as shown in FIG. 2B, the first substrate 162 may extend laterally between a first longitudinal edge 162*e* and a second longitudinal edge 162*f* to define a first lateral width W1, and the second substrate 164 may extend laterally between a first longitudinal edge 164*e* and a second longitudinal edge 164*f* to define a second lateral width W2.

In some configurations, the proximal edge 162*b* of the first substrate 162 and/or the proximal edge 164*b* of the second substrate 164 may extend laterally across the backsheet 136. As shown in FIGS. 2A-3, the first substrate 162 includes a garment facing surface 162*c* and an opposing wearer facing surface 162*d*, and the second substrate 164 includes a garment facing surface 164*c* and an opposing wearer facing surface 164*d*.

In some configurations, the first elastic belt 106 and/or the second elastic belt 108 may include a folded portion of at least the first substrate 162 and/or the second substrate 164. For example, as shown in FIGS. 3A and 3B, the first elastic belt 106 and/or the second elastic belt 108 may include a folded portion 162*g* of the first substrate 162 extending longitudinally between a fold line 162*h* in the first substrate 162 and a lateral edge 162*i*. As such, the folded portion 162*g* of the first substrate 162 may be connected with the wearer facing surface 164*d* of the second substrate 164. In some configurations, the folded portion 162*g* of the first substrate 162 may also be connected with and/or overlap the chassis 102. In some configurations, the folded portion 162*g* of the first substrate 162 may also be connected with the wearer facing surface 162*d* of the first substrate 162. In some configurations, a portion of the folded portion 162*g* of the first substrate 162 may be left unbonded to the chassis 102 and/or the second substrate 164, forming a pocket having an opening oriented toward the lateral centerline 162*c* of the chassis 102. In another example, the first elastic belt 106 and/or the second elastic belt 108 may include a folded portion of the second substrate 164 extending longitudinally between a fold line in the second substrate 164 and a lateral edge. As such, the folded portion of the second substrate 164 may be connected with the garment facing surface 162*c* of the first substrate 162. As such, in some configurations, a fold line of the first substrate 162 and/or a fold line of the second substrate 164 may define at least a portion of the waist opening 110. It is to be appreciated that various waist configurations may be utilized. For example, as shown in FIG. 3A1, the folded portion 162*g* may be sandwiched between the second substrate 164 and the backsheet 136. In another example shown in FIG. 3A2, the second substrate 164 may be sandwiched between the folded portion 162*g* and the backsheet 136. Although FIGS. 3A1 and 3A2 show configurations of the first belt 106, it is to be appreciated that such configurations may be applied with the second belt 108.

It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that components of the first elastic belt 106 and the second elastic belt 108, such as the first substrate 162, and/or second substrate 164 may be constructed from various materials. For example, the first and/or second belts may include a first substrate 162, and/or second substrate 164 that may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some configurations, the first and/or second belts may include a first substrate 162, and/or second substrate 164 comprising a nonwoven web of synthetic fibers, and may include a stretchable nonwoven. In some configurations, the first and second elastic belts may include an inner hydrophobic, non-stretchable nonwoven material and an outer hydrophobic, non-stretchable nonwoven material. It is to be appreciated that the belts may configured in various ways, such as disclosed for example, in U.S. Patent Publication No. US2022/0142828A1 and Chinese Patent Application No. CN2021/077843, which are both incorporated by reference.

Elastic material 167 may be positioned between the wearer facing surface 162*d* of the first substrate 162 and the garment facing surface 164*c* of the second substrate 164. It is to be appreciated that the elastic material 167 may include one or more elastic elements such as strands, ribbons, elastic films, or panels extending along the lengths of the elastic belts. As shown in FIGS. 2A and 3, the elastic material 167 may include a plurality of elastic strands 168. In some configurations, the elastic material 167 may be an elastic film used to form a zero-strain elastic laminate comprising an elastic film bonded to one or more nonwoven layers and subsequently subjected to mechanical deformation or activation sufficient to weaken the nonwoven layer(s) and enable the laminate to stretch and recover elastically.

It is also to be appreciated that the first substrate 162, second substrate 164, and/or elastic material 167 of the first elastic belt 106 and/or second elastic belt 108 may be bonded together and/or with other components, such as the chassis 102, with adhesive and/or mechanical bonds. It is to be appreciated that adhesive and mechanical bonding methods may be utilized alone or in combination with each other.

In some configurations, adhesive may be applied to at least one of the first substrate 162, second substrate 164, and/or elastic material 167 when being combined to form the first elastic belt 106 and/or second elastic belt 108. In some configurations, mechanical bonding devices may apply mechanical bonds to the to at least one of the first substrate 162, second substrate 164, and/or elastic material 167 when being combined to form the first elastic belt 106 and/or second elastic belt 108. Such mechanical bonds may be applied with heat, pressure, and/or ultrasonic devices. In some configurations, mechanical bonding devices may apply bonds that bond the first substrate 162, second substrate 164, and/or elastic material 167 together and/or may act to trap or immobilize discrete lengths of the contracted elastic strands in the first elastic belt 106 and/or second elastic belt 108.

It is also to be appreciated that the first substrate 162, second substrate 164, and/or elastic material 167 may be bonded together with various methods and apparatuses to create various elastomeric laminates, such as described in U.S. Patent Publication Nos. 2018/0168878 A1; 2018/0168877 A1; 2018/0168880 A1; 2018/0170027 A1; 2018/0169964 A1; 2018/0168879 A1; 2018/0170026 A1; 2018/0168889 A1; 2018/0168874 A1; 2018/0168875 A1; 2018/0168890 A1; 2018/0168887 A1; 2018/0168892 A1; 2018/0168876 A1; 2018/0168891 A1; 2019/0070042 A1; 2019/0070041 A1; 2021/0282797A1; and 2021/0275362 A1, all of which are incorporated herein by reference.

It is to be appreciated that components of the first elastic belt 106 and/or the second elastic belt 108 may be assembled in various ways and various combinations to create various desirable features that may differ along the lateral width and/or longitudinal length of the first elastic belt 106 and/or the second elastic belt 108. Such features may include, for example, Dtex values, bond patterns, aperture arrangements, elastic positioning, Average Dtex values, Average Pre-Strain values, rugosity frequencies, rugosity wavelengths, height values, and/or contact area. It is to be appreciated that differing features may be imparted to various components, such as for example, the first substrate 162, second substrate 164, and elastic material 167 before and/or during stages of assembly of the first elastic belt 106 and/or the second elastic belt 108.

It is to be appreciated that the first elastic belt 106 and/or the second elastic belt 108 may include various configurations of belt elastic materials 167 arranged in relation to each other and to the first substrate 162, and the second substrate 164. As discussed above, the elastic material 167 may include configurations of one or more elastic elements such as strands, ribbons, films, or panels positioned in various arrangements. In some configurations, the elastic material 167 may comprise various elastics, elastic features and arrangements, and processes for assembly, such as described in 2018/0168889 A1; 2018/0168874 A1; 2018/0168875 A1; 2018/0168890 A1; 2018/0168887 A1; 2018/0168892 A1; 2018/0168876 A1; 2018/0168891 A1; 2019/0298586 A1; 2019/0070042 A1; 2018/0168878 A1; 2018/0168877 A1; 2018/0168880 A1; 2018/0170027 A1; 2018/0169964 A1; 2018/0168879 A1; 2018/0170026 A1; 2019/0070041 A1; 2021/0282797A1; and 2021/0275362 A1, which are all incorporated by reference. It is also to be appreciated the elastic materials 167 herein may be configured with identical or different colors in various different locations on the first elastic belt 106 and/or the second elastic belt 108.

In some configurations, the elastic material 167 may be configured as elastic strands 168 disposed at a constant interval in the longitudinal direction. In other embodiments, the elastic strands 168 may be disposed at different intervals in the longitudinal direction. In some configurations, the Dtex values of the elastic strands 168 may be constant or varied along the longitudinal direction. In some configurations, the elastic material 167 in a stretched condition may be interposed and joined between uncontracted substrate layers. When the elastic material 167 is relaxed, the elastic material 167 returns to an unstretched condition and contracts the substrate layers. The elastic material 167 may provide a desired variation of contraction force in the area of the ring-like elastic belt. It is to be appreciated that the chassis 102 and elastic belts 106, 108 may be configured in different ways other than as depicted in attached Figures. It is also to be appreciated that the elastic material 167 material may be joined to the substrates continuously or intermittently along the interface between the elastic material 167 material and the substrates. In some configurations, the elastic strands 168 may be in the form of extruded elastic strands, which may also be bonded with the first substrate 162 and/or second substrate 164 in a pre-corrugated configuration, such as disclosed for example in U.S. Pat. No. 5,681,302, which is incorporated by reference herein.

As discussed above for example with reference to FIGS. 2A and 3, the elastic material 167 discussed herein may be in the form of elastic strands 168. In some configurations, the elastic strands 168 may be parallel with each other and/or with the lateral axis 126. It is to be appreciated that the first elastic belt 106 and/or second elastic belt 108 may be configured to include various quantities of elastic strands 168. In some configurations, elastic strands 168 may be grouped in pairs. In some configurations, the first elastic belt 106 and/or second elastic belt 108 may comprise from about 10 to about 1500 elastic strands 168. It is also to be appreciated that elastic strands 168 herein may comprise various Dtex values, strand spacing values, and pre-strain values and such elastic strands 168 may utilized with other elastic strands to create first and second elastic belts 106, 108 comprising elastic strands 168 in various combinations of Dtex values, strand spacing values, and pre-strain values. For example, in some configurations, the Average-Dtex of one or more elastic strands 168 may be greater than 500. In some configurations, the Average-Dtex of one or more elastic strands 168 may be from about 10 to about 1500, specifically reciting all 1 Dtex increments within the above-recited range and all ranges formed therein or thereby. In some configurations, a plurality of elastic strands 168 may comprise an Average-Strand-Spacing of less than or equal to 4 mm. In some configurations, a plurality of elastic strands 168 may comprise an Average-Strand-Spacing from about 0.25 mm to about 4 mm, specifically reciting all 0.01 mm increments within the above-recited range and all ranges formed therein or thereby. In some configurations, a plurality of elastic strands 168 may comprise an Average-Strand-Spacing of greater than 4 mm. In some configurations, the Average-Pre-Strain of each of a plurality of elastic strands may be from about 50% to about 400%, specifically reciting all 1% increments within the above-recited range and all ranges formed therein or thereby. In some configurations, the elastic strands 168 comprise an Average-Strand-Spacing from about 0.25 mm to about 4 mm and an Average-Dtex from about 10 to about 500. In some configurations, the elastic strands 168 may comprise an Average-Pre-Strain from about 75% to about 300%.

In some configurations, a first plurality of elastic strands may comprise a first Average-Pre-Strain from about 75% to about 300%, and a second plurality of elastic strands may comprise a second Average-Pre-Strain that is greater than first Average-Pre-Strain. In some configurations, a first plurality of elastic strands comprises an Average-Strand-Spacing from about 0.25 mm to about 4 mm and an Average-Dtex from about 10 to about 500; and a second plurality of elastic strands may comprise an Average-Strand-Spacing greater than about 4 mm and an Average-Dtex greater than about 450.

In some configurations, such as shown in FIG. 2A, the elastic strands 168 may be referred to herein as outer waist elastics 170 and inner waist elastics 172. Elastic strands 168, such as the outer waist elastics 170, may continuously extend laterally between the first and second opposing end regions **106*a*, 106*b* of the first elastic belt 106 and between the first and second opposing end regions 108*a*, 108*b* of the second elastic belt 108. Some elastic strands 168, such as the inner waist elastics 172, may be configured with discontinuities in areas, such as for example, where the first and second elastic belts 106, 108 overlap portions of the chassis 102, such as the absorbent assembly 140**.

As shown in FIG. 2A, the first elastic belt 106 and/or the second elastic belt 108 may be configured with low-stretch zones 701 and high-stretch zones 703. The first elastic belt 106 and/or the second elastic belt 108 may include a first high-stretch zone **703*a* and a second high-stretch zone 703*b* separated laterally by a low-stretch zone 701. Portions of the chassis 102, such as the backsheet 136 and absorbent assembly 140, may be connected with the first elastic belt 106 and/or the second elastic belt 108 in the low-stretch zones 701 in the first waist region 116 and/or the second waist region 118. The high-stretch zones 703 are elasticated by the elastic material 167, such as the elastic strands 168, 172; and the low-stretch zones 701 may comprise cut lines separating the elastic material 167, such as the elastic strands 168, 172, In some configurations, the elastic material 167 may be cut in an unbonded region where the elastic material is not bonded with first substrate 162 and the second substrate 164. Thus, the elastic material 167 retracts from the unbonded region and form low-stretch zone 701. In some configurations, the elastic material 167 may be cut into several discrete pieces. In turn, the low-stretch zones 701** define regions of the first elastic belt 106 and/or the second elastic belt 108 that have relatively less elasticity than the high-stretch zones 703. The discrete elastic material 167 that has been cut and which are elastically contracted do not add any substantial amount of elastication to the low-stretch zone 701. As such, upon application of a force, the high-stretch zones 703 will elongate more than the low-stretch zones 701. As provided above, the terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. In some configurations, the first elastic belt 106 and/or the second elastic belt 108 may be configured with high-stretch zones 703 that are elastic and may be configured with low-stretch zones 701 that are not elastic or "inelastic."

Figure 4B:
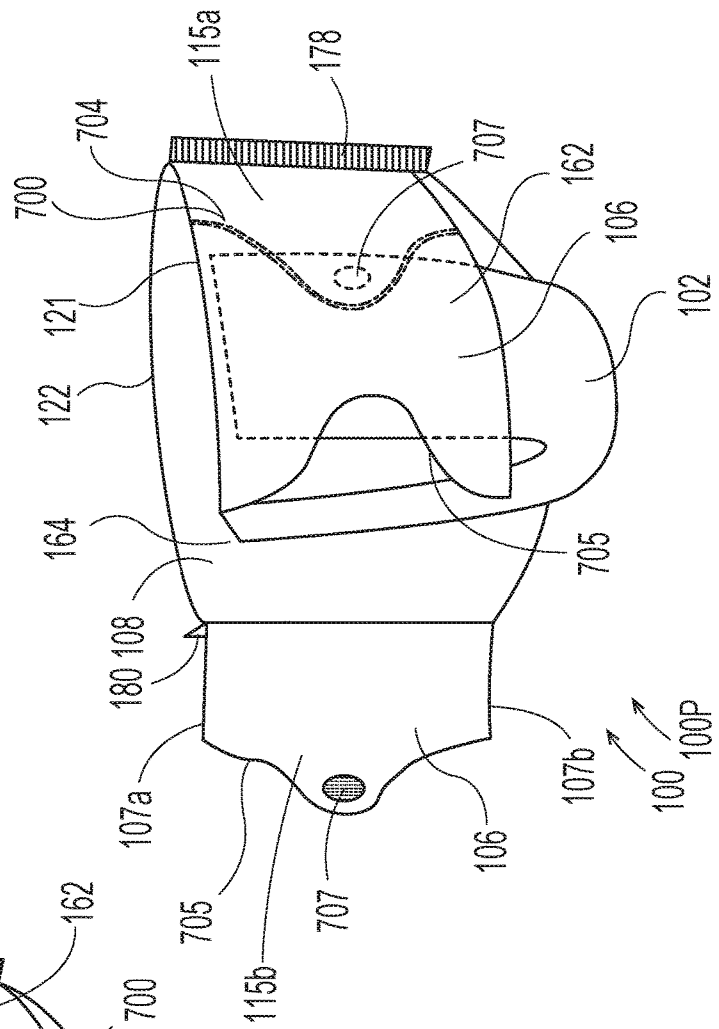
FIG. 4B is a perspective view of the diaper pant of FIG. 4A showing the front belt having been torn along one of the frangible pathways.
Figure 4A:
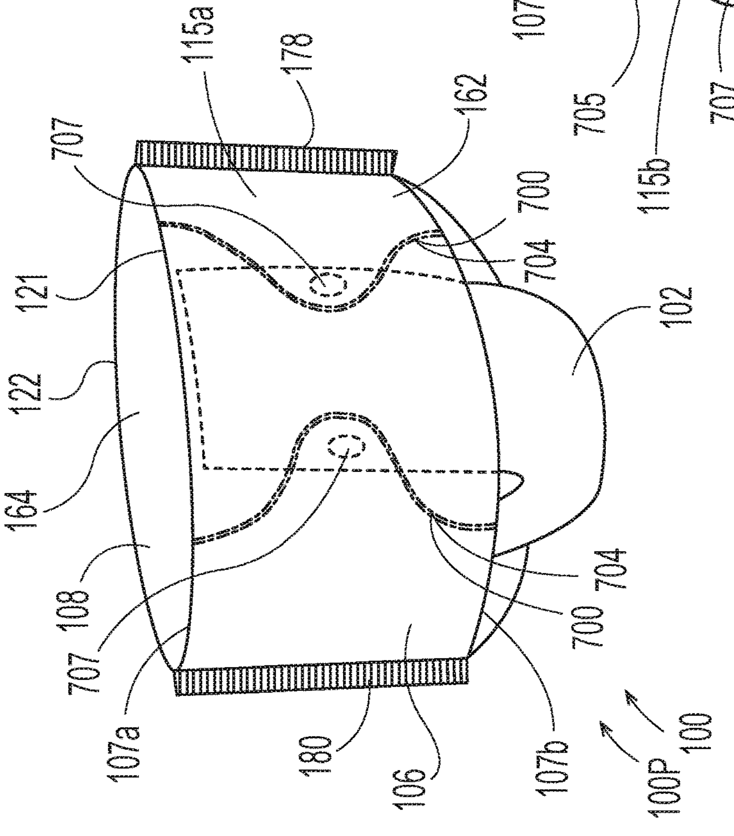
FIG. 4A is perspective view of a diaper pant including frangible pathways in a front belt and adjacent an absorbent chassis.
Figure 4C:
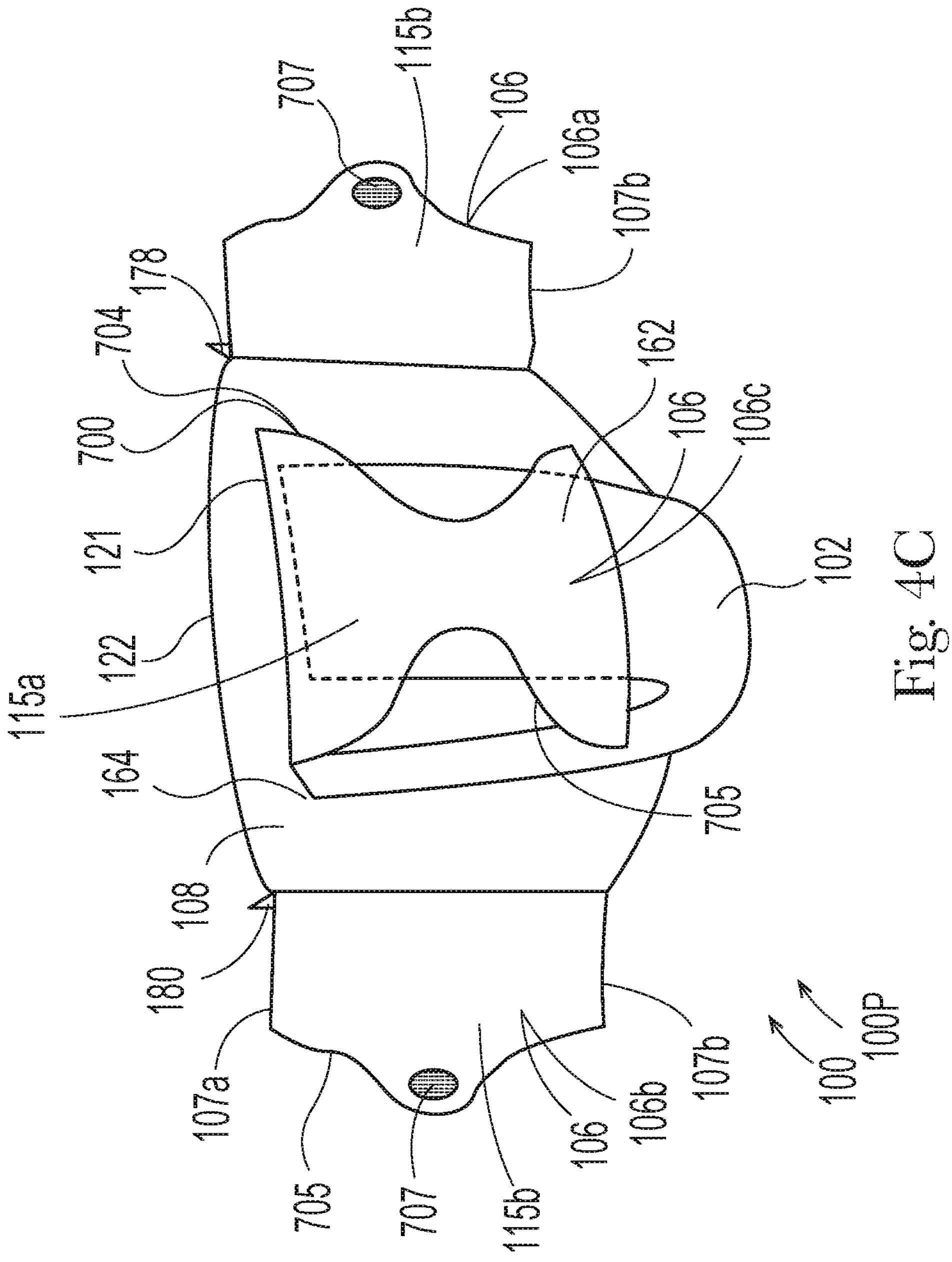
FIG. 4C is a perspective view of the diaper pant of FIG. 4A showing the front belt having been torn along two frangible pathways.

As discussed above, the diaper pants 100P described with reference to FIGS. 1-3C may include one or more frangible pathways in the first belt 106 and/or the second belt 108. For example, FIGS. 4A-4C show an example diaper pant 100P with a first belt 106 that includes frangible pathways 700. The frangible pathways 700 may be configured to allow the first elastic belt 106 to be relatively easily torn along the frangible pathway 700, such as when removing the diaper pant 100P from a wearer. FIG. 4B shows a view of the diaper pant 100P from FIG. 4A, illustrating the first belt 106 after having been torn along the frangible pathway 700 through both the outer longitudinal outer laterally extending edge 107*a* and the inner laterally extending edge 107*b* of the first belt 106. As such, the first elastic belt 106 shown in FIG. 4B is separated by opposing tear lines 705. It is to be appreciated the first elastic belt 106 may be torn along both frangible pathways 700 in FIG. 4B. For example, FIG. 4C shows the diaper pant of FIG. 4A showing the front belt having been torn along two frangible pathways 700. As shown in FIG. 4C, the central region 106*c* of the first elastic belt 106 may remain bonded with the chassis 102 after separating the first and second opposing end regions 106*a*, 106*b* from the central region 106*c* by tearing the elastic belt 106 along the frangible pathways 700.

As discussed in more detail below, the frangible pathways 700 comprise a plurality of lines of weakness 704 configured such that all elastic strands 168 in the first elastic belt 106 are severed at least once in the frangible pathway 700. Severing the elastic strands 168 in the frangible pathway 700 helps make it relatively easier to tear the first elastic, belt 106 along the frangible pathway 700. For example, when the elastic strands 168 are severed, the first substrate 162 and second substrate 164 of the first elastic belt 106 need only need to be torn without having to also tear uncut elastic strands 168. It is to be appreciated that the diaper pant 100P may include various quantities of frangible pathways 700 that may be: positioned in various locations; define various shapes; and extend for various lengths. For example, the first elastic belt 106 may comprise a first belt length defined by a longitudinal distance between the proximal edge 107*b* and the distal edge 107*a*, and the frangible pathway 700 may extend for a total length from an outermost edge of a line of weakness 704 nearest the proximal edge 107*b* of the first belt 106 to an outermost edge of a line of weakness 704 nearest the distal edge 107*a* of the first belt 106. In some configurations, the frangible pathway 700 may extend for a total length that is greater than, equal to, or less than the first belt length. In some configurations, the lines of weakness 704 may extend for a length from a first end to a second end, and a sum of the all the lengths of lines of weakness 704 in the frangible pathway 700 may be greater than the frangible pathway total length.

In some configurations, diaper pants 100P may be configured such that one or both of the first elastic belt 106 and the second elastic belt 108 include one or more frangible pathways 700. The frangible pathways 700 may be positioned in various locations on the first and second elastic belts 106, 108. For example, such as shown in FIGS. 4A-4C, frangible pathways 700 may extend to overlap with the chassis 102. In some configurations, the frangible pathways 700 may extend in straight lines and/or may be curved and/or have curved portions. In some configurations, the frangible pathways 700 may extend longitudinally for the entire length or less than the entire length of the first belt 106 and/or second belt 108. In some configurations, frangible pathways 700 may be positioned partially or entirely laterally between the first and second side seams 178, 180 and the chassis 102.

Figure 5A:
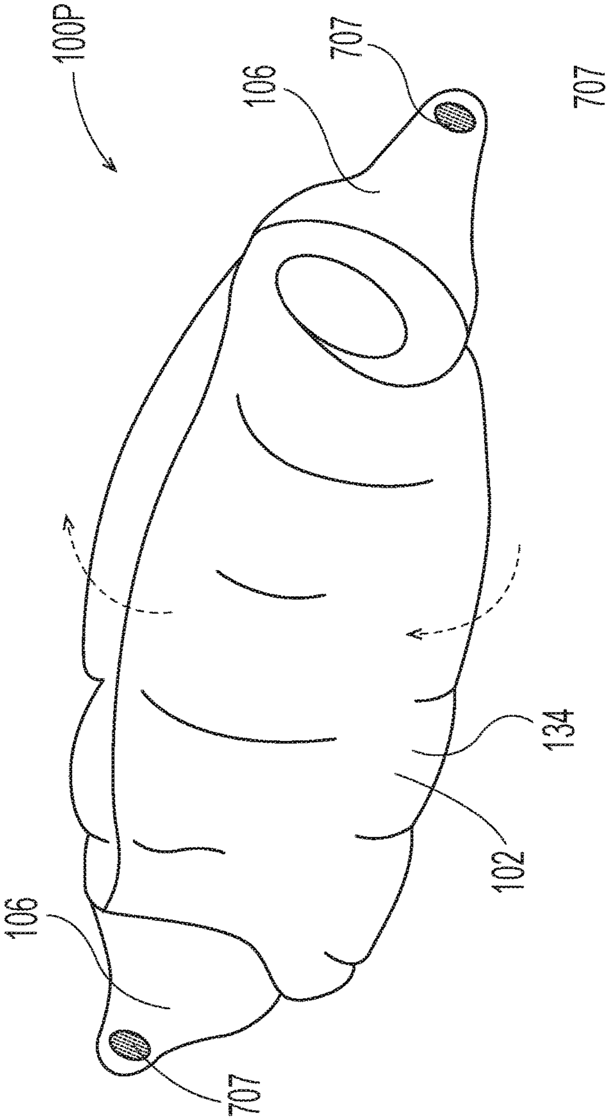
FIG. 5A shows the diaper pant of FIG. 4C being rolled up onto itself in a longitudinal direction.
Figure 5B:
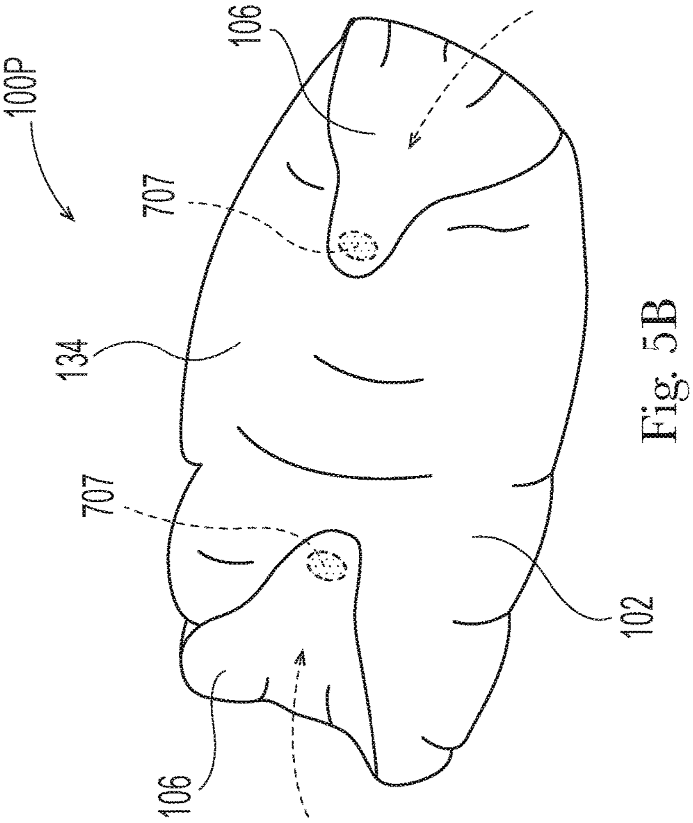
FIG. 5B shows the diaper pant of FIG. 5A with fastener components connected with the backsheet of the chassis to maintain the diaper pant in a disposal configuration.

In some configurations, the frangible pathways 700 may be configured and/or positioned to provide access to and/or function with other features, such as disposal features. For example, the diaper pant 100P shown in FIGS. 4A-4C includes fastener components 707 positioned on the wearing facing surface 115*b* of the first elastic belt 106. In some configurations, the fastener components 707 may be positioned between the first elastic belt 106 and the chassis 102. The fastener component 707 may be configured to refastenable connect with other portions of the diaper pant 100P, such as for example, the garment facing surfaces of the first elastic belt 106, the second elastic belt 108, or the chassis 102. As such, once the first elastic belt 106 is torn along the frangible pathways 700, the diaper pant 100P may be removed from a wearer and rolled or folded up for disposal, and the fastener component 707 may be connected with another portion of the diaper pant 100P to help maintain the diaper pant 100P in a disposal configuration. For example, FIG. 4C shows a diaper pant 100P after tearing the first elastic belt 106 along two frangible pathways. FIG. 5A shows the diaper pant 100P of FIG. 4C with the chassis 102 being rolled up onto itself in a longitudinal direction. And FIG. 5B shows the diaper pant 100P of FIG. 5A with fastener components 707 refastenably connected with the backsheet 136 of the chassis 102 to maintain the diaper pant 100P in a disposal configuration. In some configurations, when tearing the elastic belt along the frangible pathway 700, the tearing process may begin by tearing from the outer edge 107*a* or the inner edge 107*h* of the elastic belt 106. As discussed in more detail below, in some configurations, the first elastic belt 106 may also include an opening, such as a slit located adjacent to or in the proximity of the fastener component 707 and the weakened region 700 to help facilitate starting to tear the frangible pathway 700 in a region of the elastic belt 106 longitudinally between the outer edge 107*a* and the inner edge 107*b*.

It is also to be appreciated that the fastener component 707 may be configured in various ways, such as hooks, loops, and/or adhesive. For example, the fastener component 707 may comprise hook elements or adhesive adapted to refastenably connect with another surface of the diaper pant 100P. In some configurations, the fastener component 707 may comprise loop elements adapted to refastenably connect with hook surface on the diaper pant 100P. The fastener component 707 may be a separate element connected with the elastic belt 106 in various ways, such as mechanical bonding, adhesive bonding, or both. In some configurations, the fastener component 707 may be integrally formed from materials of the elastic belt 106, 108. In some configurations, the fastener component 707 may be printed and/or comprise materials of various different colors such that the fastener component 707 may be visible from outside the diaper pant 100P.

As previously mentioned, the fastener component 707 may comprise a hook material that can refastenably engage with substrates, such as nonwovens for example, on an exterior surface of the diaper pant 100P. For example, the fastener component 707 may comprise a substrate comprising hooks, with the substrate bonded to the elastic belt 106, 108, such as the second substrate 164, which may be in the form of a nonwoven. It is to be appreciated that the substrate may be bonded to the elastic belt 106, 108 in various ways, such as for example, with mechanical bonds, thermal bonds, ultrasonic bonds, and/or adhesive bonds or combinations thereof. In some configurations, hooks may be integrally formed from the second substrate 164, which may be in the form of a nonwoven. The fastener component 707 may comprise one material or a combination of two or more materials arranged in at least partially overlapping configuration. In some configurations, the fastener component 707 may comprise other fastener types as known in the art.

It is to be appreciated that the fastener component 707 may comprise any of a wide variety of shapes, including rectangles or other polygons, circles, ovals, shapes having exterior convexities or concavities or combinations thereof, or one or a plurality of lines or geometric shapes forming an array. It is to be appreciated that the fastener component 707 may comprise various sizes. For example, in some configurations, the fastener component 707 may have a lateral width of between about 5 mm and about 100 mm, specifically reciting all 0.1 mm increments within the above-recited range and all ranges formed therein or thereby. In some configurations, the fastener component 707 may have a longitudinal length of between about 10 mm and about 100 mm, specifically reciting all 0.1 mm increments within the above-recited range and all ranges formed therein or thereby. The fastener component 707 may be aligned parallel the lateral centerline 126*a*, 126*b* of the elastic belt 106, 108 or may be oriented at an angle relative the longitudinal centerline 126*a*, 126 of the elastic belt 106, 108 of between 0 and 90 degrees. The fastener component 707 may comprise an array of two or more spaced-apart fastening elements. The fastener component 707 may have a color that is visible through any layers of the elastic belt 106, 108 on which the fastener component 707 is located. The elastic belt 106, 108 and/or chassis 102 may include printing or other indicia highlighting to a caregiver the location, function, and/or usage of the fastener component 707. The bond, or bond pattern, attaching the fastener component 707 to the elastic belt 106, 108 may be visually or tactilely distinct from the surrounding belt material in order to provide the caregiver a signal or a mechanical grip advantage.

It is also to be appreciated that the frangible pathways 700 may comprise lines of weakness 704 that are: configured in various ways; positioned in various locations and orientations relative to each other; defined by various shapes; and extend for various lengths. For example, in some configurations, the lines of weakness 704 comprise discrete cut lines that penetrate through some or all the layers of the elastic belt 106. In some configurations, the lines of weakness 704 comprise discrete bonds wherein materials of the first substrate and the second substrate are fused together. In some configurations, the lines of weakness 704 may be linear, curvilinear, or have a regular or irregular geometry and may comprise one or more of a perforation, a bond, an aperture, or a mechanically thinned region of a material such as a nonwoven, or a combination thereof. It is also to be appreciated that the lines of weakness 704 can be formed with different lengths and spacings to achieve different separation forces.

As discussed above, absorbent articles 100, such as diaper pants 100P, may be configured with frangible pathways 700 comprising lines of weakness 704 arranged in various ways to help improve a caregiver's ability to remove a soiled diaper pant 100P from a wearer without having to remove a soiled diaper pant from a wearer by sliding the soiled diaper pant down the wearer's legs. As discussed above, the frangible pathways 700 may be configured to allow the first elastic belt 106 and/or the second elastic belt 108 to be relatively easily torn along the frangible pathway 700, such as when removing the diaper pant 100P from a wearer. In addition, the frangible pathways 700 may also be configured to provide access to fastener components 707 that may be used to help hold a soiled product in a disposal configuration. The following provides a discussion of example implementations of frangible pathways 700 on diaper pants 100P in the context of the above description of various details of absorbent articles 100, fastener components 707, frangible pathways 700, and lines weakness 704. It is to be appreciated that discussions of frangible pathways 700 in the first elastic belt 106 herein may also apply to frangible pathways 700 in the second elastic belt 108.

Figure 6A:
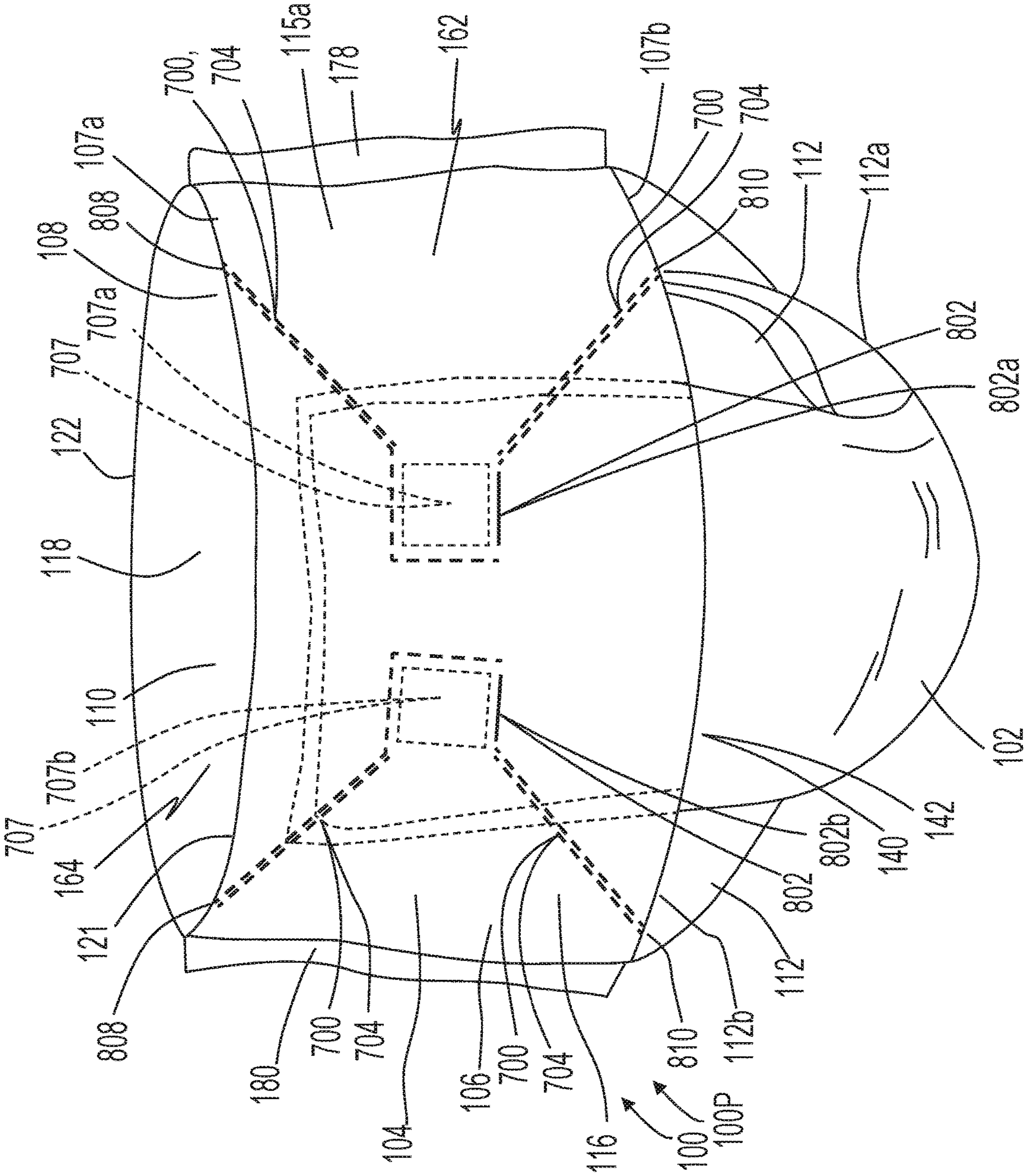
FIG. 6A is a perspective view of a diaper pant with frangible pathways.
Figure 6B:
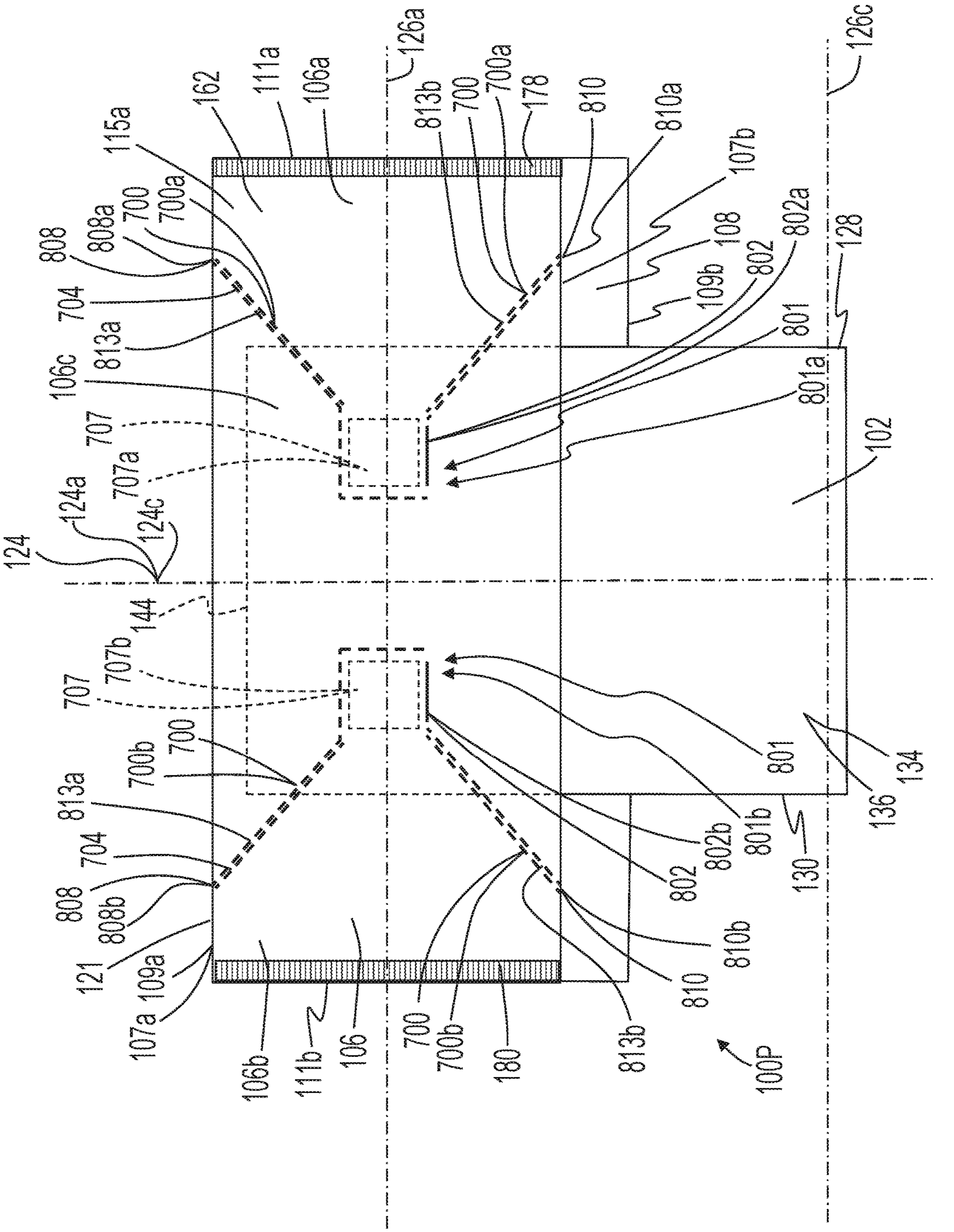
FIG. 6B is a front plan view of the diaper pant of FIG. 6A.

It is to be appreciated that frangible pathways 700 may be positioned in various locations and/or orientations relative to other components of the absorbent article 100 and/or may be configured to function in various ways to help facilitate removal of diaper pant from a wearer. For example, the diaper pant 100P shown in FIGS. 6A and 6B may include one or more frangible pathways 700 extending between a distal terminus 808 on the outer edge 107*a* of the first belt 106 and a distal terminus 810 on the inner edge 107*b* of the first belt 106. As illustrated in FIGS. 6A and 6B, the diaper pant 100P includes a first frangible pathway 700*a* and a second frangible pathway 700*b* in the first belt 106. The first frangible pathway 700*a* may extend between a first distal terminus 808*a* on the outer edge 107*a* of the first belt 106 and a first proximal terminus 810*a* on the inner edge 107*b* of the first belt 106. And the second frangible pathway 700*b* may extend between a second distal terminus 808*b* on the outer edge 107*a* of the first belt 106 and a second proximal terminus 810*b* on the inner edge 107*b* of the first belt 106. It is to be appreciated that the first and second frangible pathways 700*a*, 700*b* may comprise lines of weakness 704 as described above.

It is to be appreciated that the first distal terminus 808*a* and the second distal terminus 808*b* may be located in various lateral positions on the outer edge 107*a* of the first belt 106. For example, in some configurations, the first distal terminus 808*a* and/or the second distal terminus 808*b* may be positioned in the central region 106*c* of the first belt 106. In some configurations, the first distal terminus 808*a* and/or the second distal terminus 808*b* may be positioned laterally between the first longitudinal edge 128 and the second longitudinal edge 130 of the chassis 102. In some configurations, the first distal terminus 808*a* and/or the second distal terminus 808*b* may be positioned in the first end region 106*a* and/or the second end region 106*b* of the first belt 106. In some configurations, the first distal terminus 808*a* and/or the second distal terminus 808*b* may be positioned laterally outboard of the first longitudinal edge 128 and the second longitudinal edge 130 of the chassis 102. In some configurations, the first distal terminus 808*a* and/or the second distal terminus 808*b* may be positioned laterally between the first longitudinal edge 128 of the chassis 102 and the first side seam 178 and/or may be positioned laterally between the second longitudinal edge 130 of the chassis 102 and the second side seam 180. In some configurations, the first distal terminus 808*a* may be laterally aligned with the first longitudinal edge 128 of the chassis 102 or the first longitudinal side edge 111*a* of the first belt 106. In some configurations, the first distal terminus 808*a* may be positioned laterally between the first longitudinal edge 128 of the chassis 102 and the first longitudinal side edge 111*a* of the first belt 106. In some configurations, the second distal terminus 808*b* may be laterally aligned with the second longitudinal edge 130 of the chassis 102 or the second longitudinal side edge 111*b* of the first belt 106. In some configurations, the second distal terminus 808*b* may be positioned laterally between the second longitudinal edge 130 of the chassis 102 and the second longitudinal side edge 111*b* of the first belt 106.

It is also to be appreciated that the first proximal terminus 810*a* and the second proximal terminus 810*b* may be located in various lateral positions on the inner edge 107*b* of the first belt 106. For example, in some configurations, the first proximal terminus 810*a* and/or the second proximal terminus 810*b* may be positioned in the central region 106*c* of the first belt 106. In some configurations, the first proximal terminus 810*a* and/or the second distal terminus 810*b* may be positioned laterally between the first longitudinal edge 128 and the second longitudinal edge 130 of the chassis 102. In some configurations, the first proximal terminus 810*a* and/or the second proximal terminus 810*b* may be positioned in the first end region 106*a* and/or the second end region 106*b* of the first belt 106. In some configurations, the first proximal terminus 810*a* and/or the second proximal terminus 810*b* may be positioned laterally outboard of the first longitudinal edge 128 and the second longitudinal edge 130 of the chassis 102. In some configurations, the first proximal terminus 810*a* and/or the second proximal terminus 810*b* may be positioned laterally between the first longitudinal edge 128 of the chassis 102 and the first side seam 178 and/or may be positioned laterally between the second longitudinal edge 130 of the chassis 102 and the second side seam 180. In some configurations, the first proximal terminus 810*a* may be laterally aligned with the first longitudinal edge 128 of the chassis 102 or the first longitudinal side edge 111*a* of the first belt 106. In some configurations, the first proximal terminus 810*a* may be positioned laterally between the first longitudinal edge 128 of the chassis 102 and the first longitudinal side edge 111*a* of the first belt 106. In some configurations, the second proximal terminus 810*b* may be laterally aligned with the second longitudinal edge 130 of the chassis 102 or the second longitudinal side edge 111*b* of the first belt 106. In some configurations, the second proximal terminus 810*b* may be positioned laterally between the second longitudinal edge 130 of the chassis 102 and the second longitudinal side edge 111*b* of the first belt 106.

It is to be appreciated that the first distal terminus 808*a* and the second distal terminus 808*b* may be located in various longitudinal positions between the outer edge 107*a* and the inner edge 107*b* of the first belt 106. And the first proximal terminus 810*a* and the second proximal terminus 810*b* may be located in various longitudinal positions between the outer edge 107*a* and the inner edge 107*b* of the first belt 106. For example, in some configurations, such as shown in FIG. 6B1 for example, the first distal terminus 808*a* and/or the first proximal terminus 810*a* may be located on the first side seam 178 at positions longitudinally inboard of the outer edge 107*a* and longitudinally outboard of the inner edge 107*b* of the first belt 106. Also, as shown in FIG. 6B1, the second distal terminus 808*b* and/or the second proximal terminus 810*b* may be located on the second side seam 180 at positions longitudinally inboard of the outer edge 107*a* and longitudinally outboard of the inner edge 107*b* of the first belt 106. As such, completing the tearing process of the first belt 106 may also require tearing portions of the first and/or second side seams 178, 180.

With continued reference to FIG. 6B, the first belt 106 may also comprise grip regions 801 providing a place where a user may grasp a portion of the first belt 106 and begin the process of tearing the first belt along the frangible pathway 700. The grip region 801 may comprise an accessibility opening 802 in the first belt 106 and may also comprise a fastener component 707 positioned adjacent the accessibility opening 802. The accessibility opening 802 may comprise slits and/or openings in the first belt 106 and may penetrate through some or all layers of the first belt 106. It is to be appreciated that such slits or openings may be curved and/or straight. The accessibility opening 802 may also be considered part of the frangible pathway 700.

As shown in FIG. 6B, the diaper pant 100P may include a first grip region 801*a* including a first accessibility opening 802*a* and second grip region 801*b* including a second accessibility opening 802*b* in the first belt 106. The first and second accessibility openings 802*a*, 802*b* may be positioned between the outer edge 107*a* and the inner edge 107*b* of the first belt 106. The first and second accessibility openings 802*a*, 802*b* may also be positioned in the central region 106*c* of the first belt 106 and may be positioned between the first longitudinal edge 128, the second longitudinal edge 130 of the chassis 102, and the first lateral edge 144 of the chassis 102. In addition, a first fastener component 707*a* may be positioned adjacent the first accessibility opening 802*a*, and a second fastener component 707*a* may be positioned adjacent the second accessibility opening 802*a*. The first frangible pathway 700*a* comprises a first tear zone 813*a* extending from the first accessibility opening 802*a* to the first distal terminus 808*a* and a second tear zone 813*b* extending from the first accessibility opening 802*a* to the first proximal terminus 810*a*. The second frangible pathway 700*b* comprises a first tear zone 813*a* extending from the second accessibility opening 802*b* to the second distal terminus 808*b* and a second tear zone 813*b* extending from the second accessibility opening 802*b* to the second proximal terminus 810*b*. As discussed in more detail below, the accessibility opening 802 may help provide a caregiver or wearer access to and/or to grasp the fastener component 707 in the grip region 801 with a finger or thumb. The caregiver or user may then pull on grip region 801 to begin tearing the first belt 106 on the frangible pathway 700. In some configurations, tear lines may simultaneously propagate along the first tear zone 813*a* and the second tear zone 813*b* laterally outward from the central region 106*c* of the first belt 106 toward the distal terminus 808 and the proximal terminus 810. It is also to be appreciated that some diaper pants 100P herein may be configured to include a frangible pathway 700 that extends through or around the fastener component 707 without an accessibility opening. In turn, a user may pinch and/or pull the belt where the frangible pathway 700 is located at or adjacent the fastener component 707 to initiate the tearing process along the frangible pathway 700.

As shown in FIG. 6B, the frangible pathways 700 may be configured to extend laterally inward from the from the distal terminus 808 and/or the proximal terminus 810. In turn, portions of the frangible pathway 700 may extend to define an angle that is less than 90 degrees with respect to the outer edge 107*a* and/or the inner edge 107*b* of the first belt 106. Thus, the frangible pathway may define an overall length that is greater than a longitudinal length LT1 of the first belt 106 and/or the longitudinal length LT2 of the second belt 108 discussed above with reference to FIGS. 2C-2E.

It is to be appreciated that grip regions 801 and accessibility openings 802 may be located in various positions in the first end region 106*a*, the second end region 106*b*, and/or the central region 106*c* of the first belt 106. Grip regions 801 and accessibility openings 802 may be positioned between the first longitudinal side edge 111*a*, the second longitudinal side edge 111*b*, the outer edge 107*a*, and the inner edge 107*b* of the first belt 106. For example, the first accessibility opening 802*a* and/or the second accessibility 802*b* may be entirely laterally positioned between the first longitudinal edge 128 and the second longitudinal edge 130 of the chassis 102. In some configurations, the first accessibility opening 802*a* may be positioned laterally between the first longitudinal side edge 128 of the chassis 102 and the first longitudinal side edge 111*a* of the first belt 106 and/or first side seam 178. In some configurations, the second accessibility opening 802*b* may be positioned laterally between the second longitudinal side edge 130 of the chassis 102 and the second longitudinal side edge 111*b* of the first belt 106 and/or second side seam 180. In some configurations, the first accessibility opening 802*a* and/or the second accessibility opening 802*b* may be positioned longitudinally between the first lateral edge 144 of the chassis 102 and the inner edge 107*b* of the first belt 106 and/or may be positioned longitudinally between the first lateral edge 144 of the chassis 102 and the outer edge 107*a* of the first belt 106. In some configurations, the first accessibility opening 802*a* may extend across the first longitudinal edge 128 and/or the first lateral edge 144 of the chassis 102, and/or the second accessibility opening 802*b* may extend across the second longitudinal edge 130 and/or the first lateral edge 144 of the chassis 102.

It is also be appreciated that accessibility openings 802 may be located in various positions relative to fastener components 707. For example, in some configurations, the accessibility opening 802 may be positioned longitudinally between the fastener component 707 and the outer edge 107*a* of the first belt 106. In some configurations, the accessibility opening 802 may be positioned longitudinally between the fastener component 707 and the inner edge 107*b* of the first belt 106. In some configurations, the accessibility opening 802 may be positioned laterally inboard of the fastener component 707. It is also to be appreciated that more than one accessibility opening 802 may be located adjacent a fastener component 707. As discussed in more detail below, the accessibility opening 802 also be configured to extend partially or entirely through a fastener component 707 and may divide a fastener component 707 into two or more parts.

As mentioned above, the accessibility opening 802 may comprise slits and/or openings in the first belt 106 and may be curved and/or straight. It is to be appreciated that the accessibility openings 802 may also be oriented in various ways. For example, the accessibility opening 802 may be generally oriented perpendicularly relative to the outer edge 107*a* and/or the inner edge 107*b* of the first belt 106. In some configurations, the accessibility opening 802 may be generally oriented parallel relative to the outer edge 107*a* and/or the inner edge 107*b* of the first belt 106. In some configurations, the accessibility opening 802 may comprise a slit that extends along a line in a lateral direction to define an angle from about 0 degrees to about 45 degrees with respect to the outer edge 107*a* and/or the inner edge 107*b* of the first belt 106, specifically reciting all 1 degree increments within the above-recited range and all ranges formed therein or thereby. In some configurations, the accessibility opening 802 may define a length dimension in the range of about mm to about 50 mm, specifically reciting all 0.1 mm increments within the above-recited range and all ranges formed therein or thereby.

Figure 7A:
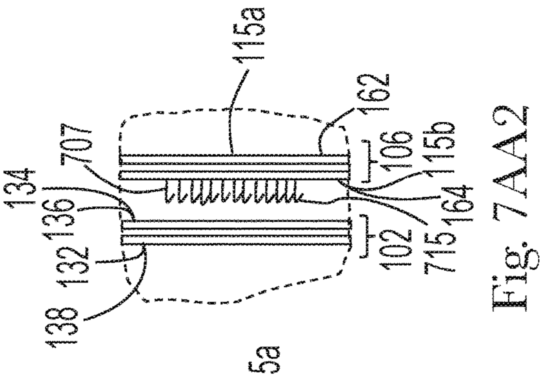
FIG. 7A is a detailed view of a fastener component configuration.
Figure 7A:
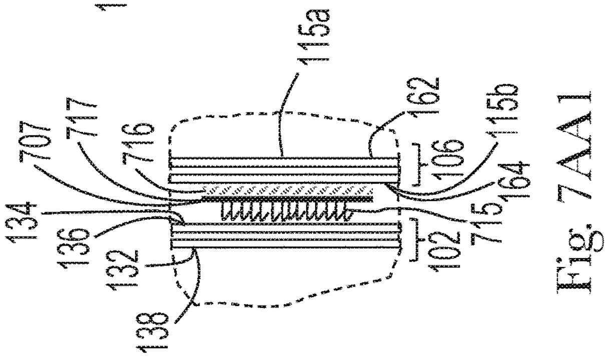
Figure 7A:
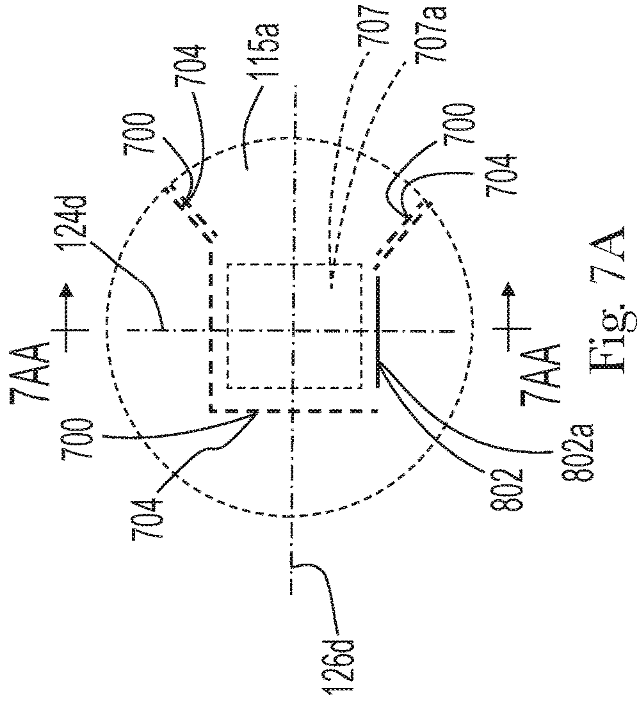

As discussed above, the diaper pant 100P may include one or more fastener components 707 adapted to refastenably connect with at least one other component of the diaper pant 100P in a disposal configuration. It is to be appreciated that the fastener components 707 may be configured in various shapes and sizes, and may be located in various positions relative to other components of the diaper pant 100P. As shown in FIG. 7A, the fastener components 707 may comprise a lateral centerline 126*d* oriented substantially parallel to the lateral centerline 126*a* of the first elastic belt 106 and/or the lateral centerline 126*b* of the second elastic belt 108 and/or the lateral centerline 126*c* of the chassis 102. The fastener components 707 may comprise a longitudinal centerline 124*d* oriented substantially parallel to the longitudinal centerline 124*a* of the first elastic belt 106 and/or the longitudinal centerline 124*b* of the second elastic belt 108 and/or the longitudinal centerline 124*c* of the chassis 102.

As shown in FIG. 7AA1, in some configurations, fastener components 707 may be positioned on and connected with the wearer facing surface 115*b* of the first elastic belt 106 and/or the second elastic belt 108 in a region where the first elastic belt 106 and/or second elastic belt 108 overlaps the chassis 102. In some configurations, the fastener component 707 may be sandwiched between the second substrate 164 of the first elastic belt 106 or the second elastic belt 108 and the backsheet 136 of the chassis 102. In some configurations, such as shown in FIG. 7AA1, the fastener component 707 comprises hooks 715 protruding from a base 717, and the hooks 715 extend from the first belt 106 toward the backsheet 136. The fastener component 707 may be configured as a separate discrete element that may be connected with the wearer facing surface 115*b* of the first belt 106 in various ways. For example, as shown in FIG. 7AA1, adhesive 716 may connect the base 717 of the fastener component 707 with wearer facing surface 115*b* of the first belt 106. It is to be appreciated that the fastener component 707 may be connected with the first belt 106 by mechanical bonding in addition to or instead of adhesive. It is to be appreciated that the base 717 may be configured in various ways. For example, the base 717 may comprise a thermoplastic film. In some configurations, the base 717 may comprise a laminate with various layers bonded together, such as disclosed for example in U.S. Patent Publication No. 2021/0045931 A1. For example, the base 717 may comprise a thermoplastic film layer bonded with a nonwoven layer. It is to be appreciated that such layers may be bonded together in various ways, such as with adhesive, mechanical bonding, and/or extrusion bonding. In some configurations, the fastener component 707 may be integrally formed from materials of the first belt 106, such as shown for example in FIG. 7AA2, or may be integrally formed from materials and attached with the first belt.

Figure 7B:
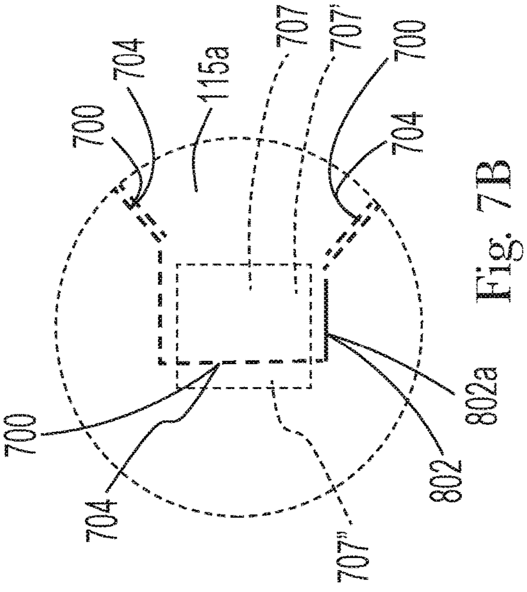
FIG. 7B is a detailed view of another fastener component configuration.

To help prevent contact of the fastener component 707 with a wearer's skin while wearing the diaper pant 100P, the fastener components 707 may be positioned on and connected with the wearer facing surface 115*b* of the first elastic belt 106 and/or the wearer facing surface 117*b* of the second elastic belt 108 in a region where the first elastic belt 106 and/or second elastic belt 108 overlaps the chassis 102. For example, the fastener component 707 may be sandwiched between the wearer facing surface **115*b* of the first belt 106 and the chassis 102. In some configurations, the fastener component 707 may be sandwiched between the second substrate 164 of the first elastic belt 106 or the second elastic belt 108 and the backsheet 136 of the chassis 102. In some configurations, the fastener component 707 may be positioned laterally between the first longitudinal side edge 128 and the second longitudinal side edge 130 of the chassis 102. The fastener component 707 may also be positioned longitudinally between the first lateral edge 144 of the chassis 102 and the inner edge 107*b* of the first belt 106. As shown in FIG. 7A, the fastener component 707 may be positioned adjacent the frangible pathway 700. The accessibility opening 802, which may be considered part of the frangible pathway 700, may be positioned adjacent the fastener component 707. As such, the frangible pathway 700 may partially surround the fastener component 707. In some configurations, such as shown in FIG. 7B, the frangible pathway 700 may extend through the fastener component 700, effectively dividing the fastener component 707 into a first fastener part 707' and a second fastener part 707"**.

Figure 7C:
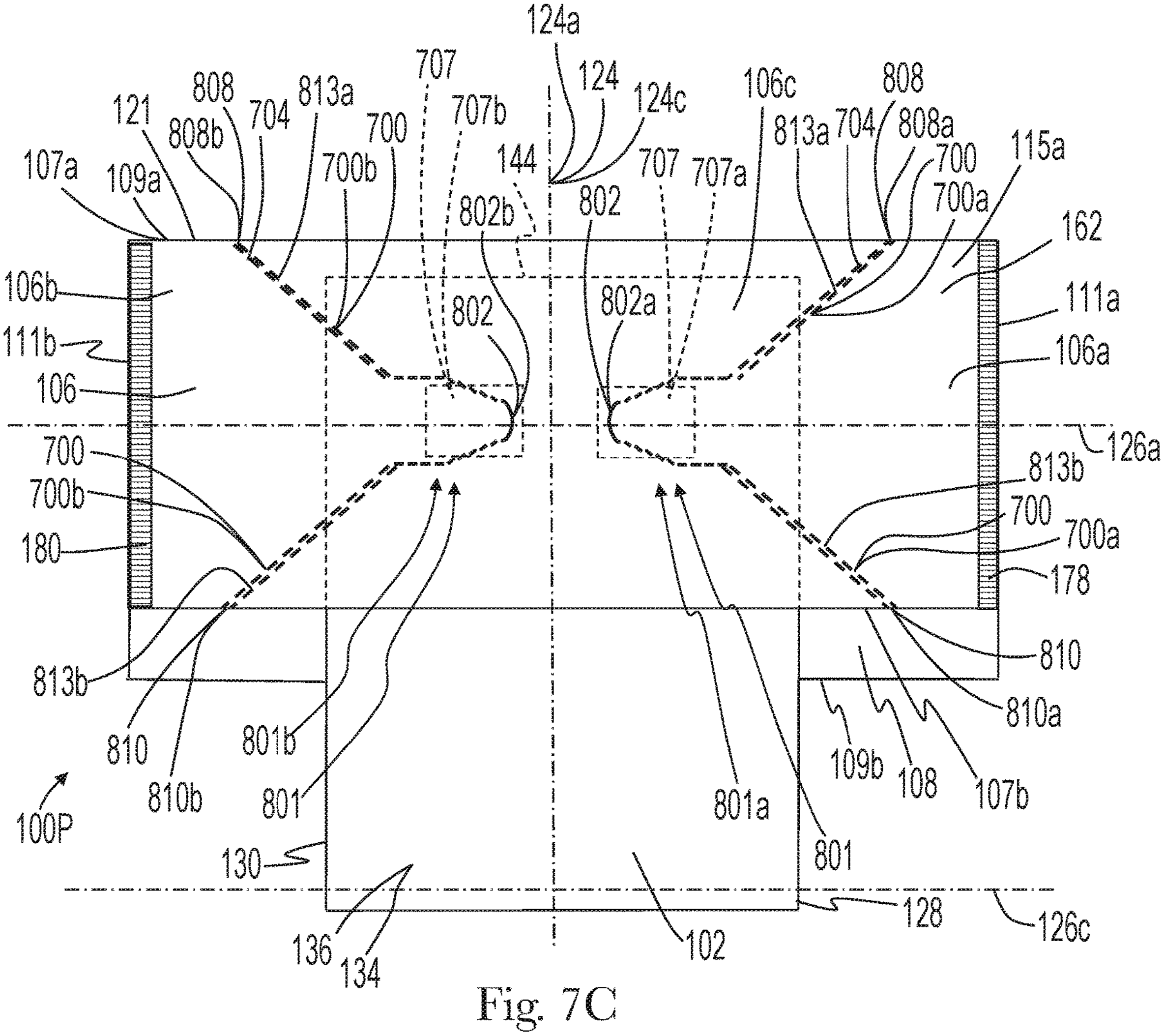
FIG. 7C shows a front plan view of a diaper with another configuration of fastener components, accessibility openings, and frangible pathways.
Figure 7D:
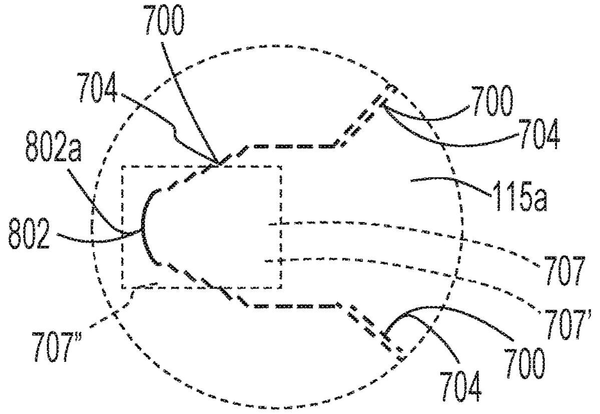
FIG. 7D is a detailed view of the fastener component configuration shown in FIG. 7C.
Figure 7E:
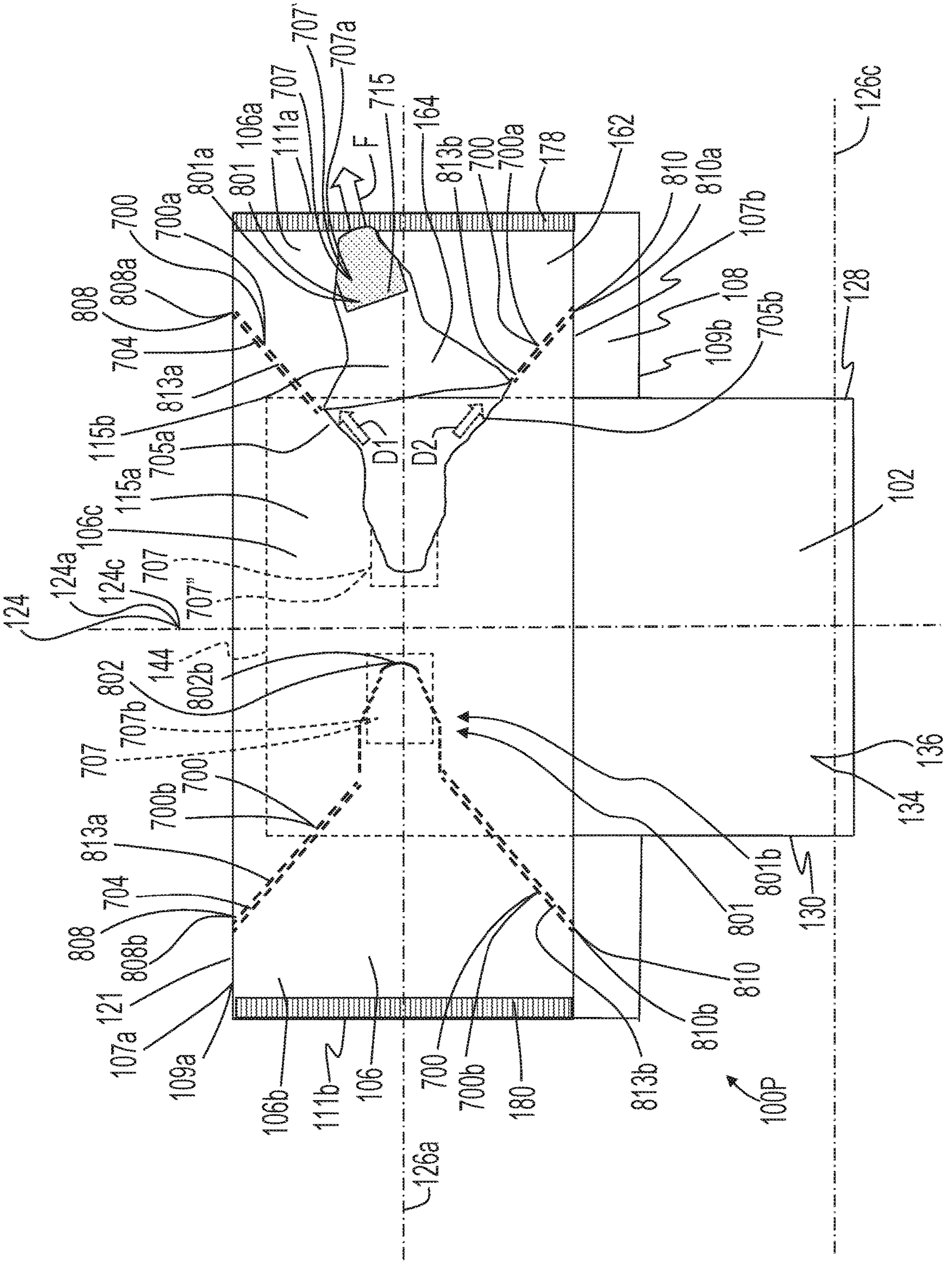
FIG. 7E shows a front plan view of the diaper pant of FIG. 6B as a first frangible pathway is being torn.

In another configuration shown in FIGS. 7C, 7D, and 7E, both the frangible pathway 700 and the accessibility opening 802 may extend through the fastener component, effectively dividing the fastener component 707 into a first fastener part 707' and a second fastener part 707". The accessibility openings 802 shown in FIG. 7C may comprise slits that are generally oriented in a longitudinal direction. In addition, the accessibility opening 802 extends through the fastener component 707 and may be positioned entirely within a perimeter of the fastener component. It is to be appreciated that such slits may be straight and/or curved. In some configurations, a longitudinally extending accessibility opening 802 may define a length dimension in the range of about 10 mm to about 30 mm, specifically reciting all 0.1 mm increments within the above-recited range and all ranges formed therein or thereby. In addition, in some configurations, a longitudinally extending accessibility opening 802 may also be curved to extend laterally in the range of about 2 mm to about 20 mm, specifically reciting all 0.1 mm increments within the above-recited range and all ranges formed therein or thereby.

Figure 7F:
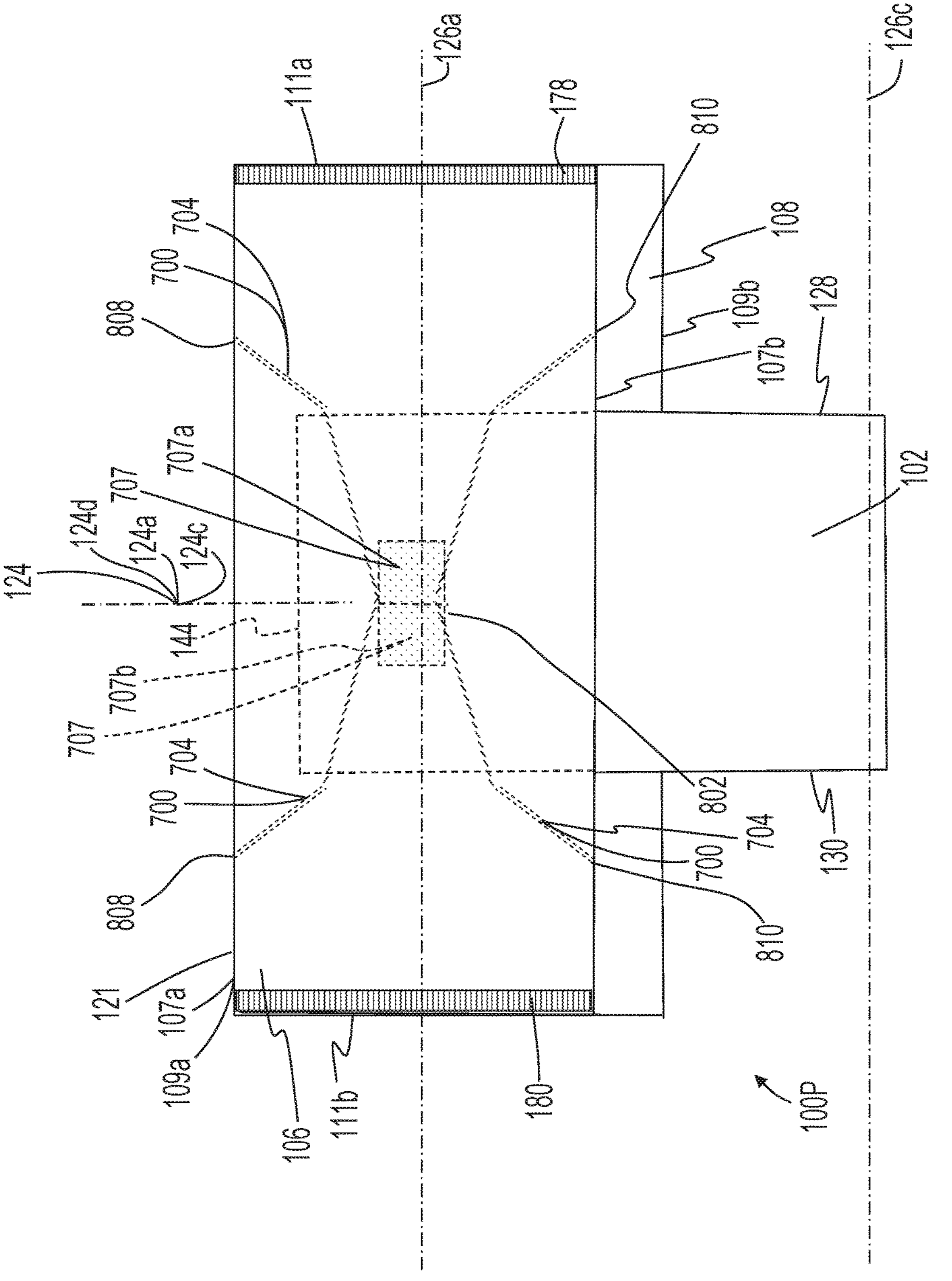
FIG. 7F shows a front plan view of a diaper with another configuration of frangible pathways.

In another configuration shown in FIG. 7F, the diaper pant 100P may comprise one fastener component 707 joined to the wearer facing surface **115*b* of the first belt 106 in a location overlapping the longitudinal centerline 124*c* of the chassis 102. The longitudinal centerline 124*d* of the fastener component 707 may be coincident with, or in proximity of, the longitudinal centerline 124*c* of the chassis 102. The frangible pathway 700 may divide fastener component 707 into the first fastener component 707*a* and the second fastener component 707*b* of substantially similar size and geometry. An accessibility opening 802 may be disposed at, or in proximity of, a longitudinally inboard lateral edge of the fastener component 707. Longitudinally outboard the lateral edges of the fastener component 707, the frangible pathway 700 may extend in longitudinal and lateral directions to the waist edge 121 and inner edge 107*b* of the first belt 106. A caregiver or wearer may access and grasp the fastener component 707 through the accessibility opening 802 and subsequently separate the frangible pathway 700 into the first and second fastener components 707*a*, 707*b***.

As discussed above, the first elastic belt 106 and/or the second belt 108 may be relatively easily torn along the frangible pathway 700, such as when removing the diaper pant 100P from a wearer. As discussed below with reference to FIGS. 6A-6F, frangible pathway 700 may be configured to allow a caregiver or wearer to initiate and/or completely tear the first belt 106 and/or the second belt 108 with one hand when removing a diaper pant 100P from a wearer. In addition, the first belt 106 may be separable along the first frangible pathway **700*a* and the second frangible pathway 700*b* to define a first belt zone 831, a second belt zone 832, and a third belt zone 833 positioned laterally between the first and second belt zones 831, 832**.

Referring now to FIGS. 6A and 6B, when removing a diaper pant 100P from a wearer, a user may grab the first belt 106 in the grip region 801 by inserting one or more fingers and/or a thumb through the accessibility opening 802 to grasp a portion of the first 106 and fastener component 707. For example, with reference to FIGS. 6B and 6C, a caregiver may insert a finger or thumb through the first accessibility opening **802*a* and grasp the first belt 106 and the first fastener component 707*a* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force F on the first grip region 801*a* of the first belt 106 outward away from the wearer to initiate a tearing of the first belt 106 along the first frangible pathway 700*a*, such as shown in FIG. 6**C.

Figure 6C:
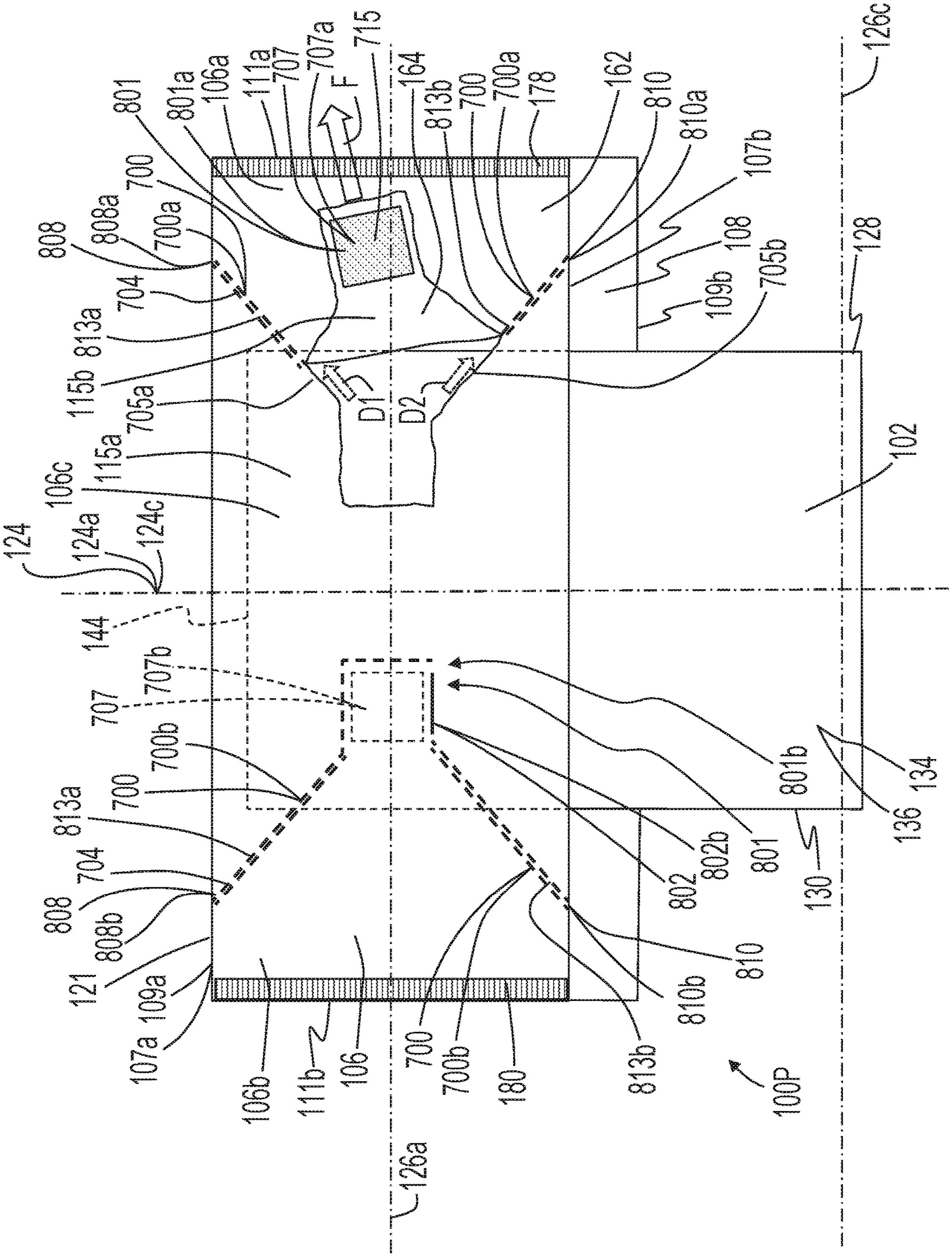
FIG. 6C shows a front plan view of the diaper pant of FIG. 6B as a first frangible pathway is being torn.

With continued reference to FIG. 6C, a force F generally represented by an arrow is applied to the first grip region **801*a* in a direction generally toward the first end region 106*a* of the first belt 106 and/or outward away from the first belt 106 and the wearer. As the force F is applied, a first tear line 705*a* and a second tear line 705*b* may simultaneously propagate along the first tear zone 813*a* and the second tear zone 813*b*, respectively. The first tear line 705*a* may propagate from the first accessibility opening 802*a* along the first tear zone 813*a* of the first frangible pathway 700*a* in longitudinal and lateral directions around the first fastener component 707*a* and then in a direction D1 that is generally laterally and longitudinally outward from the central region 106*c* of the first belt 106 and toward the first distal terminus 808*a* in the first end region 106*a* of the first belt 106. Simultaneously, the second tear line 705*b* may propagate from the first accessibility opening 802*a* along the second tear zone 813*b* of the first frangible pathway 700*a* in a direction D2 that is generally laterally outward and longitudinally inward from the central region 106*c* of the first belt 106 and toward the first proximal terminus 810*a* in the first end region 106*a* of the first belt 106. Similar to the view shown in FIG. 6C, FIG. 7E shows a front plan view of the diaper pant of FIG. 7C as the first frangible pathway 700*a* is being torn. As shown in FIG. 7E, the first fastener part 707' is separated from the second fastener part 707"** as the frangible pathway is torn.

Figure 6D:
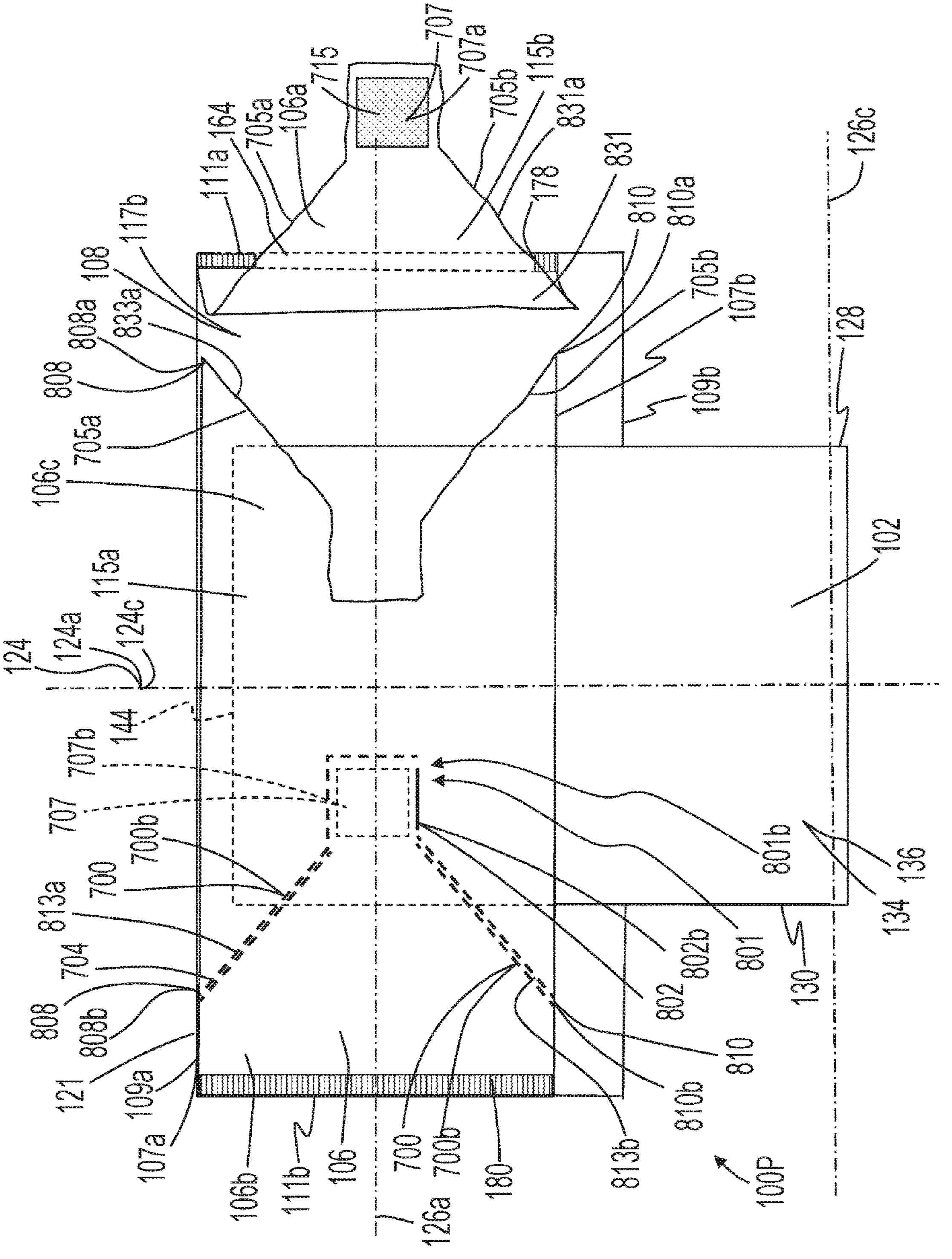
FIG. 6D shows a front plan view of the diaper pant of FIG. 6C after the first frangible pathway has been completely torn.

As shown in FIG. 6D, the first belt 106 may be separable along the first frangible pathway **700*a* to define a first belt zone 831. For example, the first belt zone 831 may be formed once the first tear line 705*a* propagates through the first distal terminus 808*a* and the second tear line 705*b* propagates through to the first proximal terminus 810*a*, the first belt zone 831 may be formed. As shown in FIG. 6D, a first edge 831*a* of the first belt zone 831 is formed by tearing the first frangible pathway 700*a*. In addition, a first edge 833*a* of the third belt zone 833 discussed in more detail below is also formed by tearing the first frangible pathway 700*a*. The first belt zone 831** may extend from the first edge

831*a* of the first and second tear lines 705*a*, 705*b* to the first side seam 178 or the first longitudinal side edge 111*a* of the first belt 106. In addition, the first belt zone 831 may include the first fastener component 707*a*.

Figure 6E:
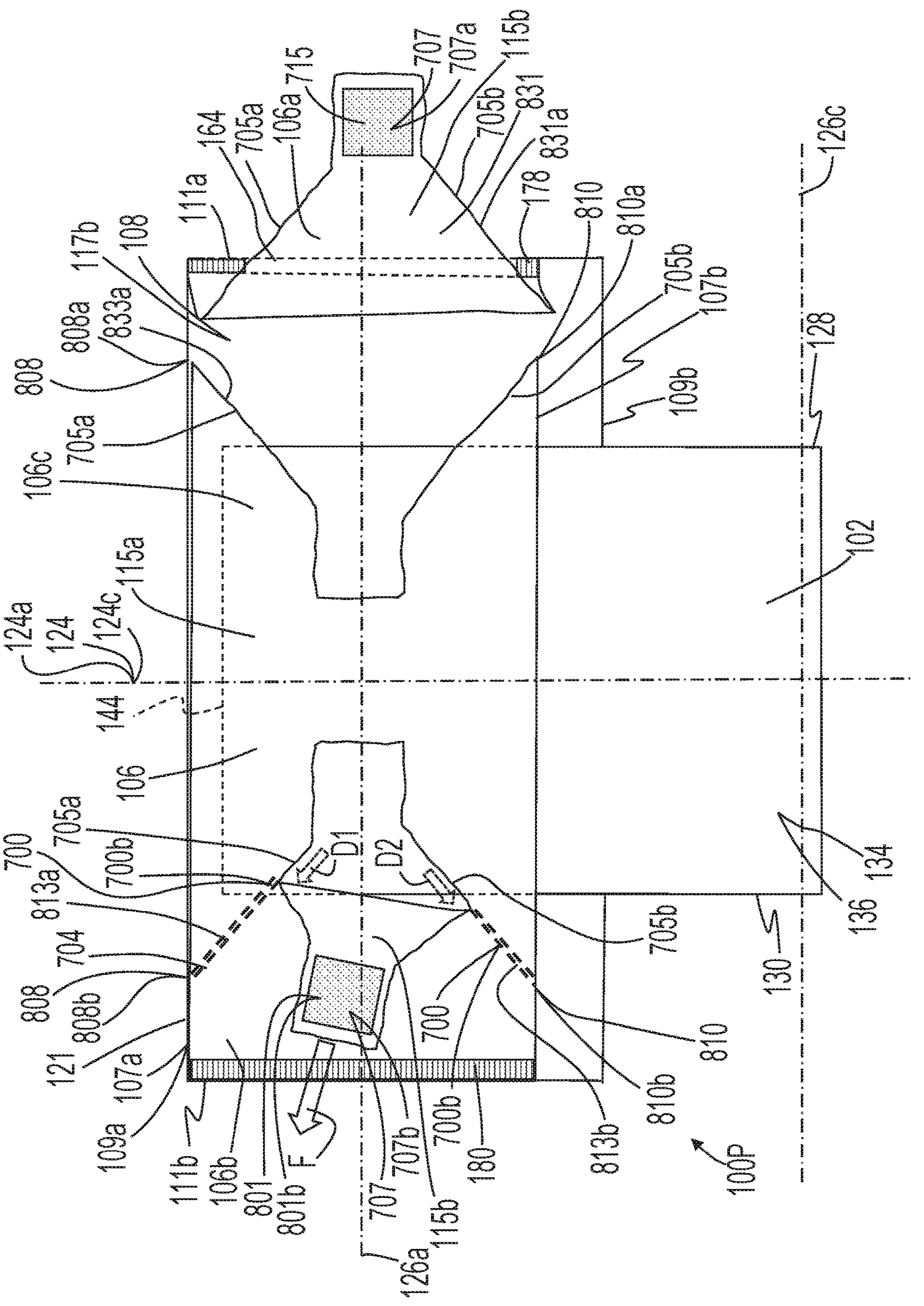
FIG. 6E shows a front plan view of the diaper pant of FIG. 6D as a second frangible pathway is being torn.

With the first belt zone 831 being defined by tearing the first belt 106 along the first frangible pathway 700*a*, a user may proceed to define the second belt zone 832 by tearing the first belt 106 along the second frangible pathway 700*b*. Referring now to FIGS. 6D and 6E, a caregiver may insert a finger or thumb through the second accessibility opening 802*b* and grasp the first belt 106 and the second fastener component 707*b* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force F on the second grip region 801*b* of the first belt 106 outward away from the wearer to initiate a tearing of the first belt 106 along the second frangible pathway 700*b*, such as shown in FIG. 6E.

With continued reference to FIG. 6E, a force F generally represented by an arrow is applied to the second grip region 801*b* in a direction generally toward the second end region 106*b* of the first belt 106 and/or outward away from the first belt 106. As the force F is applied, a first tear line 705*a* and a second tear line 705*b* may simultaneously propagate along the first tear zone 813*a* and the second tear zone 813*b*, respectively. The first tear line 705*a* may propagate from the second accessibility opening 802*b* along the first tear zone 813*a* of the second frangible pathway 700*b* in longitudinal and lateral directions around the second fastener component 707*b* and then in a direction D1 that is generally laterally and longitudinally outward from the central region 106*c* of the first belt 106 and toward the second distal terminus 808*b* in the second end region 106*b* of the first belt 106. Simultaneously, the second tear line 705*b* may propagate from the second accessibility opening 802*b* along the second tear zone 813*b* of the second frangible pathway 700*b* in a direction D2 that is generally laterally outward and longitudinally inward from the central region 106*c* of the first belt 106 and toward the second proximal terminus 810*b* in the second end region 106*b* of the first belt 106.

Figure 6F:
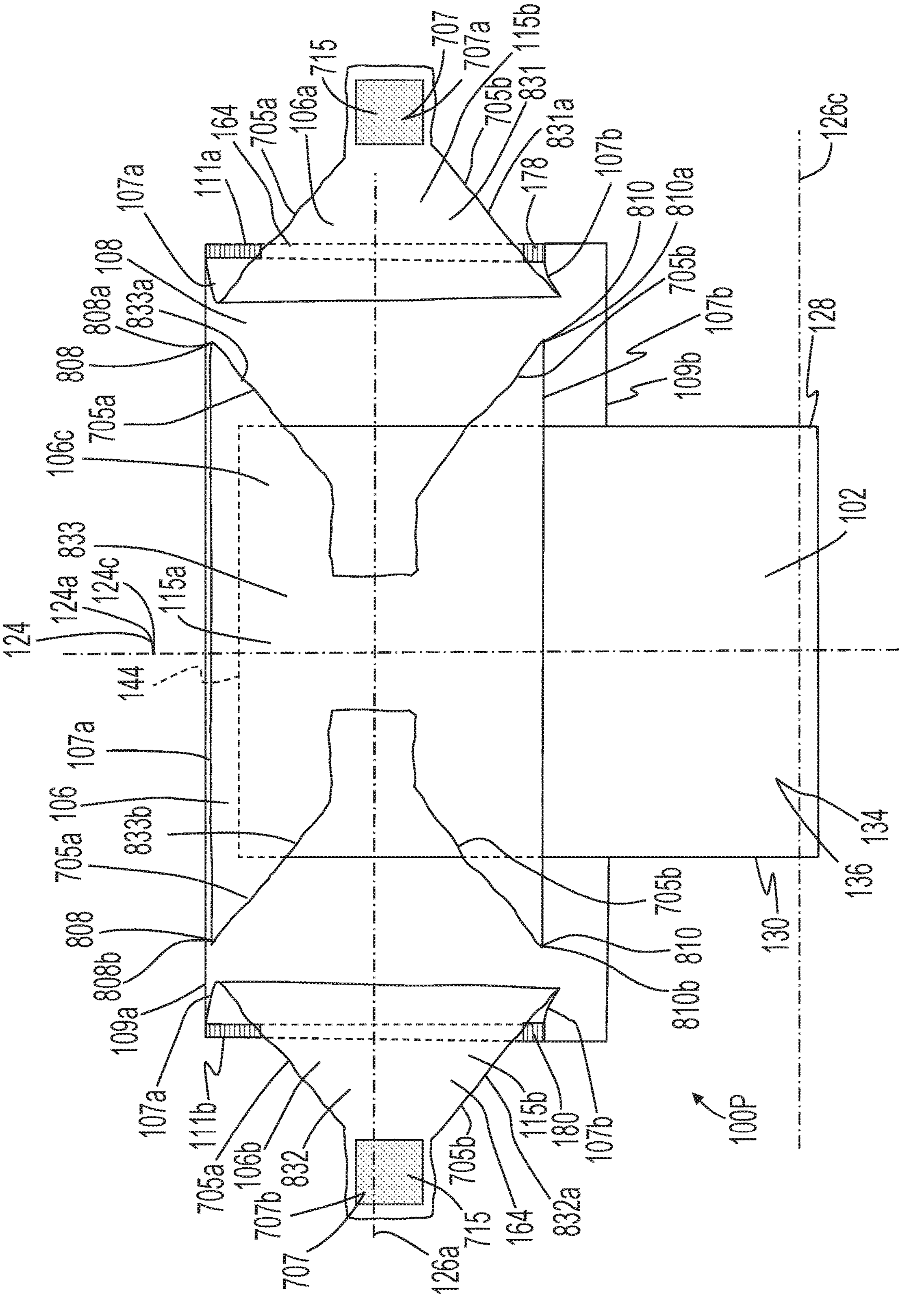
FIG. 6F shows a front plan view of the diaper pant of FIG. 6E after the second frangible pathway has been completely torn.

As shown in FIG. 6F, the first belt 106 may be separable along the second frangible pathway 700*b* to define a second belt zone 832 and a third belt zone 833. For example, the second belt zone 832 may be formed once the first tear line 705*a* propagates through the second distal terminus 808*b* and the second tear line 705*b* propagates through to the second proximal terminus 810*b*, the second belt zone 832 may be formed. As shown in FIG. 6F, a first edge 832*a* of the second belt zone 832 is formed by tearing the second frangible pathway 700*b*. In addition, a second edge 833*b* of the third belt zone 833 is also formed by tearing the second frangible pathway 700*b*. The second belt zone 832 may extend from the first edge 832*a* of the first and second tear lines 705*a*, 705*b* to the second side seam 180 or the second longitudinal side edge 111*b* of the first belt 106. In addition, the second belt zone 832 may include the second fastener component 707*b*. The third belt zone 833 may extend laterally between the first edge 833*a* and the second edge 833*b* and may remain connected with the chassis 102. When completing the tearing operation on the configuration shown in FIGS. 7C-7E, the first belt zone 831 and the second belt zone 832 will include first fastener parts 707', and the third belt zone 833 will include second fastener parts 707" separated from respective first fastener parts 707' during the tearing of frangible pathways 700.

Although the tearing process is described above with reference to FIGS. 6A-6F as tearing the first belt 106 along the first frangible pathway 700*a* before tearing the first belt along the second frangible pathway 700*b*, it is to be appreciated that the tearing of first belt 106 along the frangible pathways 700 may occur in various different orders and in different manners. For example, the first belt 106 may be torn along second frangible pathway 700*b* to define the second belt zone 832 before tearing the first belt 106 along the first frangible pathway 700*a* to define the first belt zone 831. In another example, the first belt 106 may be torn simultaneously along the first frangible pathway 700*a* and the second frangible pathway 700*b* to define the first belt zone 831, the second belt zone 832, and the third belt zone 833.

Once the first belt 106 is torn along the frangible pathways 700 to define the first belt zone 831, the second belt zone 832, and the third belt zone 833, the diaper pant 100P may be removed from a wearer in a manner similar to that of a conventional taped diaper. After being removed from a wearer, the diaper pant 100P may be placed in a disposal configuration, such as discussed above with reference to FIGS. 5A and 5B, by rolling and/or folding the chassis 102 onto itself in a longitudinal direction. The first belt zone 831 and the second belt zone 832 may be used to further wrap the diaper pant 100P onto itself. And the fastener components 707 on the first belt zone 831 and the second belt zone 832 may be connected with another portion of the diaper pant 100P to help maintain the diaper pant 100P in the disposal configuration.

It is to be appreciated that various types of arrangements of adhesive may be used to connect the chassis 102 with the first belt 106 and the second belt 108. As discussed below, such arrangements of adhesive may be configured to help ensure the chassis 102 remains connected with the first and second belts 106, 108 during use, while at the same time mitigating hinderances to a user's ability to initiate and complete tearing of the first and/or second belts 106, 108 along frangible pathways 700 during removal of the diaper pant 100P from a wearer.

Figure 8A:
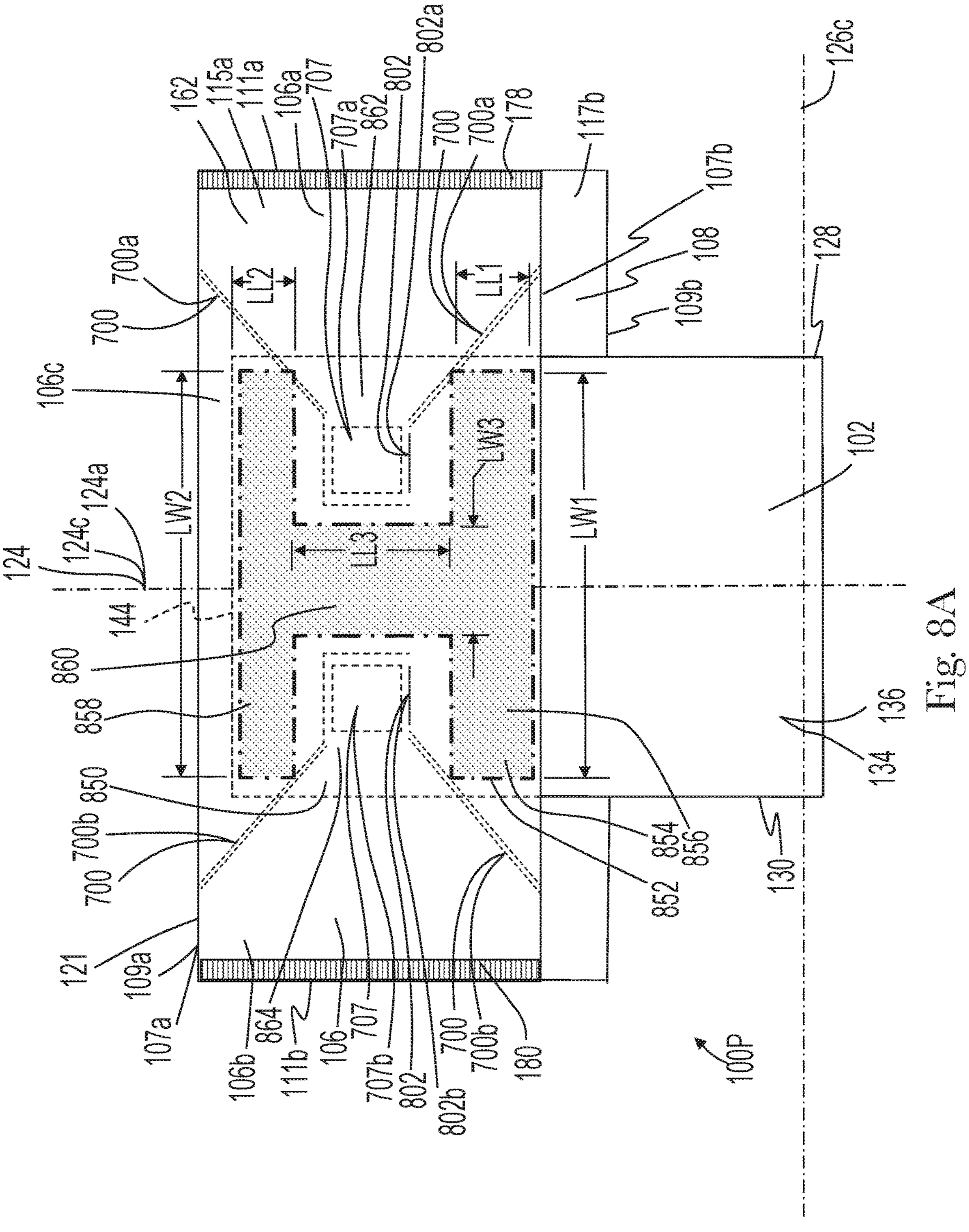
FIG. 8A shows a front plan view of the diaper pant of FIG. 6B illustrating various positional relationships with chassis-belt adherence zones.

As shown for example in FIG. 8A, a portion of the chassis 102 overlaps the inner wearer facing surface 115*b* of the first belt 106 to define a chassis overlap region 850. As such, the chassis overlap region 850 may extend laterally between the first longitudinal edge 128 and the second longitudinal edge 130 of the chassis 102 and longitudinally between the first lateral edge 144 of the chassis 102 and the inner edge 107*b* of the first belt 106. The chassis overlap region 850 may comprise an adherence region 852 where adhesive 854 is positioned between the backsheet 136 of the chassis 102 and the inner wearer facing surface 115*b* of the first belt 106. As such, the adhesive 854 in the adherence region 852 may permanently bond the chassis 102 with the first belt 106. A "permanent bond" refers to attachment of two or more elements or portions of elements together in a manner in which the elements are not intended to be separated during normal use. It is to be appreciated that permanent bonds in the adherence region 852 may be formed with a variety of methods, such as for example, applying molten adhesive or polymer between substrates; mechanical and/or thermal bonding; ultrasonic welding; mechanical entanglement using needle punching or hydrojetting; stitching; and any other means common to the art used to connect substrates or garments. Separation of such a permanent bond results in degradation of not only the attachment, but of at least portions of the elements. It is to be appreciated that the adhesive 854 may be applied in the adherence region 852 in various ways. For example, the adherence region 852 may comprise laterally extending stripes of adhesive 854 longitudinally separated from each other. In some configurations, the adherence region 852 may comprise a contiguous layer of adhesive 854.

With continued reference to FIG. 8A, the adherence region 852 may comprise a first adherence zone 856, a second adherence zone 858, and a third adherence zone 860. The first adherence zone may be positioned adjacent the inner edge 107*b* of the first belt 106, and the second adherence zone may be positioned adjacent the first lateral edge 144 of the chassis 102. The third adherence zone 860 may be positioned longitudinally between the first adherence zone 856 and the second adherence zone 858. In some configurations, the first adherence zone 856 may be coterminous with or spaced longitudinally outward from the inner edge 107*b* of the first belt 106. In some configurations, the second adherence zone 858 may be coterminous with or spaced longitudinally inward from the first lateral edge 144 of the chassis 102. In some configurations, the first adherence zone 856 and/or the second adherence zone 858 may be coterminous with or spaced laterally inward from the first longitudinal edge 128 and/or the second longitudinal edge 130 of the chassis 102.

It is to be appreciated that the first adherence zone 856, the second adherence zone 858, and the third adherence zone 860 may comprise various relative longitudinal lengths and widths. For example, the first adherence zone 856 may comprise a first lateral width LW1 and a first longitudinal length LL1, the second adherence zone may comprise a second lateral width LW2 and second longitudinal length LL2, and the third adherence zone may comprise a third lateral width LW3 and a third longitudinal length LL3. In some configurations, the first lateral width LW1 and/or the second lateral width LW2 may be greater than the third lateral width LW3. In some configurations, the first lateral width LW1 may be equal to or different from the second lateral width LW2. In some configurations, the first longitudinal length LL1, the second longitudinal length LL2, and the third longitudinal length LL3 may be equal or different from each other. In some configurations, the third longitudinal length LL3 may be greater than the first longitudinal length LL1 and the second longitudinal length LL2, and the first longitudinal length LL1 may be equal to or greater than the second longitudinal length LL2.

As shown in FIG. 8A, the first frangible pathway 700*a* and the second frangible pathway 700*b* extend across the overlap region 850 in opposing directions laterally outward from the third adherence zone 860. As such, the first frangible pathway 700*a* and the second frangible pathway 700*b* may not extend across the third adherence zone 860. In addition, the first fastener component 707*a*; the first accessibility opening 802*a*; and portions of the first frangible pathway 700*a* may be positioned laterally between the third adherence zone 860 and the first longitudinal side edge 128 of the chassis 102 and may be positioned longitudinally between the first adherence zone 856 and the second adherence zone 858. The second fastener component 707*b*; the second accessibility opening 802*b*; and portions of the second frangible pathway 700*b* may be positioned laterally between the third adherence zone 860 and the second longitudinal side edge 130 of the chassis 102 and may be positioned longitudinally between the first adherence zone 856 and the second adherence zone 858. In some configurations, the first frangible pathway 700*a* and/or the second frangible pathway 700*b* may or may not extend across the first adherence zone 856 and/or the second adherence zone 858. It is to be appreciated that the adherence region 852 and the frangible pathway 700 may be separated by various distances in longitudinal and lateral directions. For example, in some configurations, the adherence region 852 and the frangible pathway 700 may be separated by about 1 mm to about 50 mm in longitudinal and/or lateral directions, specifically reciting all 0.1 mm increments within the above-recited range and all ranges formed therein or thereby. In some configurations, the adherence region 852 and the frangible pathway 700 may be separated by a distance of about 5 mm in a longitudinal direction and/or by a distance of about 5 mm in a lateral direction and/or by distances of about 2.5 mm in both longitudinal and lateral directions.

With continued reference to FIG. 8A, the adherence region 852 may be configured to define a first pocket region 862 and a second pocket region 864 in the chassis overlap region 850. The chassis 102 may not be permanently bonded with the first belt 106 in the first pocket region 862 and the second pocket region 864. In some configurations, no adhesive between the chassis 102 and the first belt 106 may be present in the first pocket region 862 and/or the second pocket region 864. The first pocket region 862 may extend laterally between the third adherence zone 860 and the first longitudinal side edge 128 of the chassis 102, and the second pocket region 864 may extend laterally between the third adherence zone 860 and the second longitudinal side edge 130 of the chassis 102. In addition, the first pocket region 862 and the second pocket region 864 may extend longitudinally between the first adherence zone 856 and the second adherence zone 858. In some configurations, the first fastener component 707*a*; the first accessibility opening 802*a*; and/or portions of the first frangible pathway 700*a* may be positioned in the first pocket region 862. And the second fastener component 707*b*; the second accessibility opening 802*b*; and/or portions of the second frangible pathway 700*b* may be positioned in the second pocket region 864. Because the chassis 102 and first belt 106 are not permanently bonded together in the pocket regions 862, 864, it may be relatively easier for a user to grasp the first belt 106 and fastener components 707 through the accessibility openings 802 as well as initiate and complete the belt tearing process as described above.

Although the chassis 102 and the first belt 106 may not be bonded to each other in the pocket regions 862, 864, which may help improve the ease at which a user may initiate and complete the belt tearing process, there may be occasions when it is desirable to provide arrangements of releasable and/or refastenable bonds in the pocket regions 862, 862 to help increase the connection strength between the chassis 102 and the first belt 106 while at the same time mitigating hindrances to a user's ability to grasp the first belt 106 through the accessibility opening 802 as well as initiating and completing the belt tearing process.

Figure 8B:
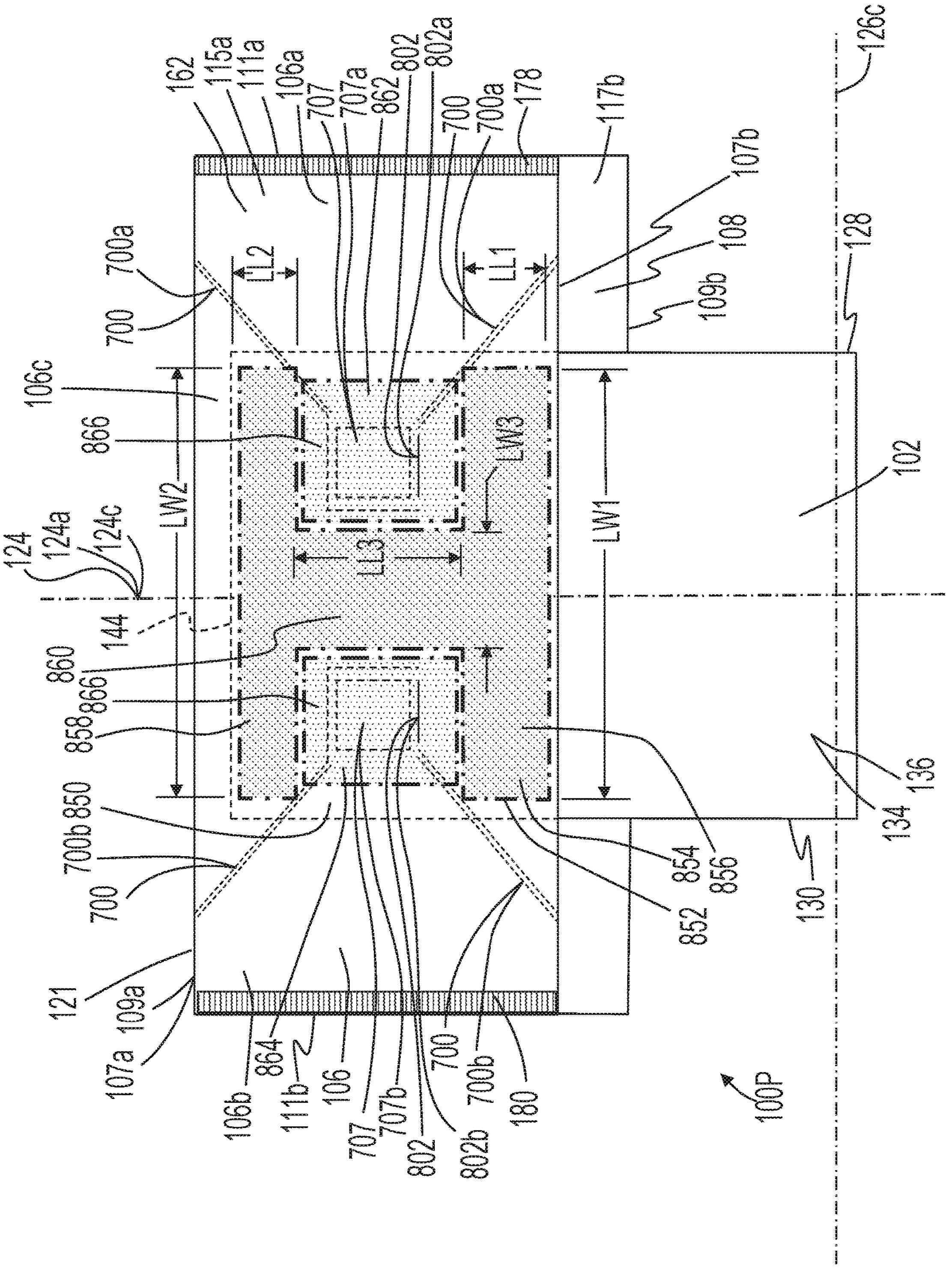
FIG. 8B shows a front plan view of the diaper pant of FIG. 6B illustrating additional various positional relationships with chassis-belt adherence zones.

For example, as shown in FIG. 8B, a second adhesive 866 may be positioned between the first belt 106 and the chassis 102 in the first pocket region 862 and/or the second pocket region 864. Instead of permanently bonding the chassis 102 with the first belt 106, the second adhesive 866 may be configured to releasably bond the chassis 102 with the first belt 106 in the first pocket region 862 and/or the second pocket region 864. The second adhesive 866 may be configured to provide additional bond strength between the chassis 102 and the first belt 106 to help prevent unintentional separation between the chassis 102 and the first belt 106 during use of the diaper pant 100P. When tearing the frangible pathways 700 during removal of the diaper pant 100P, the second adhesive 866 may be configured to allow a user to relatively easily peel or otherwise separate the first belt zone 831 and/or the second belt zone 832 apart from the chassis 102. As such, the adherence region 852 may comprise a first bond strength, and the first pocket region 862 and/or the second pocket region 864 may comprise a second bond strength, wherein the first bond strength is greater than the second bond strength. In some configurations, the second adhesive 866 may be the same as the adhesive 854 positioned in the adherence region 852. In some configurations, the second adhesive 866 may be different from the adhesive 854 positioned in the adherence region 852.

In some configurations, the adhesive 854 in the adherence region 852 may comprise a first basis weight and the second adhesive 866 in the first pocket region 862 and/or the second pocket region 864 may comprise a second basis weight, wherein the first basis weight is equal to or different from the second basis weight. In some configurations, the first basis weight may be greater than the second basis weight. In some configurations, the same or different types of adhesive may be positioned in the first pocket region 862 and the second pocket region 864.

As discussed above, fastener components 707 may be positioned between the first belt 106 and the chassis 102 in the first pocket region 862 and/or the second pocket region 864. In some configurations, the fastener components 707 may be configured to releasably connect the first belt 106 with the chassis 102 in the first pocket region 862 and/or the second pocket region 864. Such a releasable connection between the fastener components 707 and the chassis 102 may provide additional bond strength between the chassis 102 and the first belt 106 to help prevent unintentional separation between the chassis 102 and the first belt 106 during use of the diaper pant 100P. When tearing the frangible pathways 700 during removal of the diaper pant 100P, the releasable connection between the fastener components 707 and the chassis may be configured to allow a user to relatively easily peel or otherwise separate the first belt zone 831 and/or the second belt zone 832 apart from the chassis 102.

As discussed above, the backsheet 136 of the chassis 102 may comprise a laminate comprising a film layer and a nonwoven layer. In some configurations, the nonwoven layer may completely cover the film layer to define the garment facing surface 134 of the chassis 102. In some configurations, the nonwoven layer may partially cover the film layer, and as such, both the film layer and the nonwoven layer may define the garment facing surface 134 of the chassis 102. For example, in some configurations, the film layer may extend entirely between the inner edge 107*b* of the first belt 106 and the first lateral edge 144 of the chassis 102, and the nonwoven layer may also extend entirely between the inner edge 107*b* of the first belt 106 and the first lateral edge 144 of the chassis 102 to completely cover the film layer and define the garment facing surface 134 of the chassis 102 in the overlap region 850. As such, the first belt 106 may be bonded with the nonwoven layer in the first adherence zone 856, the second adherence zone 858, and the third adherence zone 860. In some configurations, the nonwoven layer may not extend entirely between the inner edge 107*b* of the first belt 106 and the first lateral edge 144 of the chassis 102, wherein a portion of the film layer may then be positioned in direct contact with the first belt 106. As such, the first belt 106 may be bonded with a portion of the nonwoven layer and a portion of the film layer in the adherence region 852. For example, the first belt 106 may be bonded with a portion of nonwoven layer of the backsheet 136 in the first adherence zone 856 and not in the second adherence zone 858 and not in the third adherence zone 860; while the first belt 106 may be bonded with a portion of film layer of the backsheet 136 in the first adherence zone 856 as well as in in the second adherence zone 858 and the third adherence zone 860.

In some configurations, a portion of the nonwoven layer of the backsheet 136 may be positioned between the fastener components 707 and the first belt 106. For example, as discussed above with reference to FIGS. 7AA1 and 7AA2, the fastener component 707 may comprise hooks 715 that extend toward the backsheet 136 of the chassis 102. As such, the hooks of the fastener component 707 may be releasably or refastenably connected with the nonwoven layer of the backsheet 136. In some configurations, the hooks of the fastener component 707 may not be releasably or refastenably connected with the film layer of the backsheet 136. In some configurations, the fastener component 707 may comprise a pressure sensitive adhesive instead of hooks, and as such, the pressure sensitive adhesive may releasably connect the fastener component 707 with the backsheet 136 in the first pocket region 862 and/or the second pocket region 864. In some configurations, such a pressure sensitive adhesive may be configured to releasably or refastenably connect the first belt 106 with a nonwoven layer and/or a film layer of the backsheet 136.

Figure 8C:
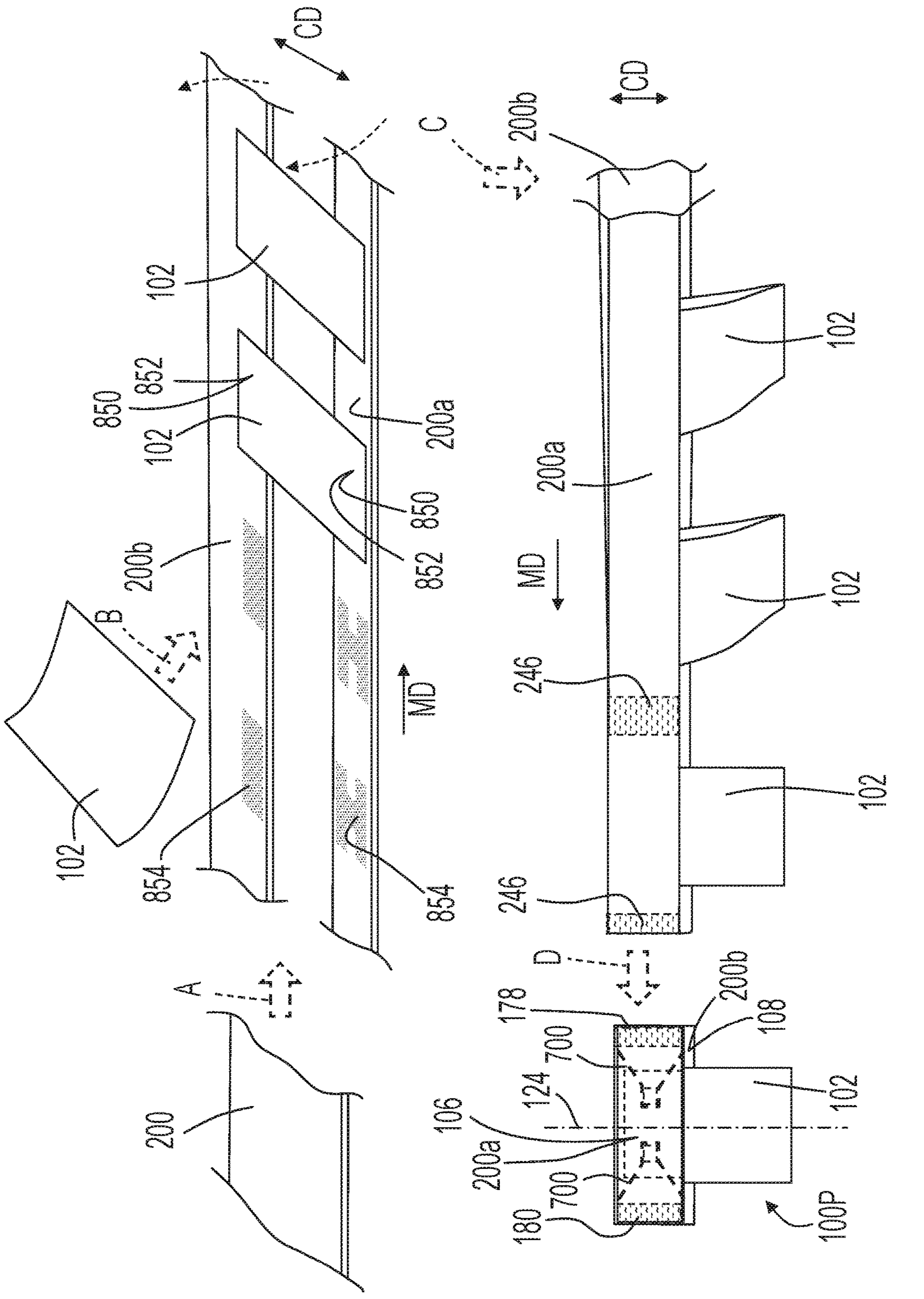
FIG. 8C is a schematic view of a diaper pant assembly process.

It is to be appreciated that the absorbent articles herein may be assembled in various ways utilizing various types of apparatuses configured to carry out various transformations in various orders of assembly. For example, as shown in FIG. 8C, when assembling diaper pants 100P, an elastic laminate 200 may be converted into a first elastic belt laminate 200*a* and/or a second elastic belt laminate 200*b* (represented by the dashed arrow "A"). The first elastic belt laminate 200*a* and the second elastic belt laminate 200*b* may be separated from each other in the cross direction CD. Adhesive 854 may be intermittently applied to first elastic belt laminate 200*a* and the second elastic belt laminate 200*b*. As shown in FIG. 8C, adhesive 854 may be applied in a pattern to define adherence regions 852 such as described above with reference to FIGS. 8A and 8B. It is to be appreciated that the adhesive 854 may be applied with applicator devices configured in various ways, such as for example, spray nozzles and/or slot coating devices. In some configurations, the adhesive applicator devices may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, all of which are incorporated by reference herein. In turn, opposing end regions of chassis 102 may be permanently bonded with the adhesive 854 in overlap regions 850 on the first elastic belt laminate 200*a* and/or a second elastic belt laminate 200*b* (represented by the dashed arrow "B"). During subsequent assembly operations, the chassis 102 may be folded (represented by the dashed arrow "C") so as to position the first elastic belt laminate 200*a* into a facing relationship with the second elastic belt laminate 200*b*. Bonds 246 may be applied to the overlapping belt laminates 200*a*, 200*b*. Subsequently, discrete diaper pants 100P may be formed by separating the first and second belt laminates 200*a*, 200*b* into first and second belts 106, 108 by cutting along the cross direction CD through the first and second belt laminates 200*a*, 200*b* adjacent the bonds 246 (represented by the dashed arrow "D"). As such, the bonds 246 may be divided to define the first and second side seams 178, 180, respectively. It is to be appreciated that frangible pathways 700 may be formed before and/or after combining the chassis 102 with the first elastic belt laminate 200*a* and/or a second elastic belt laminate 200*b*.

As discussed above, when frangible pathways 700 are configured to extend across severed elastic strands 168 in the first belt 106 or second belt 108, it may be relatively easier for user to tear the first belt 106 or second belt 108 along the frangible pathway 700. For example, the frangible pathways 700 may comprise a plurality of lines of weakness 704 configured such that all elastic strands 168 in the first elastic belt 106 that would otherwise extend across the frangible pathway 700 are severed at least once in the frangible pathway 700. As such, when the elastic strands 168 are severed, the first substrate 162 and second substrate 164 of the first belt 106 need only be torn along the frangible pathway 700 without having to also tear uncut elastic strands 168. As further discussed above with reference to FIG. 2A, the diaper pant 100P may include outer waist elastics 170 and inner waist elastics 172. The outer waist elastics 170 may continuously extend laterally between the first and second opposing end regions 106*a*, 106*b* of the first elastic belt 106 and between the first and second opposing end regions 108*a*, 108*b* of the second elastic belt 108. In addition, the inner waist elastics 172 may be configured with discontinuities in areas, such as for example, where the first and second elastic belts 106, 108 overlap portions of the chassis 102, such as the overlap region 850 discussed above. As further described above, the first elastic belt 106 and/or the second elastic belt 108 may be configured with low-stretch zones 701 and high-stretch zones 701. The first elastic belt 106 and/or the second elastic belt 108 may include a first high-stretch zone 703*a* and a second high-stretch zone 703*b* separated laterally by a low-stretch zone 701. It is to be appreciated that the diaper pant 100P may include various quantities of frangible pathways 700 that may be: positioned in various locations relative to the outer waist elastics 170, inner waist elastics 172, low-stretch zones 701, and high-stretch zones 703.

Figure 9:
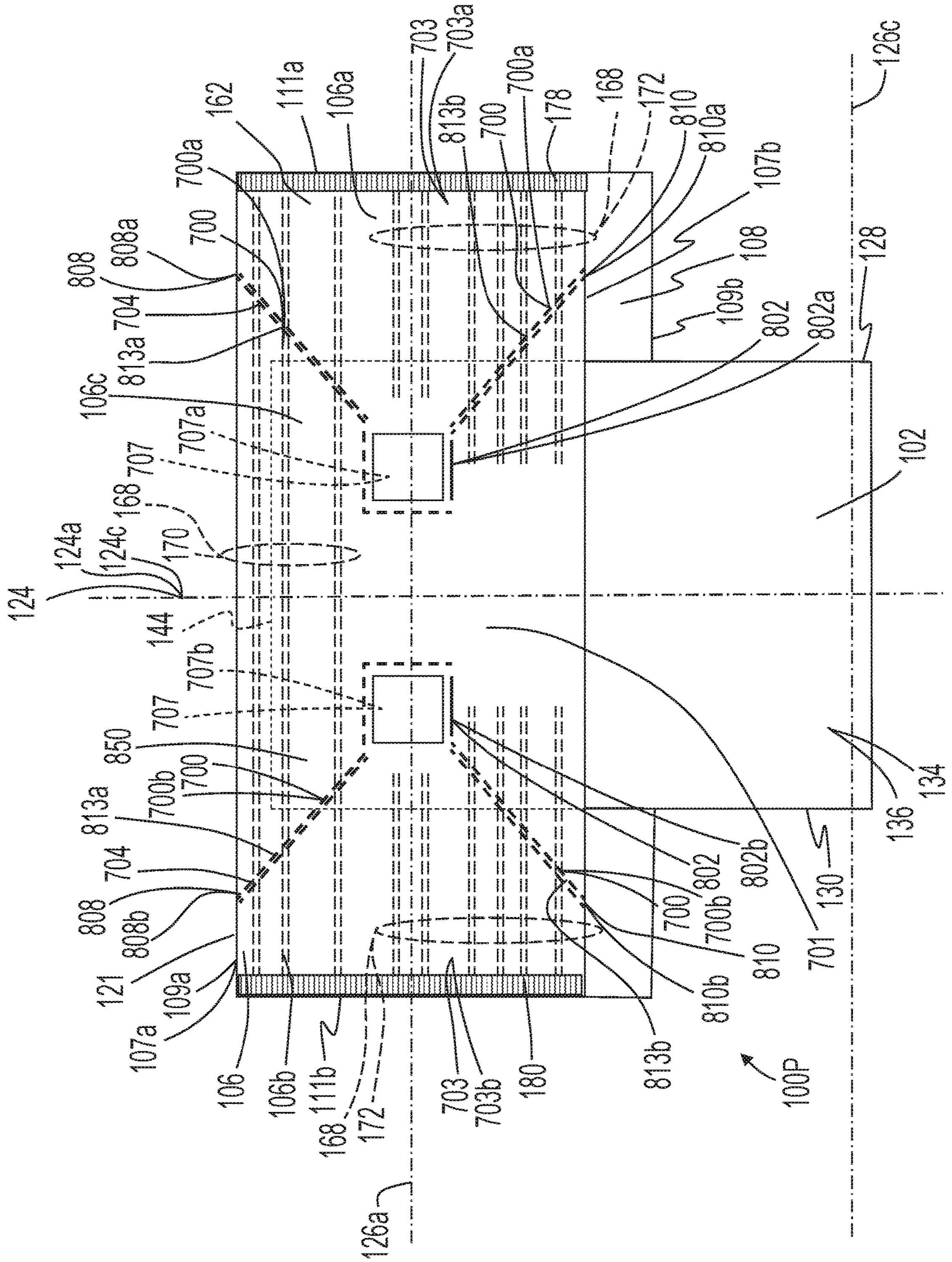
FIG. 9 shows a front plan view of the diaper pant of FIG. 6B illustrating various positional relationships with elastic material in the first belt.

FIG. 9 illustrates an example configuration of a diaper pant 100P showing various positional relationships between the frangible pathways 700 and the elastic strands 168 in the first belt 106. As shown in FIG. 9, all elastic strands 168 extending through the first tear zone 813*a* laterally between the first longitudinal edge 128 of the chassis 102 and the first distal terminus 808*a* may be severed or cut at and/or severed or cut by the lines of weakness 704 of the first frangible pathway 700*a*, and all elastic strands 168 extending through the first tear zone 813*a* laterally between the second longitudinal edge 130 of the chassis 102 and the second distal terminus 808*b* may be severed or cut at and/or severed or cut by the lines of weakness 704 of the second frangible pathway 700*b*. In some configurations, all elastic strands 168 extending through the first tear zone 813*a* and/or the second tear zone 813*b* laterally between the first accessibility opening 802*a* and the first longitudinal edge 128 of the chassis 102 may be severed or cut at and/or severed or cut by the lines of weakness 704 of the first frangible pathway 700*a*, and all elastic strands 168 extending through the first tear zone 813*a* and/or the second tear zone 813*b* laterally between the second accessibility opening 803*b* and the second longitudinal edge 130 of the chassis 102 may be severed or cut at and/or severed or cut by the lines of weakness 704 of the second frangible pathway 700*b*. In some configurations, all elastic strands 168 extending through the second tear zone 813*a* laterally between the first longitudinal edge 128 of the chassis 102 and the first proximal terminus 810*a* may be severed or cut at and/or severed or cut by the lines of weakness 704 of the first frangible pathway 700*a*, and all elastic strands 168 extending through the second tear zone 813*a* laterally between the second longitudinal edge 130 of the chassis 102 and the second proximal terminus 810*b* may be severed or cut at and/or severed or cut by the lines of weakness 704 of the second frangible pathway 700*b* may sever or cut.

Still referring to FIG. 9, lines of weakness 704 of the frangible pathways 700 may extend through severed or cut outer waist elastics 170 and may also sever or cut the outer waist elastics 170. For example, the first tear zone 813*a* of the first frangible pathway 700*a* may extend through the severed outer waist elastics 170; and the first tear zone 813*a* of the second frangible pathway 700*b* may extend through the severed outer waist elastics 170. In some configurations, outer waist elastics 170 may extend across the overlap region 850. In some configurations, outer waist elastics 170 may be positioned longitudinally between the overlap region 850 and the outer edge 107*a* of the first belt 106 and may not extend across the overlap region 850. In some configurations, outer waist elastics 170 may be severed by frangible pathways 700 in the overlap region 850, and/or outer waist elastics 170 may be severed by frangible pathways 700 outside the overlap region 850. In addition, the outer waist elastics 170 may be severed in at least two locations by first and second frangible pathways 700*a*, 700*b*. The outer waist elastics 170 may be continuously bonded with and between the first substrate 162 and the second substrate 164 of the first belt 106. As such, severed ends of the outer waist elastics 170 may not retract or may retract by relatively small distances from the lines of weakness 704 of the frangible pathways 700.

With continued reference to FIG. 9, lines of weakness 704 of the frangible pathways 700 may extend through some or all severed inner waist elastics 172 and may sever some or all the inner waist elastics 172. For example, the second tear zone 813*b* of the first frangible pathway 700*a* may extend through the severed inner waist elastics 172; and the second tear zone 813*b* of the second frangible pathway 700*b* may extend through the severed inner waist elastics 172. In some configurations, inner waist elastics 172 may be severed by frangible pathways 700 in the overlap region 850, and/or inner waist elastics 172 may be severed by frangible pathways 700 outside the overlap region 850.

In some configurations, the inner waist elastics 172 may be severed in at least three locations. For example, the inner waist elastics may be severed in a first occasion by a cutting process when forming the low-stretch zone 701, and may also be severed on second and third occasions by first and second frangible pathways 700*a*, 700*b*. The inner waist elastics 172 may also be continuously bonded with and between the first substrate 162 and the second substrate 164 of the first belt 106 in the high-stretch zones 703. As such, the severed ends of the inner waist elastics 172 may not retract or may retract by relatively small distances from the lines of weakness 704 of the frangible pathways 700.

In some configurations, the first high-stretch zone 703*a* and the second high-stretch 703*b* may partially overlap with the overlap region 850 or may be located entirely laterally outside the overlap region 850. As discussed above, the inner waist elastics 172 may be severed during cutting operations when forming the low-stretch zone 701 and the high-stretch zones 703. When forming the low-stretch zone 701, cut inner waist elastics 172 may retract laterally outward by the same or different distances. In some configurations, some inner waist elastics 172 may be longitudinally aligned with the fastener components 704, but may be configured to contract to locations laterally outward of the fastener components 704. As such, the inner waist elastics 172 of the high-stretch zones 703 may be located laterally outward from fastener components 704 and may be configured so as to not overlap the fastener components 704.

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g., Quick-Freeze, Miller-Stephenson Company, Danbury, CT), or with an appropriate solvent that will remove adhesive but not swell, alter, or destroy elastic fibers. The length of each elastic fiber in its relaxed state is measured and recorded in millimeters (mm) to the nearest mm Calculation of Average-Dtex For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-}Dtex = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas a k for the elastic fiber, in units of micrometers squared ($\mu m^2$), is recorded to the nearest 0.1 $\mu m^2$. The decitex $d_k$ of the kth elastic fiber measured is calculated by:

$$d_k = 10\,000\,\text{m} \times \alpha_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter ($g/cm^3$). For any elastic fiber analyzed, the experimentally determined $L_k$ and $d_k$ values are subsequently used in the expression above for Average-Dtex.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing}=d/(n-1) \text{ where } n>1$$

report to the nearest 0.1 mm

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, MN) using a load cell for which the forces measured are within 1% to 90% of the limit of the cell. Articles are conditioned at 23° C.±2° C. and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Combinations

A1. An absorbent article comprising: a first belt comprising an inner wearer facing surface and an outer garment facing surface, the first belt further comprising a laterally extending inner edge and a laterally extending outer edge, the outer edge positioned longitudinally outward of the inner edge; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, the chassis comprising a longitudinally extending first side edge and a longitudinally extending second side edge laterally separated from the first side edge by a first end edge and a second end edge longitudinally separate from the first end edge, and wherein longitudinally opposing end regions of the chassis are connected with the first belt and the second belt; wherein a portion of the chassis overlaps the inner wearer facing surface of the first belt to define a chassis overlap region; a frangible pathway in the first belt extending across the overlap region between a proximal terminus on the inner edge and a distal terminus on the outer edge of the first belt, the first frangible pathway comprising a first tear zone extending from the overlap region to the distal terminus, and a second tear zone extending from the overlap region to the proximal terminus; and the distal terminus and the proximal terminus positioned laterally between the first side edge of the chassis and the first side seam.

A2. The absorbent article of paragraph A1, wherein the first belt further comprises: elastic strands positioned between and connected with a first substrate and a second substrate; and wherein the frangible pathway comprises lines of weakness.

A3. The absorbent article of paragraph A2, wherein some elastic strands are severed at the lines of weakness, and wherein the severed elastic strands are continuously bonded between the first substrate and the second substrate.

A4. The absorbent article of either paragraph A2 or A3, wherein all elastic strands extending through the first tear zone between the first side edge of the chassis and the distal terminus are severed at the lines of weakness.

A5. The absorbent article of any of paragraphs A2 to A4, wherein elastic strands extending through the second tear zone between the first side edge of the chassis and the proximal terminus are severed at the lines of weakness.

A6. The absorbent article of any of paragraphs A2 to A5, wherein the lines weakness cut at least one elastic strand extending through the first tear zone or the second tear zone in at least one location between the first side edge of the chassis and the second side edge of the chassis.

A7. The absorbent article of paragraph A6, wherein the lines weakness do not cut at least one elastic strand extending between the first side edge of the chassis and the second side edge of the chassis.

A8. The absorbent article of any of paragraphs A2 to A7, wherein the lines of weakness comprise discrete cut lines.

A9. The absorbent article of any of paragraphs A2 to A8, wherein the first substrate and the second substrate comprise nonwovens and wherein the lines of weakness comprise discrete bonds wherein materials of the nonwovens are at least partly fused together.

A10. The absorbent article of any of paragraphs A1 to A9, further comprising a fastener component connected with the inner wearer facing surface of the first belt in the overlap region adjacent the frangible pathway, the fastener component adapted to refastenably connect with at least one other component of the absorbent article.

A11. The absorbent article of paragraph A10, further comprising an accessibility opening in the first belt positioned in the overlap region adjacent the fastener component.

A12. The absorbent article of paragraph A11, wherein the first tear zone extends from the accessibility opening to the distal terminus, and the second tear zone extends from the accessibility opening to the proximal terminus.

A13. The absorbent article of either paragraph A11 or A12, wherein the accessibility opening comprises a slit in the first belt.

A14. The absorbent article of paragraph A13, wherein the slit extends along a line in a lateral direction to define an angle from about 0 degrees to about 10 degrees with respect to the outer edge of the first belt.

A15. The absorbent article of either paragraph A13 or A14, wherein the slit is curved and extends in a longitudinal direction.

A16. The absorbent article of any of paragraphs A11 to A14, wherein the accessibility opening is positioned between the fastener component and the inner edge of the first belt.

A16. The absorbent article of any of paragraphs A11 to A14, wherein the accessibility opening is positioned between the fastener component and the outer edge of the first belt.

A17. The absorbent article of any of paragraphs A11 to A16, wherein the frangible pathway and the accessibility opening partially surround the fastener component.

A18. The absorbent article of any of paragraphs A11 to A17, wherein the fastener component comprises hooks, and the wherein the hooks extend toward the backsheet.

A19. The absorbent article of any of paragraphs A11 to A18, wherein the frangible pathway extends through the fastener component and divides the fastener component into at least two parts.

A20. The absorbent article of any of paragraphs A11 to A19, wherein the chassis overlap region comprises an adherence region where an adhesive is positioned between the chassis and the inner wearer facing surface of the first belt, and wherein the accessibility opening is positioned outside the adherence region.

Bio-Based Content for Components

Components of the absorbent articles described herein may at least partially be comprised of bio-based content as described in U.S. Pat. Appl. No. 2007/0219521A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a first belt comprising an inner wearer facing surface and an outer garment facing surface, the first belt further comprising a laterally extending inner edge and a laterally extending outer edge, the outer edge positioned longitudinally outward of the inner edge, wherein the first belt further comprises elastic strands positioned between and connected with a first substrate and a second substrate;

a second belt, wherein laterally opposing end portions of the second belt are connected with laterally opposing end portions of the first belt at a first side seam and a second side seam to form a waist opening;

a chassis comprising a topsheet, a backsheet, and an absorbent core positioned between the topsheet and the backsheet, the chassis comprising a longitudinally extending first side edge and a longitudinally extending second side edge laterally separated from the first side edge by a first end edge and a second end edge longitudinally separate from the first end edge, and wherein longitudinally opposing end regions of the chassis are connected with the first belt and the second belt;

wherein a portion of the chassis overlaps the inner wearer facing surface of the first belt to define a chassis overlap region;

a frangible pathway in the first belt extending across the overlap region between a proximal terminus on the inner edge and a distal terminus on the outer edge of the first belt, the frangible pathway comprising a first tear zone extending from the overlap region to the distal terminus, and a second tear zone extending from the overlap region to the proximal terminus, wherein the frangible pathway comprises lines of weakness, wherein the lines of weakness comprise discrete cut lines through at least one of the first substrate and the second substrate; and the distal terminus and the proximal terminus positioned laterally between the first side edge of the chassis and the first side seam;

wherein all elastic strands extending through the first tear zone between the first side edge of the chassis and the distal terminus are severed at the lines of weakness, and wherein elastic strands extending through the second tear zone between the first side edge of the chassis and the proximal terminus are severed at the lines of weakness; and wherein the lines weakness cut at least one elastic strand extending through the first tear zone or the second tear zone in the overlap region; and wherein the lines weakness do not cut at least one elastic strand extending into the overlap region.

2. The absorbent article of claim 1, wherein some elastic strands are severed at the lines of weakness, and wherein the severed elastic strands are continuously bonded between the first substrate and the second substrate.

3. The absorbent article of claim 1, wherein the first substrate and the second substrate comprise nonwovens.

4. The absorbent article of claim 1, further comprising a fastener component connected with the inner wearer facing surface of the first belt in the overlap region adjacent the frangible pathway, the fastener component adapted to refastenably connect with at least one other component of the absorbent article.

5. The absorbent article of claim 4, further comprising an accessibility opening in the first belt positioned in the overlap region adjacent the fastener component.

6. The absorbent article of claim 5, wherein the first tear zone extends from the accessibility opening to the distal terminus, and the second tear zone extends from the accessibility opening to the proximal terminus.

7. The absorbent article of claim 5, wherein the accessibility opening comprises a slit in the first belt.

8. The absorbent article of claim 7, wherein the slit extends along a line in a lateral direction to define an angle from about 0 degrees to about 10 degrees with respect to the outer edge of the first belt.

9. The absorbent article of claim 7, wherein the slit is curved and extends in a longitudinal direction.

10. The absorbent article of claim 5, wherein the accessibility opening is positioned between the fastener component and the inner edge of the first belt.

11. The absorbent article of claim 5, wherein the accessibility opening is positioned between the fastener component and the outer edge of the first belt.

12. The absorbent article of claim 5, wherein the frangible pathway and the accessibility opening partially surround the fastener component.

13. The absorbent article of claim 5, wherein the fastener component comprises hooks, and the wherein the hooks extend toward the backsheet.

14. The absorbent article of claim 5, wherein the frangible pathway extends through the fastener component and divides the fastener component into at least two parts.

15. The absorbent article of claim 5, wherein the chassis overlap region comprises an adherence region where an adhesive is positioned between the chassis and the inner wearer facing surface of the first belt, and wherein the accessibility opening is positioned outside the adherence region.

16. An absorbent article comprising:

a first belt comprising an inner wearer facing surface and an outer garment facing surface, the first belt further comprising a laterally extending inner edge and a laterally extending outer edge, the outer edge positioned longitudinally outward of the inner edge, wherein the first belt further comprises elastic strands positioned between and connected with a first substrate and a second substrate;

a second belt, wherein laterally opposing end portions of the second belt are connected with laterally opposing end portions of the first belt at a first side seam and a second side seam to form a waist opening;

a chassis comprising a topsheet, a backsheet, and an absorbent core positioned between the topsheet and the backsheet, the chassis comprising a longitudinally extending first side edge and a longitudinally extending second side edge laterally separated from the first side edge by a first end edge and a second end edge longitudinally separate from the first end edge, and wherein longitudinally opposing end regions of the chassis are connected with the first belt and the second belt;

wherein a portion of the chassis overlaps the inner wearer facing surface of the first belt to define a chassis overlap region;

an accessibility opening in the first belt in the overlap region, the accessibility opening comprising a slit penetrating at least one of the first substrate and the second substrate;

a frangible pathway in the first belt extending across the overlap region between a proximal terminus on the inner edge and a distal terminus on the outer edge of the first belt, the frangible pathway comprising a first tear zone extending from the accessibility opening to the distal terminus, and a second tear zone extending from the accessibility opening to the proximal terminus, wherein the frangible pathway comprises lines of weakness, wherein the lines of weakness comprise discrete cut lines through at least one of the first substrate and the second substrate; and the distal terminus and the proximal terminus positioned laterally between the first side edge of the chassis and the first side seam; and wherein all elastic strands extending through the first tear zone between the first side edge of the chassis and the distal terminus are severed at the lines of weakness, and wherein elastic strands extending through the second tear zone between the first side edge of the chassis and the proximal terminus are severed at the lines of weakness; and wherein the chassis overlap region comprises an adherence region where an adhesive bonds the chassis with the inner wearer facing surface of the first belt, and wherein the accessibility opening is positioned outside the adherence region.

* * * * *